US012324622B2

(12) United States Patent
Weinkam et al.

(10) Patent No.: US 12,324,622 B2
(45) Date of Patent: *Jun. 10, 2025

(54) SYSTEMS AND METHODS FOR ABLATING TISSUE

(71) Applicant: Kardium Inc., Burnaby (CA)

(72) Inventors: Daniel Robert Weinkam, Coquitlam (CA); Daniel Martin Reinders, Surrey (CA); Darrell Anthony Harrington, Canoga Park, CA (US); Douglas Wayne Goertzen, New Westminster (CA); Michael Hermann Weber, Sointula (CA)

(73) Assignee: KARDIUM INC., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/610,997

(22) Filed: Mar. 20, 2024

(65) Prior Publication Data
US 2024/0252238 A1  Aug. 1, 2024

Related U.S. Application Data

(63) Continuation of application No. 17/360,026, filed on Jun. 28, 2021, now Pat. No. 11,969,206, which is a
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/283* (2021.01); *A61B 5/287* (2021.01);
(Continued)

(58) Field of Classification Search
CPC ..... A61B 18/1492; A61B 5/287; A61B 5/339; A61B 5/349; A61B 5/352; A61B 5/4848
See application file for complete search history.

(56) References Cited

U.S. PATENT DOCUMENTS

| 5,485,849 A | 1/1996 | Panescu et al. |
| D441,761 S | 5/2001 | Machida et al. |
| (Continued) | | |

FOREIGN PATENT DOCUMENTS

| WO | 9520349 A1 | 8/1995 |
| WO | 9724981 A2 | 7/1997 |
| (Continued) | | |

OTHER PUBLICATIONS

Extended European Search Report issued in European Application No. 14905089.0 mailed Oct. 9, 2017.
(Continued)

*Primary Examiner* — Joseph M Dietrich
(74) *Attorney, Agent, or Firm* — ROSSI, KIMMS & McDOWELL LLP

(57) ABSTRACT

Intra-cardiac voltage data display systems display a plurality of data sets derived at least from intra-cardiac voltage data sampled by an electrode. In some embodiments, at least some of the data sets are derived from a portion of the intra-cardiac voltage data that excludes an excludable portion of the intra-cardiac voltage data having a relationship with an occurrence of a particular cardiac event to facilitate identification of the existence of a transmural lesion in tissue adjacent the electrode. In some embodiments, the particular cardiac event is the occurrence of an R wave in the cardiac cycle, and the excludable portion is a V wave in the cardiac cycle.

9 Claims, 33 Drawing Sheets

Related U.S. Application Data continuation of application No. 16/411,546, filed on May 14, 2019, now Pat. No. 11,076,914, which is a continuation of application No. 15/499,193, filed on Apr. 27, 2017, now Pat. No. 10,327,844, which is a continuation of application No. PCT/US2014/063058, filed on Oct. 30, 2014.

(51) Int. Cl.

| | | |
|---|---|---|
| A61B 5/283 | (2021.01) | |
| A61B 5/287 | (2021.01) | |
| A61B 5/316 | (2021.01) | |
| A61B 5/339 | (2021.01) | |
| A61B 5/349 | (2021.01) | |
| A61B 5/352 | (2021.01) | |
| A61B 18/00 | (2006.01) | |
| A61B 18/12 | (2006.01) | |
| A61B 18/16 | (2006.01) | |
| A61B 90/00 | (2016.01) | |
| A61N 1/05 | (2006.01) | |

(52) U.S. Cl.
CPC ............... *A61B 5/316* (2021.01); *A61B 5/339* (2021.01); *A61B 5/349* (2021.01); *A61B 5/352* (2021.01); *A61B 5/4848* (2013.01); *A61B 5/6853* (2013.01); *A61B 5/6858* (2013.01); *A61B 5/7285* (2013.01); *A61B 5/743* (2013.01); *A61B 5/7275* (2013.01); *A61B 5/7445* (2013.01); *A61B 2018/0016* (2013.01); *A61B 2018/00214* (2013.01); *A61B 2018/0022* (2013.01); *A61B 2018/00267* (2013.01); *A61B 2018/00351* (2013.01); *A61B 2018/00357* (2013.01); *A61B 2018/00577* (2013.01); *A61B 2018/00642* (2013.01); *A61B 2018/00839* (2013.01); *A61B 2018/00988* (2013.01); *A61B 2018/124* (2013.01); *A61B 18/16* (2013.01); *A61B 2090/061* (2016.02); *A61B 2505/05* (2013.01); *A61N 1/056* (2013.01)

(56) References Cited

U.S. PATENT DOCUMENTS

| | | |
|---|---|---|
| D462,077 S | 8/2002 | Greminger |
| 6,663,627 B2 | 12/2003 | Francischelli et al. |
| D632,699 S | 2/2011 | Judy et al. |
| 7,899,522 B1 | 3/2011 | Koh et al. |
| 7,974,983 B2 | 7/2011 | Goeldi |
| D652,048 S | 1/2012 | Joseph |
| D652,052 S | 1/2012 | Judy et al. |
| 8,165,666 B1 | 4/2012 | Briggs et al. |
| D674,401 S | 1/2013 | Trumble et al. |
| 8,346,339 B2 | 1/2013 | Kordis et al. |
| D694,252 S | 11/2013 | Helm |
| D694,253 S | 11/2013 | Helm |
| 8,806,359 B2 | 8/2014 | Garibaldi et al. |
| 8,838,216 B2 | 9/2014 | Francis et al. |
| D716,820 S | 11/2014 | Wood |
| D717,331 S | 11/2014 | Lin |
| D738,889 S | 9/2015 | Balles et al. |
| D745,018 S | 12/2015 | Balles et al. |
| D751,580 S | 3/2016 | Herrera et al. |
| 9,492,228 B2 | 11/2016 | Lopes et al. |
| 10,327,844 B2 * | 6/2019 | Weinkam ............... A61B 5/743 |
| 11,076,914 B2 * | 8/2021 | Weinkam ............... A61B 5/283 |
| 11,969,206 B2 * | 4/2024 | Weinkam ............ A61B 18/1492 |
| 2002/0058870 A1 | 5/2002 | Panescu et al. |
| 2006/0235476 A1 | 10/2006 | Gunderson |
| 2008/0004534 A1 | 1/2008 | Gelbart et al. |
| 2008/0071183 A1 | 3/2008 | Thomas et al. |
| 2009/0036942 A1 | 2/2009 | Conley et al. |
| 2010/0023004 A1 | 1/2010 | Francischelli et al. |
| 2010/0152795 A1 | 6/2010 | Schecter |
| 2010/0262901 A1 | 10/2010 | Disalvo |
| 2010/0280399 A1 | 11/2010 | Francis et al. |
| 2010/0318408 A1 | 12/2010 | Sankaran et al. |
| 2011/0054559 A1 | 3/2011 | Rosenberg |
| 2011/0251505 A1 | 10/2011 | Narayan et al. |
| 2012/0089935 A1 | 4/2012 | Santori et al. |
| 2012/0123926 A1 | 5/2012 | Selin et al. |
| 2012/0184863 A1 | 7/2012 | Harlev et al. |
| 2012/0237093 A1 | 9/2012 | Turgeman |
| 2012/0321759 A1 | 12/2012 | Marinkovich et al. |
| 2013/0006131 A1 | 1/2013 | Narayan |
| 2013/0203027 A1 | 8/2013 | De Villers-Sidani et al. |
| 2013/0205240 A1 | 8/2013 | Ling et al. |
| 2013/0246959 A1 | 9/2013 | Fukuda et al. |
| 2013/0259903 A1 | 10/2013 | Mortenson et al. |
| 2013/0262730 A1 | 10/2013 | Al-Ali et al. |
| 2013/0268019 A1 | 10/2013 | Gupta et al. |
| 2013/0274562 A1 | 10/2013 | Ghaffari et al. |
| 2013/0281854 A1 | 10/2013 | Stuebe et al. |
| 2013/0289668 A1 | 10/2013 | Nirenberg et al. |
| 2013/0296823 A1 | 11/2013 | Melker et al. |
| 2013/0296908 A1 | 11/2013 | Schulte et al. |
| 2013/0298062 A1 | 11/2013 | Dolgos et al. |
| 2013/0310826 A1 | 11/2013 | Goertzen et al. |
| 2013/0310828 A1 | 11/2013 | Reinders et al. |
| 2014/0005563 A1 | 1/2014 | Ramanathan et al. |
| 2014/0067426 A1 | 3/2014 | Neff |
| 2014/0088393 A1 | 3/2014 | Bernstein et al. |
| 2014/0129151 A1 | 5/2014 | Bhavaraju et al. |
| 2014/0152669 A1 | 6/2014 | Omiya |
| 2014/0187991 A1 | 7/2014 | Thakur et al. |
| 2014/0200429 A1 | 7/2014 | Spector et al. |
| 2014/0245171 A1 | 8/2014 | Jaycobs et al. |
| 2014/0276140 A1 | 9/2014 | Kinghorn |
| 2014/0276181 A1 | 9/2014 | Sun et al. |
| 2014/0282195 A1 | 9/2014 | Nixon et al. |
| 2014/0282256 A1 | 9/2014 | Fish et al. |
| 2014/0310635 A1 | 10/2014 | Lett et al. |
| 2016/0119210 A1 | 4/2016 | Koehler et al. |

FOREIGN PATENT DOCUMENTS

| | | | |
|---|---|---|---|
| WO | 2008135731 | A1 | 11/2008 |
| WO | 2012100184 | A2 | 7/2012 |
| WO | 2012100185 | A2 | 7/2012 |
| WO | 2012151301 | A1 | 11/2012 |

OTHER PUBLICATIONS

Casaleggio et al. "Diastolic Heart Activity Inspection from Intracardiac Electrogram Analysis", Computing in Cardiology, 2010: 737-740.

Response to Office Action filed in U.S. Appl. No. 29/507,789 on Oct. 3, 2017.

Office Action issued in U.S. Appl. No. 29/507,789 mailed Nov. 14, 2017.

Office Action issued in European Application No. 14905089.0 mailed Mar. 15, 2019.

Office Action issued in U.S. Appl. No. 29/507,789 mailed Aug. 8, 2017.

Amendment filed in U.S. Appl. No. 29/507,789 on May 18, 2017.

Office Action issued in U.S. Appl. No. 15/499,193 mailed Jun. 29, 2018.

Response filed in U.S. Appl. No. 15/499,193 on Sep. 14, 2018.

Supplemental Amendment filed in U.S. Appl. No. 15/499,193 on Nov. 2, 2018.

Notice of Allowance issued in U.S. Appl. No. 15/499,193 mailed Feb. 12, 2019.

Response After Final Rejection filed in U.S. Appl. No. 29/507,789 on Mar. 6, 2018.

Bortone et al. "Unipolar Signal Modification as a Guide for Lesion Creation During Radiofrequency Application in the Left Atrium." Circulation Arrhythmia and Electrophysiology. Dec. 2013:1095-1102.

(56) References Cited

OTHER PUBLICATIONS

Otomo et al. "Local Unipolar and Bipolar Electrogram Criteria for Evaluating the Transmurality of Atrial Ablation Lesions at Different Catheter Orientations Relative to the Endocardial Surface." Heart Rhythm Society. Sep. 2010:1291-1300.
Merkely et al. "Effects of Radiofrequency Ablation on Monophasic Action Potentials." IEEE Engineering in Medicine and Biology. Jan./Feb. 2002:69-73.
Han et al. "How to Achieve Complete and Permanent Pulmonary Vein Isolation without Complications." The Korean Society of Cardiology. Sep. 2014:291-300.
Umapathy et al. "Phase Mapping of Cardiac Fibrillation." Circulation Arrhythmia and Electrophysiology. May 5, 2014.
International Search Report issued in Intl. Appln. No. PCT/US2014/063058 mailed Jul. 23, 2015.
Written Opinion issued in Intl. Appln. No. PCT/US2014/063058 mailed Jul. 23, 2015.
Office Action issued in U.S. Appl. No. 29/507,789 mailed Jun. 22, 2016.
Office Action issued in U.S. Appl. No. 29/507,789 mailed Feb. 22, 2017.
Hartley et al. "Doppler Velocity Measurements from Large and Small Arteries of Mice." American Physiological Society, Aug. 1, 2011. Web. Feb. 7, 2017.
"Monitor Blood Pressure and EKG Simultaneously Using Logger Pro." Vernier Software and Technology. Jul. 29, 2011. Web. Feb. 7, 2017.
Amendment filed in U.S. Appl. No. 29/507,789 on Nov. 21, 2016.
U.S. Appl. No. 29/507,789, filed Oct. 30, 2014 (a copy is not included because the cited application is not available to the public and the Examiner has ready access to the cited application).
Intention to Grant issued in European Application No. 14905089.0 mailed Oct. 11, 2019.
Extended European Search Report issued in European Application No. 20162515.9 mailed Jul. 3, 2020.
Office Action issued in copending U.S. Appl. No. 16/411,546 mailed Feb. 4, 2021.
Amendment filed in copending U.S. Appl. No. 16/411,546 on Apr. 19, 2021.
Notice of Allowance issued in copending U.S. Appl. No. 16/411,546 mailed Jun. 10, 2021.
Communication Pursuant to Article 94(3) EPC issued in European Appln. No. 20162515.9, mailed Jul. 19, 2023.
Preliminary Amendment filed in copending U.S. Appl. No. 17/360,026 on Sep. 29, 2022.
Office Action issued in copending U.S. Appl. No. 17/360,026 mailed Dec. 21, 2023.
Response filed in copending U.S. Appl. No. 17/360,026 on Jan. 15, 2024.
Notice of Allowance issued in copending U.S. Appl. No. 17/360,026 mailed Feb. 21, 2024.
Communication under Rule 71(3) EPC issued in European Appln. No. 20162515.9, mailed Dec. 12, 2024.

* cited by examiner

600

IDENTIFY A RESPECTIVE OCCURRENCE OF A PARTICULAR CARDIAC EVENT IN EACH OF THE PLURALITY OF CARDIAC CYCLES —616

IDENTIFY, FOR EACH RESPECTIVE ONE OF THE CARDIAC CYCLES, A RESPECTIVE FIRST PORTION OF THE INTRA-CARDIAC VOLTAGE DATA IDENTIFIED IN ACCORDANCE WITH A PREDETERMINED TEMPORAL RELATIONSHIP WITH THE RESPECTIVE OCCURRENCE OF THE PARTICULAR CARDIAC EVENT IDENTIFIED IN THE RESPECTIVE ONE OF THE CARDIAC CYCLES —618

FIG. 6F

SYSTEMS AND METHODS FOR ABLATING TISSUE

CROSS-REFERENCE TO RELATED APPLICATIONS

This application is a continuation of U.S. patent application Ser. No. 17/360,026, filed Jun. 28, 2021, now U.S. Pat. No. 11,969,206, issued Apr. 30, 2024, which is a continuation of U.S. patent application Ser. No. 16/411,546, filed May 14, 2019, now U.S. Pat. No. 11,076,914, issued Aug. 3, 2021, which is a continuation of U.S. patent application Ser. No. 15/499,193, filed Apr. 27, 2017, now U.S. Pat. No. 10,327,844, issued Jun. 25, 2019, which is a continuation of International Application No. PCT/US2014/063058, filed Oct. 30, 2014, wherein the entire disclosure of each of these applications is hereby incorporated herein by reference.

TECHNICAL FIELD

Aspects of this disclosure generally are related to systems and methods for activating transducers to ablate tissue and providing information related to the tissue ablation.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy, and cryogenic techniques. The procedure is performed with a high success rate under the direct vision that is provided in open procedures, but is relatively complex to perform intravascularly or percutaneously because of the difficulty in creating lesions with the desired characteristics. Various problems may occur if the lesions are incorrectly formed. For example, unless the formed lesions are transmural (e.g., extend fully throughout a thickness of the target cardiac tissue), their ability to block paths taken within the heart by spurious electrical signals may be compromised. In some cases, increased levels of ablative energy, increased delivery times of the ablative energy, or both may allow for lesion transmurality to be achieved in the target cardiac tissue. However, since tissue thickness is variable and may not be easily or readily ascertained in percutaneous procedures, various tissue structures that underlie the target cardiac tissue, but which should not be ablated, may be at risk of being subjected to the ablation energy supplied with increased levels or longer durations. One particular undesired complication that may arise is the formation of atrio-esophageal fistulas.

In this regard, there is a need for improved intra-bodily-cavity transducer-based device systems or control mechanisms thereof that can provide improved indications of lesion transmurality, especially during the formation of the lesion.

SUMMARY

At least the above-discussed need is addressed and technical solutions are achieved by various embodiments of the present invention. In some embodiments, device systems and methods executed by such systems exhibit enhanced capabilities for the control of ablation activation of various transducers, which may be located within a bodily cavity, such as an intra-cardiac cavity. In some embodiments, the systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Various ones of the transducers may be used to detect electrophysiological activity in the bodily cavity. Other advantages will become apparent from the teaching herein to those of skill in the art.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The program may include data reception instructions configured to cause reception of intra-cardiac voltage data via the input-output device system, the intra-cardiac voltage data sampled by an electrode over a period of time including a plurality of cardiac cycles. The program may include cardiac event identification instructions configured to identify a respective occurrence of a particular cardiac event in each of the plurality of cardiac cycles. The program may include data identification instructions configured to identify, for each respective one of the plurality of cardiac cycles, a respective first portion of the intra-cardiac voltage data sampled during the respective one of the plurality of cardiac cycles, each respective first portion of the intra-cardiac voltage data identified in accordance with a predetermined temporal relationship with the respective occurrence of the particular cardiac event identified in the respective one of the plurality of cardiac cycles. The program may include excludable data identification instructions configured to identify, for each respective one of the plurality of cardiac cycles, a particular portion of the intra-cardiac voltage data sampled during the respective one of the plurality of cardiac cycles as an excludable portion of the intra-cardiac voltage data sampled by the electrode during the respective one of the plurality of cardiac cycles, each identified excludable portion of the intra-cardiac voltage data including some but not all of the intra-cardiac voltage data sampled by the electrode during the respective one of the plurality of cardiac cycles. The program may include data derivation instructions configured to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified excludable portion of the intra-cardiac voltage data sampled by the electrode during the respective one of the plurality of cardiac cycles. The program may include display instructions configured to cause the input-output device system to concurrently display the plurality of data sets.

In some embodiments, the excludable data identification instructions may be configured to identify each excludable portion of the intra-cardiac voltage data sampled by the electrode during the respective one of the plurality of cardiac cycles as including the identified respective first portion of the intra-cardiac voltage data sampled during the respective one of the plurality of cardiac cycles. In some embodiments, the data identification instructions may be configured to identify each respective first portion of the intra-cardiac voltage data as including a portion of the intra-cardiac voltage data sampled by the electrode at least in part during the occurrence of the particular cardiac event identified in the respective one of the plurality of cardiac cycles. In some embodiments, the data identification instructions may be configured to identify each respective first portion of the intra-cardiac voltage data as including a portion of the intra-cardiac voltage data sampled by the electrode at least in part during the respective one of the plurality of cardiac cycles after the occurrence of the particular cardiac event identified in the respective one of the plurality of cardiac cycles. In some embodiments, the data identification instructions may be configured to identify each respective first portion of the intra-cardiac voltage data as including a portion of the intra-cardiac voltage data sampled by the electrode at least in part during the respective one of the plurality of cardiac cycles before the occurrence of the particular cardiac event identified in the respective one of the plurality of cardiac cycles. In some embodiments, the data identification instructions may be configured to identify each respective first portion of the intra-cardiac voltage data as including a portion of the intra-cardiac voltage data sampled by the electrode during a predetermined time interval that includes the occurrence of the particular cardiac event identified in the respective one of the plurality of cardiac cycles.

In some embodiments, the cardiac event identification instructions may be configured to identify the respective occurrence of the particular cardiac event in each respective one of the plurality of cardiac cycles from data other than the intra-cardiac voltage data sampled by the electrode. In some embodiments, the cardiac event identification instructions may be configured to identify the respective occurrence of the particular cardiac event in each respective one of the plurality of cardiac cycles from electrocardiogram data. In some embodiments, the cardiac event identification instructions may be configured to identify the respective occurrence of the particular cardiac event in each respective one of the plurality of cardiac cycles as including a maximum absolute voltage value in the electrocardiogram data in the respective one of the plurality of cardiac cycles. In some embodiments, the cardiac event identification instructions may be configured to identify the respective occurrence of the particular cardiac event in each respective one of the plurality of cardiac cycles as a respective occurrence of an R wave in the electrocardiogram data during the respective one of the plurality of cardiac cycles. In some embodiments, the cardiac event identification instructions may be configured to identify the respective occurrence of the particular cardiac event in each respective one of the plurality of cardiac cycles as a respective occurrence of at least part of a QRS complex in the electrocardiogram data during the respective one of the plurality of cardiac cycles, a respective occurrence of a P wave in the electrocardiogram data during the respective one of the plurality of cardiac cycles, or a respective occurrence of a T wave in the electrocardiogram data during the respective one of the plurality of cardiac cycles.

In some embodiments, the cardiac event identification instructions may be configured to identify the respective occurrence of the particular cardiac event in each respective one of the plurality of cardiac cycles as a respective occurrence of ventricular systole during the respective one of the plurality of cardiac cycles. In some embodiments, the cardiac event identification instructions may be configured to identify the respective occurrence of the particular cardiac event in each respective one of the plurality of cardiac cycles as a respective occurrence of ventricular systole during the respective one of the plurality of cardiac cycles, a respective occurrence of ventricular diastole during the respective one of the plurality of cardiac cycles, a respective occurrence of atrial systole during the respective one of the plurality of cardiac cycles, or a respective occurrence of atrial diastole during the respective one of the plurality of cardiac cycles.

In some embodiments, the cardiac event identification instructions may be configured to identify the respective occurrence of the particular cardiac event in each respective one of the plurality of cardiac cycles from the intra-cardiac voltage data sampled by the electrode. In some embodiments, the cardiac event identification instructions may be configured to identify the respective occurrence of the particular cardiac event in each respective one of the plurality of cardiac cycles at least from intra-cardiac electrogram data derived from intra-cardiac voltage data other than the intra-cardiac voltage data sampled by the electrode. In some embodiments, the cardiac event identification instructions may be configured to identify the respective occurrence of the particular cardiac event in each respective one of the plurality of cardiac cycles as a respective occurrence of a V wave in the intra-cardiac electrogram data, the V wave occurring during the respective one of the plurality of cardiac cycles.

In some embodiments, the data derivation instructions may be configured to derive each respective one of the plurality of data sets at least in part from a first respective part of the respective second portion of the intra-cardiac voltage data sampled by the electrode during the respective one of the plurality of cardiac cycles, the first respective part including a maximum value as compared with other parts of the respective second portion of the intra-cardiac voltage data sampled by the electrode during the respective one of the plurality of cardiac cycles. In some embodiments, the data derivation instructions may be configured to derive each respective one of the plurality of data sets at least in part from a second respective part of the respective second portion of the intra-cardiac voltage data sampled by the electrode during the respective one of the plurality of cardiac cycles, the second respective part including a minimum value as compared with other parts of the respective second portion of the intra-cardiac voltage data sampled by the electrode during the respective one of the plurality of cardiac cycles.

In some embodiments, each of the plurality of data sets may include data representative of a maximum absolute value in the respective second portion of the intra-cardiac voltage data sampled by the electrode during the respective one of the plurality of cardiac cycles. In some embodiments, each of the plurality of data sets may include data representative of a difference between a maximum value and a minimum value in the respective second portion of the intra-cardiac voltage data sampled by the electrode during the respective one of the plurality of cardiac cycles. In some embodiments, each of the plurality of data sets may include data representative of a difference between two values in the respective second portion of the intra-cardiac voltage data sampled by the electrode during the respective one of the plurality of cardiac cycles.

In some embodiments, the program may include activation instructions configured to cause the electrode to transmit energy sufficient to cause tissue ablation at least during the sampling of the intra-cardiac voltage data by the electrode over the period of time including the plurality of cardiac cycles.

In some embodiments, the display instructions may be configured to cause the input-output device system to sequentially display each of the plurality of data sets until all of the plurality of data sets are concurrently displayed by the input-output device system. In some embodiments, the display instructions may be configured to cause the input-output device system to sequentially display each of the plurality of data sets according to a first order that is consistent with an order of the plurality of cardiac cycles during the period of time. In some embodiments, the display instructions may be configured to cause the input-output device system to display the plurality of the data sets in a first spatial order representative of an order of the plurality of cardiac cycles during the period of time. In some embodiments, the display instructions may be configured to cause the input-output device system to sequentially display each of the plurality of data sets according to a first order that is consistent with the order of the plurality of cardiac cycles during the period of time. In some embodiments, the display instructions may be configured to cause the input-output device system to display an intra-cardiac electrogram concurrently with the plurality of data sets, the intra-cardiac electrogram derived from at least a portion of the intra-cardiac voltage data sampled by the electrode, and the intra-cardiac electrogram undergoing a biphasic to monophasic transformation during at least part of the sequential display of each of the plurality of data sets. In some embodiments, the display instructions may be configured to cause the input-output device system to display a monophasic intra-cardiac electrogram concurrently with the plurality of data sets, the monophasic intra-cardiac electrogram derived from at least a portion of the intra-cardiac voltage data sampled by the electrode, and the monophasic intra-cardiac electrogram reducing in amplitude with each sequential display of each of at least some of the plurality of data sets. In some embodiments, the monophasic intra-cardiac electrogram has a positive polarity.

In some embodiments, the display instructions may be configured to cause the input-output device system to display an intra-cardiac electrogram concurrently with the plurality of data sets, the intra-cardiac electrogram derived from at least a portion of the intra-cardiac voltage data sampled by the electrode. The intra-cardiac electrogram may a monophasic intra-cardiac electrogram. The monophasic intra-cardiac electrogram may have a positive polarity in some embodiments. In some embodiments, the display instructions may be configured to cause the input-output device system to display the plurality of data sets among at least a portion of the intra-cardiac electrogram.

In some embodiments, each of the plurality of data sets may include a respective one of a plurality of voltage magnitude sets. Each respective one of the plurality of voltage magnitude sets may be frequency-weighted. In some embodiments, each respective second portion of the intra-cardiac voltage data sampled by the electrode during the respective one of the plurality of cardiac cycles may include frequency-weighted data. In some embodiments, the intra-cardiac voltage data may be sampled by the electrode while positioned at a same location in an intra-cardiac cavity during each of the plurality of cardiac cycles in the period of time.

Various systems may include combinations and subsets of all the systems summarized above or otherwise described herein.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The data processing device system may be configured by the program at least to receive intra-cardiac voltage data via the input-output device system, the intra-cardiac voltage data sampled by an electrode over a period of time including a plurality of cardiac cycles. The data processing device system may be configured by the program at least to identify a respective occurrence of a particular cardiac event in each of the plurality of cardiac cycles. The data processing device system may be configured by the program at least to identify, for each respective one of the plurality of cardiac cycles, a respective first portion of the intra-cardiac voltage data sampled during the respective one of the plurality of cardiac cycles, each respective first portion of the intra-cardiac voltage data identified in accordance with a predetermined temporal relationship with the respective occurrence of the particular cardiac event identified in the respective one of the plurality of cardiac cycles. The data processing device system may be configured by the program at least to identify, for each respective one of the plurality of cardiac cycles, a particular portion of the intra-cardiac voltage data sampled during the respective one of the plurality of cardiac cycles as an excludable portion of the intra-cardiac voltage data sampled by the electrode during the respective one of the plurality of cardiac cycles, each identified excludable portion of the intra-cardiac voltage data including some but not all of the intra-cardiac voltage data sampled by the electrode during the respective one of the plurality of cardiac cycles. The data processing device system may be configured by the program at least to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified excludable portion of the intra-cardiac voltage data sampled by the electrode during the respective one of the plurality of cardiac cycles. The data processing device system may be configured by the program at least to cause the input-output device system to concurrently display the plurality of data sets.

In some embodiments, an intra-cardiac voltage data display method is executed by a data processing device system according to a program stored by a memory device system communicatively connected to the data processing device system, the data processing device system further communicatively connected to an input-output device system. The method may include receiving intra-cardiac voltage data via the input-output device system, the intra-cardiac voltage data sampled by an electrode over a period of time including a plurality of cardiac cycles. The method may include identifying a respective occurrence of a particular cardiac event in each of the plurality of cardiac cycles. The method may include identifying, for each respective one of the plurality of cardiac cycles, a respective first portion of the intra-cardiac voltage data sampled during the respective one of the plurality of cardiac cycles, each respective first portion of the intra-cardiac voltage data identified in accordance with a predetermined temporal relationship with the respective occurrence of the particular cardiac event identified in the respective one of the plurality of cardiac cycles. The method may include identifying, for each respective one of the plurality of cardiac cycles, a particular portion of the intra-cardiac voltage data sampled during the respective one of the plurality of cardiac cycles as an excludable portion of the intra-cardiac voltage data sampled by the electrode during the respective one of the plurality of cardiac cycles, each identified excludable portion of the intra-cardiac voltage data including some but not all of the intra-cardiac voltage data sampled by the electrode during the respective one of the plurality of cardiac cycles. The method may include deriving, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified excludable portion of the intra-cardiac voltage data sampled by the electrode during the respective one of the plurality of cardiac cycles. The method may include causing the input-output device system to concurrently display the plurality of data sets.

In some embodiments, a computer-readable storage medium system may be summarized as including one or more computer-readable storage mediums storing a program executable by one or more data processing devices of a data processing device system communicatively connected to an input-output device system. The program may include a data reception module configured to cause reception of intra-cardiac voltage data via the input-output device system, the intra-cardiac voltage data sampled by an electrode over a period of time including a plurality of cardiac cycles. The program may include a cardiac event identification module configured to identify a respective occurrence of a particular cardiac event in each of the plurality of cardiac cycles. The program may include a data identification module configured to identify, for each respective one of the plurality of cardiac cycles, a respective first portion of the intra-cardiac voltage data sampled during the respective one of the plurality of cardiac cycles, each respective first portion of the intra-cardiac voltage data identified in accordance with a predetermined temporal relationship with the respective occurrence of the particular cardiac event identified in the respective one of the plurality of cardiac cycles. The program may include an excludable data identification module configured to identify, for each respective one of the plurality of cardiac cycles, a particular portion of the intra-cardiac voltage data sampled during the respective one of the plurality of cardiac cycles as an excludable portion of the intra-cardiac voltage data sampled by the electrode during the respective one of the plurality of cardiac cycles, each identified excludable portion of the intra-cardiac voltage data including some but not all of the intra-cardiac voltage data sampled by the electrode during the respective one of the plurality of cardiac cycles. The program may include a data derivation module configured to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified excludable portion of the intra-cardiac voltage data sampled by the electrode during the respective one of the plurality of cardiac cycles. The program may include a display module configured to cause the input-output device system to concurrently display the plurality of data sets.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The program may include data reception instructions configured to cause reception of intra-cardiac voltage data via the input-output device system, the intra-cardiac voltage data sampled by an electrode over a period of time including a plurality of cardiac cycles. The program may include data identification instructions configured to identify, for each respective one of the plurality of cardiac cycles, a respective first portion of the intra-cardiac voltage data sampled during the respective one of the plurality of cardiac cycles, each respective first portion of the intra-cardiac voltage data identified as including a maximum absolute value of the intra-cardiac voltage data sampled by the electrode during the respective one of the plurality of cardiac cycles, each identified first portion of the intra-cardiac voltage data including some but not all of the intra-cardiac voltage data sampled by the electrode during the respective one of the plurality of cardiac cycles. The program may include data derivation instructions configured to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified first portion of the intra-cardiac voltage data sampled by the electrode during the respective one of the plurality of cardiac cycles. The program may include display instructions configured to cause the input-output device system to concurrently display the plurality of data sets.

In some embodiments, the data derivation instructions may be configured to derive each respective one of the plurality of data sets at least in part from a first respective part of the respective second portion of the intra-cardiac voltage data sampled by the electrode during the respective one of the plurality of cardiac cycles, the first respective part including a maximum value as compared with other parts of the respective second portion of the intra-cardiac voltage data sampled by the electrode during the respective one of the plurality of cardiac cycles. In some embodiments, the data derivation instructions may be configured to derive each respective one of the plurality of data sets at least in part from a second respective part of the respective second portion of the intra-cardiac voltage data sampled by the electrode during the respective one of the plurality of cardiac cycles, the second respective part including a minimum value as compared with other parts of the respective second portion of the intra-cardiac voltage data sampled by the electrode during the respective one of the plurality of cardiac cycles.

In some embodiments, each of the plurality of data sets may include data representative of a maximum absolute value in the respective second portion of the intra-cardiac voltage data sampled by the electrode during the respective one of the plurality of cardiac cycles. In some embodiments, each of the plurality of data sets may include data representative of a difference between a maximum value and a minimum value in the respective second portion of the intra-cardiac voltage data sampled by the electrode during the respective one of the plurality of cardiac cycles. In some embodiments, each of the plurality of data sets may include data representative of a difference between two values in the respective second portion of the intra-cardiac voltage data sampled by the electrode during the respective one of the plurality of cardiac cycles. In some embodiments, the program may include activation instructions configured to cause the electrode to transmit energy sufficient to cause tissue ablation at least during the sampling of the intra-cardiac voltage data by the electrode over the period of time including the plurality of cardiac cycles.

In some embodiments, the display instructions may be configured to cause the input-output device system to sequentially display each of the plurality of data sets until all of the plurality of data sets are concurrently displayed by the input-output device system. In some embodiments, the display instructions may be configured to cause the input-output device system to sequentially display each of the plurality of data sets according to a first order that is consistent with an order of the plurality of cardiac cycles during the period of time. In some embodiments, the display instructions may be configured to cause the input-output device system to display the plurality of the data sets in a first spatial order representative of an order of the plurality of cardiac cycles during the period of time. In some embodiments, the display instructions may be configured to cause the input-output device system to sequentially display each of the plurality of data sets according to a first order that is consistent with the order of the plurality of cardiac cycles during the period of time. In some embodiments, the display instructions may be configured to cause the input-output device system to display an intra-cardiac electrogram concurrently with the plurality of data sets, the intra-cardiac electrogram derived from at least a portion of the intra-cardiac voltage data sampled by the electrode, and the intra-cardiac electrogram undergoing a biphasic to monophasic transformation during at least part of the sequential display of each of the plurality of data sets. In some embodiments, the display instructions may be configured to cause the input-output device system to display a monophasic intra-cardiac electrogram concurrently with the plurality of data sets, the monophasic intra-cardiac electrogram derived from at least a portion of the intra-cardiac voltage data sampled by the electrode, and the monophasic intra-cardiac electrogram reducing in amplitude with each sequential display of each of at least some of the plurality of data sets. The monophasic intra-cardiac electrogram has a positive polarity in some embodiments.

In some embodiments, the display instructions may be configured to cause the input-output device system to display an intra-cardiac electrogram concurrently with the plurality of data sets, the intra-cardiac electrogram derived from at least a portion of the intra-cardiac voltage data sampled by the electrode. In some embodiments, the intra-cardiac electrogram is a monophasic intra-cardiac electrogram. The monophasic intra-cardiac electrogram may have a positive polarity in some embodiments. In some embodiments, the display instructions may be configured to cause the input-output device system to display the plurality of data sets among at least a portion of the intra-cardiac electrogram.

In some embodiments, each of the plurality of data sets may include a respective one of a plurality of voltage magnitude sets. In some embodiments, each respective one of the plurality of voltage magnitude sets is frequency-weighted. In some embodiments, each respective second portion of the intra-cardiac voltage data sampled by the electrode during the respective one of the plurality of cardiac cycles includes frequency-weighted data. In some embodiments, the intra-cardiac voltage data may be sampled by the electrode while positioned at a same location in an intra-cardiac cavity during each of the plurality of cardiac cycles in the period of time.

Various systems may include combinations and subsets of all the systems summarized above or otherwise described herein.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The data processing device system may be configured by the program at least to receive intra-cardiac voltage data via the input-output device system, the intra-cardiac voltage data sampled by an electrode over a period of time including a plurality of cardiac cycles. The data processing device system may be configured by the program at least to identify, for each respective one of the plurality of cardiac cycles, a respective first portion of the intra-cardiac voltage data sampled during the respective one of the plurality of cardiac cycles, each respective first portion of the intra-cardiac voltage data identified as including a maximum absolute value of the intra-cardiac voltage data sampled by the electrode during the respective one of the plurality of cardiac cycles, each identified first portion of the intra-cardiac voltage data including some but not all of the intra-cardiac voltage data sampled by the electrode during the respective one of the plurality of cardiac cycles. The data processing device system may be configured by the program at least to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified first portion of the intra-cardiac voltage data sampled by the electrode during the respective one of the plurality of cardiac cycles. The data processing device system may be configured by the program at least to cause the input-output device system to concurrently display the plurality of data sets.

In some embodiments, an intra-cardiac voltage data display method is executed by a data processing device system according to a program stored by a memory device system communicatively connected to the data processing device system, the data processing device system further communicatively connected to an input-output device system. The method may include receiving intra-cardiac voltage data via the input-output device system, the intra-cardiac voltage data sampled by an electrode over a period of time including a plurality of cardiac cycles. The method may include identifying, for each respective one of the plurality of cardiac cycles, a respective first portion of the intra-cardiac voltage data sampled during the respective one of the plurality of cardiac cycles, each respective first portion of the intra-cardiac voltage data identified as including a maximum absolute value of the intra-cardiac voltage data sampled by the electrode during the respective one of the plurality of cardiac cycles, each identified first portion of the intra-cardiac voltage data including some but not all of the intra-cardiac voltage data sampled by the electrode during the respective one of the plurality of cardiac cycles. The method may include deriving, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified first portion of the intra-cardiac voltage data sampled by the electrode during the respective one of the plurality of cardiac cycles. The method may include causing the input-output device system to concurrently display the plurality of data sets.

In some embodiments, a computer-readable storage medium system may be summarized as including one or more computer-readable storage mediums storing a program executable by one or more data processing devices of a data processing device system communicatively connected to an input-output device system. The program may include a data reception module configured to cause reception of intra-cardiac voltage data via the input-output device system, the intra-cardiac voltage data sampled by an electrode over a period of time including a plurality of cardiac cycles. The program may include a data identification module configured to identify, for each respective one of the plurality of cardiac cycles, a respective first portion of the intra-cardiac voltage data sampled during the respective one of the plurality of cardiac cycles, each respective first portion of the intra-cardiac voltage data identified as including a maximum absolute value of the intra-cardiac voltage data sampled by the electrode during the respective one of the plurality of cardiac cycles, each identified first portion of the intra-cardiac voltage data including some but not all of the intra-cardiac voltage data sampled by the electrode during the respective one of the plurality of cardiac cycles. The program may include a data derivation module configured to derive, for each respective one of the plurality of cardiac cycles, a respective one of a plurality of data sets at least in part from a respective second portion of the intra-cardiac voltage data sampled by the electrode during the respective one of the plurality of cardiac cycles, each respective one of the plurality of data sets derived only from particular data that excludes the identified first portion of the intra-cardiac voltage data sampled by the electrode during the respective one of the plurality of cardiac cycles. The program may include a display module configured to cause the input-output device system to concurrently display the plurality of data sets.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The program may include data reception instructions configured to cause reception of intra-cardiac voltage data via the input-output device system, the intra-cardiac voltage data sampled by an electrode over a period of time including a plurality of cardiac cycles that include at least a first cardiac cycle and a second cardiac cycle other than the first cardiac cycle, the second cardiac cycle occurring after the first cardiac cycle. The program may include display instructions configured to cause the input-output device system to display a plurality of data sets including a concurrently displayed first data set and a concurrently displayed second data set. The program may include data derivation instructions configured to derive the first data set at least in part from the intra-cardiac voltage data sampled by the electrode during a first time in the first cardiac cycle, and from the intra-cardiac voltage data sampled by the electrode during a second time in the first cardiac cycle, the second time occurring after the first time. The data derivation instructions may be configured to derive the second data set only from particular data, the particular data excluding at least some of the intra-cardiac voltage data sampled by the electrode during the second time in the first cardiac cycle, and the particular data including at least some of the intra-cardiac voltage data sampled by the electrode during the first time in the first cardiac cycle and at least some of the intra-cardiac voltage data sampled by the electrode during the second cardiac cycle.

In some embodiments, the data derivation instructions may be configured to derive the first data set at least in part from at least part of the intra-cardiac voltage data sampled by the electrode during the second cardiac cycle. In some embodiments, the concurrently displayed first data set may include at least a portion of an intra-cardiac electrogram. In some embodiments, the concurrently displayed first data set may include at least a portion of a monophasic intra-cardiac electrogram. The monophasic intra-cardiac electrogram may have a positive polarity in some embodiments. In some embodiments, the displayed portion of the intra-cardiac electrogram may include a particular biphasic portion of the portion of the intra-cardiac electrogram derived from at least some of the intra-cardiac voltage data sampled by the electrode during the first cardiac cycle, and a particular monophasic portion of the portion of the intra-cardiac electrogram derived from the at least part of the intra-cardiac voltage data sampled by the electrode during the second cardiac cycle. In some embodiments, the displayed portion of the intra-cardiac electrogram may include a first monophasic portion of the portion of the intra-cardiac electrogram derived from at least some of the intra-cardiac voltage data sampled by the electrode during the first cardiac cycle, and a second monophasic portion of the portion of the intra-cardiac electrogram derived from the at least part of the intra-cardiac voltage data sampled by the electrode during the second cardiac cycle. Each of the first and the second monophasic portions of the intra-cardiac electrogram may have a positive polarity in some embodiments. in some embodiments, an amplitude of the first monophasic portion of the portion of the intra-cardiac electrogram may be greater than an amplitude of the second monophasic portion of the portion of the intra-cardiac electrogram.

In some embodiments, the data derivation instructions may be configured to derive the first data set at least in part from a particular portion of the intra-cardiac voltage data sampled by the electrode during the second cardiac cycle, and the particular data may exclude the particular portion of the intra-cardiac voltage data sampled by the electrode during the second cardiac cycle. In some embodiments, the particular data may exclude a maximum absolute value of the intra-cardiac voltage data sampled by the electrode during the first cardiac cycle. In some embodiments, the particular data may exclude at least some of a portion of the intra-cardiac voltage data sampled by the electrode during an occurrence of ventricular systole in the first cardiac cycle.

In some embodiments, the concurrently displayed second data set may include data representative of a maximum absolute value of the intra-cardiac voltage data sampled by the electrode during the first time in the first cardiac cycle. In some embodiments, the concurrently displayed second data set may include data representative of a difference between two values of the intra-cardiac voltage data sampled by the electrode during the first time in the first cardiac cycle. In some embodiments, the concurrently displayed second data set may include data representative of a difference between a maximum value of the intra-cardiac voltage data sampled by the electrode during the first time in the first cardiac cycle and a minimum value of the intra-cardiac voltage data sampled by the electrode during the first time in the first cardiac cycle. In some embodiments, the concurrently displayed second data set may include data derived from (a) a minimum value of the intra-cardiac voltage data sampled by the electrode during the first time in the first cardiac cycle; (b) a maximum value of the intra-cardiac voltage data sampled by the electrode during the first time in the first cardiac cycle; or both (a) and (b). In some embodiments, the concurrently displayed second data set may include first data representative of a difference between two values of the intra-cardiac voltage data sampled by the electrode during the first cardiac cycle and second data representative of a difference between two values of the intra-cardiac voltage data sampled by the electrode during the second cardiac cycle.

In some embodiments, the program may include activation instructions configured to cause a transmission of energy sufficient for tissue ablation at least during the sampling of the intra-cardiac voltage data by the electrode during each of at least the first cardiac cycle and the second cardiac cycle. In some embodiments, the concurrently displayed first data set may include at least a portion of an intra-cardiac electrogram. In some embodiments, the program may include identification instructions configured to identify a duration from a time from a start of the tissue ablation to a time of a maximum voltage peak in at least the portion of the intra-cardiac electrogram. The program may include tissue thickness determination instructions configured to determine a thickness of tissue subject to the tissue ablation based at least upon a comparison of the identified duration with a predetermined threshold. The program may include thickness indication instructions configured to output a tissue-thickness indication via the input-output device system indicating a result of the determination of the thickness of the tissue.

In some embodiments, the program may include identification instructions configured to identify a duration from a time from a start of the tissue ablation to a time of a maximum voltage peak in at least a portion of the second data set. The program may include tissue thickness determination instructions configured to determine a thickness of tissue subject to the tissue ablation based at least upon a comparison of the identified duration with a predetermined threshold. The program may include thickness indication instructions configured to output a tissue-thickness indication via the input-output device system indicating a result of the determination of the thickness of the tissue.

In some embodiments, the program may include identification instructions configured to identify a curve-slope from a time of a maximum voltage peak in at least a portion of the second data set to a time indicating a beginning of a pre-plateau transitional region in at least the portion of the second data set. The program may include tissue thickness determination instructions configured to determine a thickness of tissue subject to the tissue ablation based at least upon a comparison of the identified curve-slope with a predetermined curve-slope. The program may include thickness indication instructions configured to output a tissue-thickness indication via the input-output device system indicating a result of the determination of the thickness of the tissue.

In some embodiments, the display instructions may be configured to cause the input-output device system to concurrently display the second data set at least by displaying (a) the data included in the second data set and derived at least in part from the at least some of the intra-cardiac voltage data sampled by the electrode during the second cardiac cycle sequentially after (b) the data included in the second data set and derived at least in part from the intra-cardiac voltage data sampled by the electrode during the first time in the first cardiac cycle while continuing to display (b) to cause both (a) and (b) to be concurrently displayed. In some embodiments, the display instructions may be configured to cause the input-output device system to display an intra-cardiac electrogram concurrently with at least the concurrently displayed second data set, the intra-cardiac electrogram derived from at least a portion of the intra-cardiac voltage data sampled by the electrode, and the intra-cardiac electrogram undergoing a biphasic to monophasic transformation during the display of the concurrently displayed second data set. In some embodiments, the display instructions may be configured to cause the input-output device system to display a monophasic intra-cardiac electrogram concurrently with at least the concurrently displayed second data set, the monophasic intra-cardiac electrogram including a plurality of portions, each portion of the monophasic intra-cardiac electrogram corresponding to a respective particular cardiac event occurring in a respective one of the plurality of cardiac cycles, the particular cardiac events being a same cardiac event, and amplitudes of the particular cardiac events, as represented in the monophasic intra-cardiac electrogram by the plurality of portions, decreasing over a span including at least the first cardiac cycle and the second cardiac cycle. Each portion of the monophasic intra-cardiac electrogram may have a positive polarity in some embodiments.

In some embodiments, the program may include cardiac event identification instructions configured to identify a respective occurrence of a particular cardiac event in each respective one of the plurality of cardiac cycles. The program may include data identification instructions configured to identify, for each respective one of the plurality of cardiac cycles, a particular portion of the intra-cardiac voltage data sampled during the respective one of the plurality of cardiac cycles, each particular portion of the intra-cardiac voltage data sampled by the electrode during the respective one of the plurality of cardiac cycles including some but not all of the intra-cardiac voltage data sampled by the electrode during the respective one of the plurality of cardiac cycles, each particular portion of the intra-cardiac voltage data identified in accordance with a predetermined temporal relationship with the occurrence of the particular cardiac event identified in the respective one of the plurality of cardiac cycles. The particular data may exclude at least some of each identified particular portion of the intra-cardiac voltage data sampled by the electrode during the respective one of the first cardiac cycle and the second cardiac cycle.

In some embodiments, the display instructions may be configured to cause the input-output device system to concurrently display the concurrently displayed first data set and the concurrently displayed second data set. In some embodiments, the display instructions may be configured to cause the input-output device system to display the concurrently displayed first data set and the concurrently displayed second data set in a superimposed configuration.

In some embodiments, each of the plurality of data sets may include a respective one of a plurality of voltage magnitude sets. In some embodiments, each respective one of the plurality of voltage magnitude sets may be frequency-weighted.

Various systems may include combinations and subsets of all the systems summarized above or otherwise described herein.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The data processing device system may be configured by the program at least to receive intra-cardiac voltage data via the input-output device system, the intra-cardiac voltage data sampled by an electrode over a period of time including a plurality of cardiac cycles that include at least a first cardiac cycle and a second cardiac cycle other than the first cardiac cycle, the second cardiac cycle occurring after the first cardiac cycle. The data processing device system may be configured by the program at least to cause the input-output device system to display a plurality of data sets including a concurrently displayed first data set and a concurrently displayed second data set. The data processing device system may be configured by the program at least to derive the first data set at least in part from the intra-cardiac voltage data sampled by the electrode during a first time in the first cardiac cycle, and from the intra-cardiac voltage data sampled by the electrode during a second time in the first cardiac cycle, the second time occurring after the first time. The data processing device system may be configured by the program at least to derive the second data set only from particular data, the particular data excluding at least some of the intra-cardiac voltage data sampled by the electrode during the second time in the first cardiac cycle, and the particular data including at least some of the intra-cardiac voltage data sampled by the electrode during the first time in the first cardiac cycle and at least some of the intra-cardiac voltage data sampled by the electrode during the second cardiac cycle.

In some embodiments, an intra-cardiac voltage data display method is executed by a data processing device system according to a program stored by a memory device system communicatively connected to the data processing device system, the data processing device system further communicatively connected to an input-output device system. The method may include receiving intra-cardiac voltage data via the input-output device system, the intra-cardiac voltage data sampled by an electrode over a period of time including a plurality of cardiac cycles that include at least a first cardiac cycle and a second cardiac cycle other than the first cardiac cycle, the second cardiac cycle occurring after the first cardiac cycle. The method may include causing the input-output device system to display a plurality of data sets including a concurrently displayed first data set and a concurrently displayed second data set. The method may include deriving the first data set at least in part from the intra-cardiac voltage data sampled by the electrode during a first time in the first cardiac cycle, and from the intra-cardiac voltage data sampled by the electrode during a second time in the first cardiac cycle, the second time occurring after the first time. The method may include deriving the second data set only from particular data, the particular data excluding at least some of the intra-cardiac voltage data sampled by the electrode during the second time in the first cardiac cycle, and the particular data including at least some of the intra-cardiac voltage data sampled by the electrode during the first time in the first cardiac cycle and at least some of the intra-cardiac voltage data sampled by the electrode during the second cardiac cycle.

In some embodiments, a computer-readable storage medium system may be summarized as including one or more computer-readable storage mediums storing a program executable by one or more data processing devices of a data processing device system communicatively connected to an input-output device system. The program may include a data reception module configured to cause reception of intra-cardiac voltage data via the input-output device system, the intra-cardiac voltage data sampled by an electrode over a period of time including a plurality of cardiac cycles that include at least a first cardiac cycle and a second cardiac cycle other than the first cardiac cycle, the second cardiac cycle occurring after the first cardiac cycle. The program may include a display module configured to cause the input-output device system to display a plurality of data sets including a concurrently displayed first data set and a concurrently displayed second data set. The program may include a data derivation module configured to derive the first data set at least in part from the intra-cardiac voltage data sampled by the electrode during a first time in the first cardiac cycle, and from the intra-cardiac voltage data sampled by the electrode during a second time in the first cardiac cycle, the second time occurring after the first time. The data derivation module may be configured to derive the second data set only from particular data, the particular data excluding at least some of the intra-cardiac voltage data sampled by the electrode during the second time in the first cardiac cycle, and the particular data including at least some of the intra-cardiac voltage data sampled by the electrode during the first time in the first cardiac cycle and at least some of the intra-cardiac voltage data sampled by the electrode during the second cardiac cycle.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The program may include data reception instructions configured to cause reception of intra-cardiac voltage data via the input-output device system, the intra-cardiac voltage data sampled by an electrode over a period of time that includes a plurality of cardiac cycles. The program may include data derivation instructions configured to derive at least a first graphical distribution of data derived at least in part from a first portion of the received intra-cardiac voltage data and a second graphical distribution of data derived at least in part from a second portion of the received intra-cardiac voltage data. The program may include display instructions configured to cause the input-output device system to concurrently display at least the first graphical distribution of data and the second graphical distribution of data, the displayed first graphical distribution including first data displayed across a first time scale and the displayed second graphical distribution including second data displayed across a second time scale having a different scale than the first time scale, the displayed first and second displayed graphical distributions concurrently displayed in a superimposed configuration.

In some embodiments, the data derivation instructions may be configured to derive the second graphical distribution of data only from particular data, the particular data excluding, for each respective one of at least three of the plurality of cardiac cycles, a respective particular part of the intra-cardiac voltage data sampled by the electrode during the respective one of the at least three of the plurality of cardiac cycles, each respective particular part including some but not all of the intra-cardiac voltage data sampled by the electrode during the respective one of the at least three of the plurality of cardiac cycles, and wherein the data derivation instructions are configured to derive the first graphical distribution of data from data that includes each of the respective particular parts.

In some embodiments, the program may include cardiac event identification instructions configured to identify a respective occurrence of a particular cardiac event in each respective one of the at least three of the plurality of cardiac cycles. The data identification instructions may be configured to identify, for each respective one of the at least three of the plurality of cardiac cycles, a particular portion of the intra-cardiac voltage data sampled during the respective one of the at least three of the plurality of cardiac cycles, each particular portion of the intra-cardiac voltage data sampled by the electrode during the respective one of the at least three of the plurality of cardiac cycles including some but not all of the intra-cardiac voltage data sampled by the electrode during the respective one of the at least three of the plurality of cardiac cycles, each particular portion of the intra-cardiac voltage data identified in accordance with a predetermined temporal relationship with the occurrence of the particular cardiac event identified in the respective one of the at least three of the plurality of cardiac cycles. The particular data may exclude at least some of each identified particular portion of the intra-cardiac voltage data sampled by the electrode during the respective one of the at least three of the plurality of cardiac cycles. In some embodiments, the data derivation instructions may be configured to derive the first graphical distribution of data from the respective particular portions.

In some embodiments, the displayed first graphical distribution may include a first group of voltage magnitudes displayed across the first time scale, and the displayed second graphical distribution may include a second group of voltage magnitudes displayed across the second time scale. In some embodiments, (a) the first group of voltage magnitudes (b) the second group of voltage magnitudes, or each of (a) and (b) is frequency-weighted.

Various systems may include combinations and subsets of all the systems summarized above or otherwise described herein.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The data processing device system may be configured by the program at least to receive intra-cardiac voltage data via the input-output device system, the intra-cardiac voltage data sampled by an electrode over a period of time that includes a plurality of cardiac cycles. The data processing device system may be configured by the program at least to derive at least a first graphical distribution of data derived at least in part from a first portion of the received intra-cardiac voltage data and a second graphical distribution of data derived at least in part from a second portion of the received intra-cardiac voltage data. The data processing device system may be configured by the program at least to cause the input-output device system to concurrently display at least the first graphical distribution of data and the second graphical distribution of data, the displayed first graphical distribution including first data displayed across a first time scale and the displayed second graphical distribution including second data displayed across a second time scale having a different scale than the first time scale, the displayed first and second displayed graphical distributions concurrently displayed in a superimposed configuration.

In some embodiments, an intra-cardiac voltage data display method is executed by a data processing device system according to a program stored by a memory device system communicatively connected to the data processing device system, the data processing device system further communicatively connected to an input-output device system. The method may include receiving intra-cardiac voltage data via the input-output device system, the intra-cardiac voltage data sampled by an electrode over a period of time that includes a plurality of cardiac cycles. The method may include deriving at least a first graphical distribution of data derived at least in part from a first portion of the received intra-cardiac voltage data and a second graphical distribution of data derived at least in part from a second portion of the received intra-cardiac voltage data. The method may include causing the input-output device system to concurrently display at least the first graphical distribution of data and the second graphical distribution of data, the displayed first graphical distribution including first data displayed across a first time scale and the displayed second graphical distribution including second data displayed across a second time scale having a different scale than the first time scale, the displayed first and second displayed graphical distributions concurrently displayed in a superimposed configuration.

In some embodiments, a computer-readable storage medium system may be summarized as including one or more computer-readable storage mediums storing a program executable by one or more data processing devices of a data processing device system communicatively connected to an input-output device system. The program may include a data reception module configured to cause reception of intra-cardiac voltage data via the input-output device system, the intra-cardiac voltage data sampled by an electrode over a period of time that includes a plurality of cardiac cycles. The program may include a data derivation module configured to derive at least a first graphical distribution of data derived at least in part from a first portion of the received intra-cardiac voltage data and a second graphical distribution of data derived at least in part from a second portion of the received intra-cardiac voltage data. The program may include a display module configured to cause the input-output device system to concurrently display at least the first graphical distribution of data and the second graphical distribution of data, the displayed first graphical distribution including first data displayed across a first time scale and the displayed second graphical distribution including second data displayed across a second time scale having a different scale than the first time scale, the displayed first and second displayed graphical distributions concurrently displayed in a superimposed configuration.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The program may include data reception instructions configured to cause reception of intra-cardiac voltage data via the input-output device system, the intra-cardiac voltage data sampled by a sensing electrode over a period of time that includes a plurality of cardiac cycles. The program may include activation instructions configured to cause an ablation electrode to transmit energy sufficient for tissue ablation at least during the sampling of the intra-cardiac voltage data by the sensing electrode. The program may include data derivation instructions configured to derive at least a plurality of voltage values, each of the plurality of voltage values derived at least in part from a respective portion of the received intra-cardiac voltage data, each of the plurality of voltage values correlated with a respective time within a time range during which the respective portion of the of the received intra-cardiac voltage data was sampled by the sensing electrode. The program may include identification instructions configured to identify a duration from a time of a start of the tissue ablation to the respective time correlated with a particular one of the respective voltage values, the particular one of the respective voltage values being a maximum value as compared with others of the plurality of voltage values. The program may include tissue thickness determination instructions configured to determine a thickness of tissue subject to the tissue ablation based at least upon a comparison of the identified duration with a predetermined threshold. The program may include thickness indication instructions configured to output a tissue-thickness indication via the input-output device system indicating a result of the determination of the thickness of the tissue.

In some embodiments, each respective portion of the received intra-cardiac voltage data includes intra-cardiac voltage data sampled by the sensing electrode during a respective one of the plurality of cardiac cycles, but does not include any intra-cardiac voltage data sampled by the sensing electrode during any of the plurality of cardiac cycles other than the respective one of the plurality of cardiac cycles, and wherein each respective portion from which a respective one of at least three of the plurality of voltage values is derived represents some, but not all, of the intra-cardiac voltage data sampled by the sensing electrode during the respective one of the plurality of cardiac cycles. In some embodiments, the respective portions from which the at least three of the plurality of voltage values are derived from an interrupted sequence of the sampled intra-cardiac voltage data in which each succeeding one of the respective portions from which the at least three of the plurality of voltage values are derived is separated from an immediately preceding one of the respective portions from which the at least three of the plurality of voltage values are derived by respective portion of the sampled intra-cardiac data which does not form part of any of the respective portions from which the at least three of the plurality of voltage values is derived from. In some embodiments, the program may include cardiac event identification instructions configured to identify a respective occurrence of a particular cardiac event in each respective one of the at least three of the plurality of cardiac cycles, and each respective portion from which a respective one of at least three of the plurality of voltage values is derived is determined in accordance with a predetermined temporal relationship with the occurrence of the particular cardiac event identified in the respective one of the at least three of the plurality of cardiac cycles.

In some embodiments, the program may include display instructions configured to display, via the input-output device system, the plurality of voltage values. In some embodiments, the program may include display instructions configured to display, via the input-output device system, a distribution of the plurality of voltage values across a time scale. In some embodiments, the display instructions are configured to display, via the input-output device system, an intra-cardiac electrogram derived from the intra-cardiac voltage data sampled by the sensing electrode, the displayed intra-cardiac electrogram concurrently displayed with at least part of the distribution according to the display instructions and including a visual characteristic set visually distinct from a visual characteristic set comprised by the displayed at least part of the distribution.

In some embodiments, the program may include display instructions configured to display the plurality of voltage values as an intra-cardiac electrogram. In some embodiments, the ablation electrode is provided by the sensing electrode.

Various systems may include combinations and subsets of all the systems summarized above or otherwise described herein.

In some embodiments, an intra-cardiac voltage data display system may be summarized as including a data processing device system, an input-output device system communicatively connected to the data processing device system, and a memory device system communicatively connected to the data processing device system and storing a program executable by the data processing device system. The data processing device system may be configured by the program at least to receive intra-cardiac voltage data via the input-output device system, the intra-cardiac voltage data sampled by a sensing electrode over a period of time that includes a plurality of cardiac cycles. The data processing device system may be configured by the program at least to cause an ablation electrode to transmit energy sufficient for tissue ablation at least during the sampling of the intra-cardiac voltage data by the sensing electrode. The data processing device system may be configured by the program at least to derive at least a plurality of voltage values, each of the plurality of voltage values derived at least in part from a respective portion of the received intra-cardiac voltage data, each of the plurality of voltage values correlated with a respective time within a time range during which the respective portion of the of the received intra-cardiac voltage data was sampled by the sensing electrode. The data processing device system may be configured by the program at least to identify a duration from a time of a start of the tissue ablation to the respective time correlated with a particular one of the respective voltage values, the particular one of the respective voltage values being a maximum value as compared with others of the plurality of voltage values. The data processing device system may be configured by the program at least to determine a thickness of tissue subject to the tissue ablation based at least upon a comparison of the identified duration with a predetermined threshold. The data processing device system may be configured by the program at least to output a tissue-thickness indication via the input-output device system indicating a result of the determination of the thickness of the tissue.

In some embodiments, an intra-cardiac voltage data display method is executed by a data processing device system according to a program stored by a memory device system communicatively connected to the data processing device system, the data processing device system further communicatively connected to an input-output device system. The method may include receiving intra-cardiac voltage data via the input-output device system, the intra-cardiac voltage data sampled by a sensing electrode over a period of time that includes a plurality of cardiac cycles. The method may include causing an ablation electrode to transmit energy sufficient for tissue ablation at least during the sampling of the intra-cardiac voltage data by the sensing electrode. The method may include deriving at least a plurality of voltage values, each of the plurality of voltage values derived at least in part from a respective portion of the received intra-cardiac voltage data, each of the plurality of voltage values correlated with a respective time within a time range during which the respective portion of the of the received intra-cardiac voltage data was sampled by the sensing electrode. The method may include identifying a duration from a time of a start of the tissue ablation to the respective time correlated with a particular one of the respective voltage values, the particular one of the respective voltage values being a maximum value as compared with others of the plurality of voltage values. The method may include determining a thickness of tissue subject to the tissue ablation based at least upon a comparison of the identified duration with a predetermined threshold. The method may include outputting a tissue-thickness indication via the input-output device system indicating a result of the determination of the thickness of the tissue.

In some embodiments, a computer-readable storage medium system may be summarized as including one or more computer-readable storage mediums storing a program executable by one or more data processing devices of a data processing device system communicatively connected to an input-output device system. The program may include a data reception module configured to cause reception of intra-cardiac voltage data via the input-output device system, the intra-cardiac voltage data sampled by a sensing electrode over a period of time that includes a plurality of cardiac cycles. The program may include an activation module configured to cause an ablation electrode to transmit energy sufficient for tissue ablation at least during the sampling of the intra-cardiac voltage data by the sensing electrode. The program may include a data derivation module configured to derive at least a plurality of voltage values, each of the plurality of voltage values derived at least in part from a respective portion of the received intra-cardiac voltage data, each of the plurality of voltage values correlated with a respective time within a time range during which the respective portion of the of the received intra-cardiac voltage data was sampled by the sensing electrode. The program may include an identification module configured to identify a duration from a time of a start of the tissue ablation to the respective time correlated with a particular one of the respective voltage values, the particular one of the respective voltage values being a maximum value as compared with others of the plurality of voltage values. The program may include a tissue thickness determination module configured to determine a thickness of tissue subject to the tissue ablation based at least upon a comparison of the identified duration with a predetermined threshold. The program may include a thickness indication module configured to output a tissue-thickness indication via the input-output device system indicating a result of the determination of the thickness of the tissue.

Any of the features of any of the methods discussed herein may be combined with any of the other features of any of the methods discussed herein. In addition, a computer program product may be provided that comprises program code portions for performing some or all of any of the methods and associated features thereof described herein, when the computer program product is executed by a computer or other computing device or device system. Such a computer program product may be stored on one or more computer-readable storage mediums.

In some embodiments, each of any or all of the computer-readable storage mediums or medium systems described herein is a non-transitory computer-readable storage medium or medium system including one or more non-transitory computer-readable storage mediums storing the respective program(s).

Further, any or all of the methods and associated features thereof discussed herein may be implemented by all or part of a device system or apparatus, such as any of those described herein.

BRIEF DESCRIPTION OF THE DRAWINGS

It is to be understood that the attached drawings are for purposes of illustrating aspects of various embodiments and may include elements that are not to scale.

FIGS. 6A-6F include respective data generation and flow diagrams, which may implement various embodiments of a method by way of associated computer-executable instructions, according to some example embodiments.

DETAILED DESCRIPTION

Figure 1:
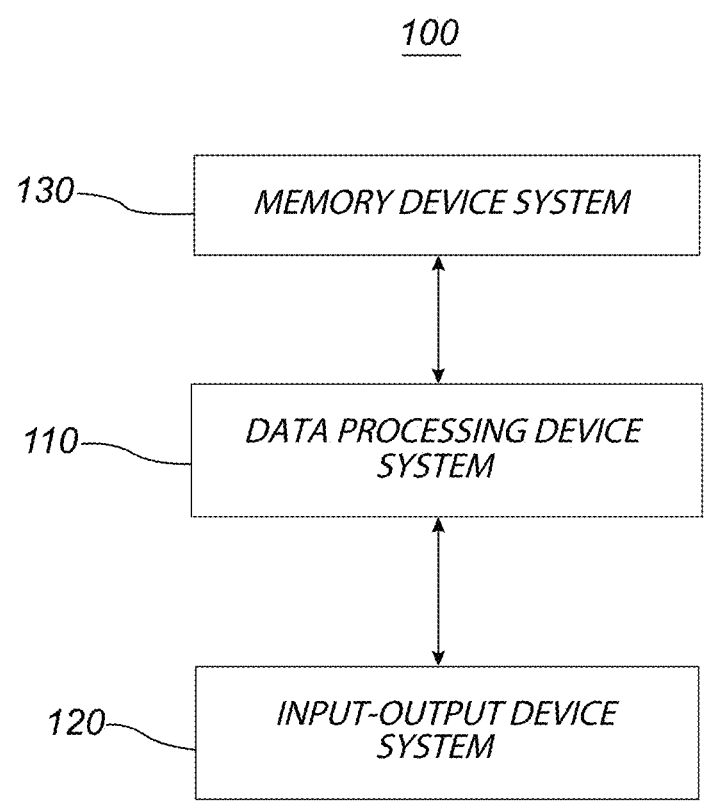
FIG. 1 includes a schematic representation of an intra-cardiac voltage display system according to various example embodiments, the intra-cardiac voltage display system including a data processing device system, an input-output device system, and a memory device system.

In the following description, certain specific details are set forth in order to provide a thorough understanding of various embodiments of the invention. However, one skilled in the art will understand that the invention may be practiced at a more general level without these details. In other instances, well-known structures have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily all referring to one embodiment or a same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase, "activation of at least transducer A" includes activation of transducer A by itself, as well as activation of transducer A and activation of one or more other additional elements besides transducer A. In the same manner, the phrase, "activation of transducer A" includes activation of transducer A by itself, as well as activation of transducer A and activation of one or more other additional elements besides transducer A. However, the phrase, "activation of only transducer A" includes only activation of transducer A, and excludes activation of any other transducers besides transducer A.

The word "ablation" as used in this disclosure should be understood to include any disruption to certain properties of tissue. Most commonly, the disruption is to the electrical conductivity and is achieved by transferring thermal energy, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity or chamber provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue can refer to a tissue having fluidic properties (e.g., blood) and may be referred to as fluidic tissue.

The term "transducer" as used in this disclosure should be interpreted broadly as any device capable of distinguishing between fluid and tissue, sensing temperature, creating heat, ablating tissue, sensing, sampling or measuring electrical activity of a tissue surface (e.g., sensing, sampling or measuring intra-cardiac electrograms, or sensing, sampling or measuring intra-cardiac voltage data), stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions may include, but are not limited to, tissue ablation, sensing, sampling or measuring electro-physiological activity (e.g., sensing, sampling or measuring intra-cardiac electrogram information or sensing, sampling or measuring intra-cardiac voltage data), sensing, sampling or measuring temperature and sensing, sampling or measuring electrical characteristics (e.g., tissue impedance or tissue conductivity). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer causes a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such a controller system or data processing device system, in order to cause the system to perform one or more operations. The set of instructions or modules can be stored by any kind of memory device, such as those described subsequently with respect to the memory device system 130 or 330 shown in FIGS. 1 and 3, respectively. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions. In some instances, this disclosure describes that the instructions or modules of a program perform a function. Such descriptions should be deemed to be equivalent to describing that the instructions or modules are configured to cause the performance of the function.

Each of the phrases "derived from" or "derivation of" or "derivation thereof" or the like is intended to mean to come from at least some part of a source, be created from at least some part of a source, or be developed as a result of a process in which at least some part of a source forms an input. For example, a data set derived from some particular portion of data may include at least some part of the particular portion of data, or may be created from at least part of the particular portion of data, or may be developed in response to a data manipulation process in which at least part of the particular portion of data forms an input. In some embodiments, a data set may be derived from a subset of the particular portion of data. In some embodiments, the particular portion of data is analyzed to identify a particular subset of the particular portion of data, and a data set is derived from the subset. In various ones of these embodiments, the subset may include some, but not all, of the particular portion of data. In some embodiments, changes in least one part of a particular portion of data may result in changes in a data set derived at least in part from the particular portion of data.

In this regard, each of the phrases "derived from" or "derivation of" or "derivation thereof" or the like is used herein at times merely to emphasize the possibility that such data or information may be modified or subject to one or more operations. For example, if a device generates first data for display, the process of converting the generated first data into a format capable of being displayed may alter the first data. This altered form of the first data may be considered a derivative or derivation of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative or derivation of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derived from" or "derivation of" or "derivation thereof" or the like is used in reference to the information or data. As indicated above, usage of the phrase "derived from" or "derivation of" or "derivation thereof" or the like merely emphasizes the possibility of such changes. Accordingly, the addition of or deletion of the phrase "derived from" or "derivation of" or "derivation thereof" or the like should have no impact on the interpretation of the respective data or information. For example, the above-discussed color-coded bar chart may be considered a derivative of the respective first data or may be considered the respective first data itself.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, this disclosure sometimes refers to a "catheter device", but such catheter device could equivalently be referred to as a "catheter device system". The word "device" may equivalently be referred to as a "device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" may be is used in this disclosure. For example, this phrase might be used in the following context, where an event A occurs in response to the occurrence of an event B. In this regard, such phrase can include, for example, that at least the occurrence of the event B causes or triggers the event A.

Further, the phrase "graphical representation" used herein is intended to include a visual representation presented via a display device and may include computer-generated text, graphics, animations, or one or more combinations thereof, which may include one or more visual representations originally generated, at least in part, by an image-capture device, such as fluoroscopy images, CT scan images, MRI images, etc.

Further still, example methods are described herein with respect to FIG. 6. Such figures are described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in each of the method figures herein is not limited to an actual structure of any program or set of instructions or required ordering of method tasks, and such method figures, according to some embodiments, merely illustrate the tasks that instructions are configured to perform, for example upon execution by a data processing device system in conjunction with interactions with one or more other devices or device systems.

FIG. 1 schematically illustrates an intra-cardiac voltage display system 100 that may be employed to at least select, control, activate, or monitor a function or activation of one or more transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, the methods of various embodiments, including the example methods of FIG. 6 described herein. Each of the phrases "data processing device", "data processor", "processor", and "computer" is intended to include any data processing device, such as a central processing unit (CPU), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods of various embodiments, including the example methods of FIG. 6 described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 can be considered a non-transitory computer-readable storage medium system.

The phrase "communicatively connected" is intended to include any type of connection, whether wired or wireless, between devices, data processors, or programs between which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system 120 may include a user-activatable control system that is responsive to a user action. The user-activatable control system may include at least one control element that may be activated or deactivated on the basis of a particular user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion a transducer-based device system. The phrase "transducer-based device system" is intended to include one or more physical systems that include various transducers. The phrase "transducer-based device" is intended to include one or more physical devices that include various transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system 120 may include various other devices or systems described in various embodiments. In some embodiments, the input-output device system 120 may include one or more display devices that display one or more of the graphical interfaces of FIGS. 5, described below.

Various embodiments of transducer-based devices are described herein. Some of the described devices are medical devices that are percutaneously or intravascularly deployed. Some of the described devices are moveable between a delivery or unexpanded configuration (e.g., FIGS. 3A, 3B discussed below) in which a portion of the device is sized for passage through a bodily opening leading to a bodily cavity, and an expanded or deployed configuration (e.g., FIGS. 3C, 3D discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to map the cavity, for example using positions of openings or ports into and out of the cavity to determine a position or orientation (e.g., pose), or both of the portion of the device in the bodily cavity. In some example embodiments, the described devices are capable of ablating tissue in a desired pattern within the bodily cavity.

In some example embodiments, the devices are capable of sensing various cardiac functions (e.g., electrophysiological activity including intra-cardiac voltages). In some example embodiments, the devices are capable of providing stimulation (e.g., electrical stimulation) to tissue within the bodily cavity. Electrical stimulation may include pacing.

Figure 2:
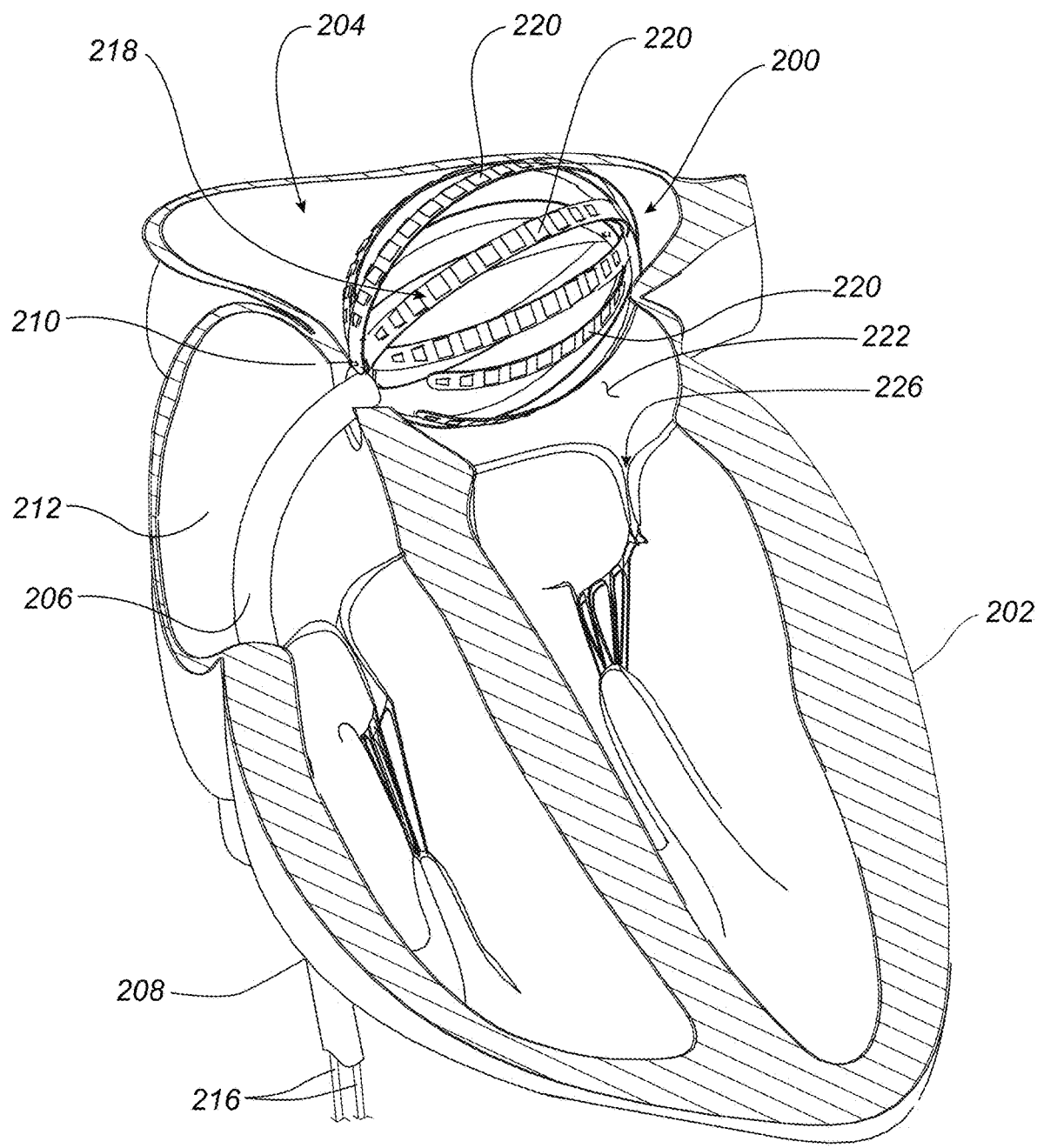
FIG. 2 includes a cutaway diagram of a heart showing a structure of a transducer-based device percutaneously placed in a left atrium of the heart according to various example embodiments.

FIG. 2 is a representation of a transducer-based device 200 useful in investigating or treating a bodily organ, for example a heart 202, according to one example embodiment.

Transducer-based device 200 can be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in some embodiments). Electrical conductors 216 provide electrical connections to transducer-based device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In some embodiments, at least some of the transducers 220 are used to sense a physical characteristic of a fluid (e.g., blood) or tissue 222, or both, that may be used to determine a position or orientation (e.g., pose), or both, of a portion of a device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern around the bodily openings, ports or pulmonary vein ostia, for instance to reduce or eliminate the occurrence of atrial fibrillation. In some embodiments, at least some of the transducers 220 are used to ablate cardiac tissue. In some embodiments, at least some of the transducers 220 are used to sense or sample intra-cardiac voltage data or sense or sample intra-cardiac electrogram data. In some embodiments, at least some of the transducers 220 are used to sense or sample intra-cardiac voltage data or sense or sample intra-cardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intra-cardiac voltage data or intra-cardiac electrogram data at a location at least proximate to a tissue location ablated by at least a second one of the transducers 220. In some embodiments, the first one of the transducers 220 is other than the second one of the transducers 220.

Figure 3A:
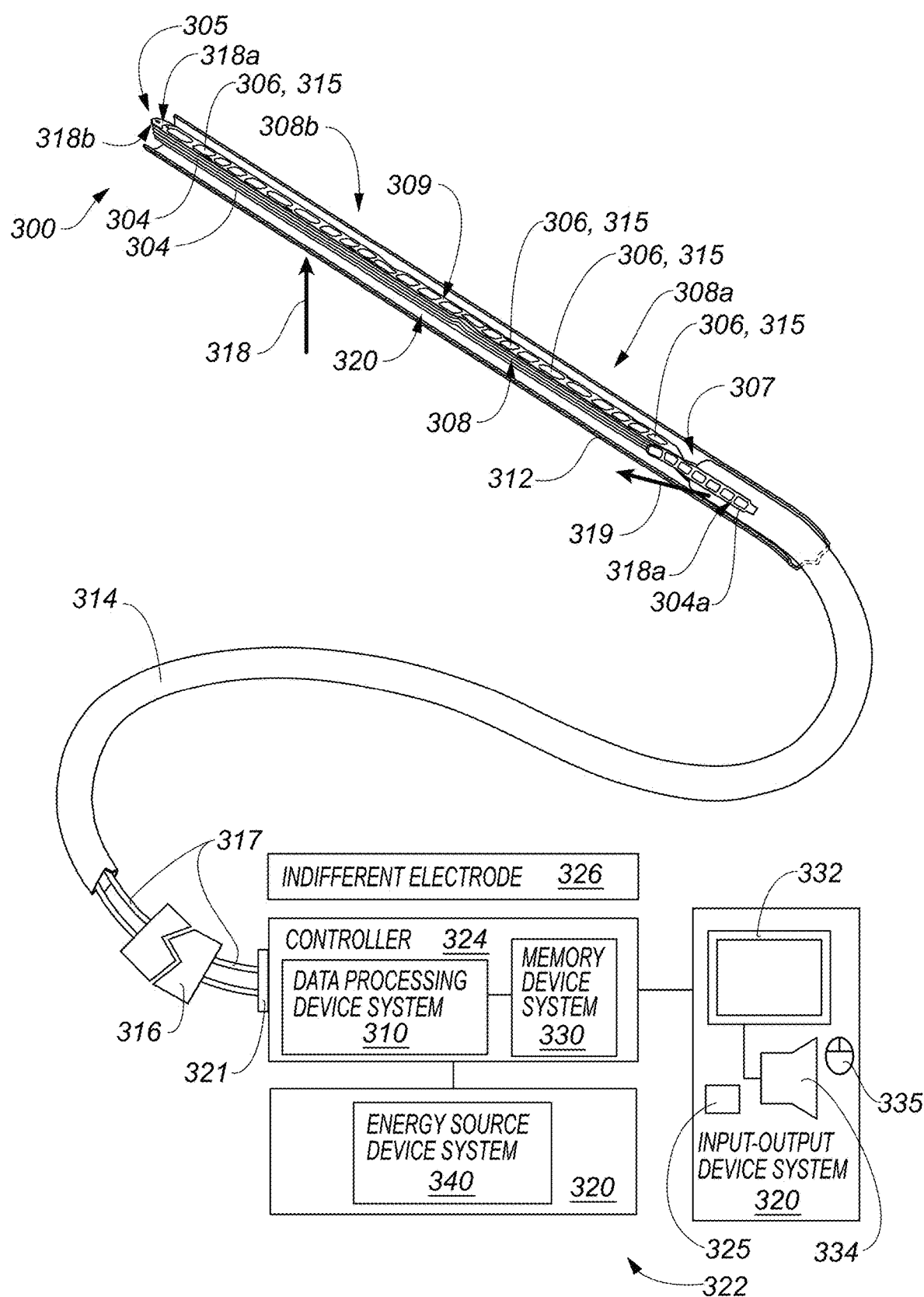
FIG. 3A includes a partially schematic representation of a medical system according to various example embodiments, the medical system representing at least a particular implementation of the intra-cardiac voltage display system of FIG. 1, and the medical system including a structure of a transducer-based device shown in a delivery or unexpanded configuration, according to some embodiments.
Figure 3B:
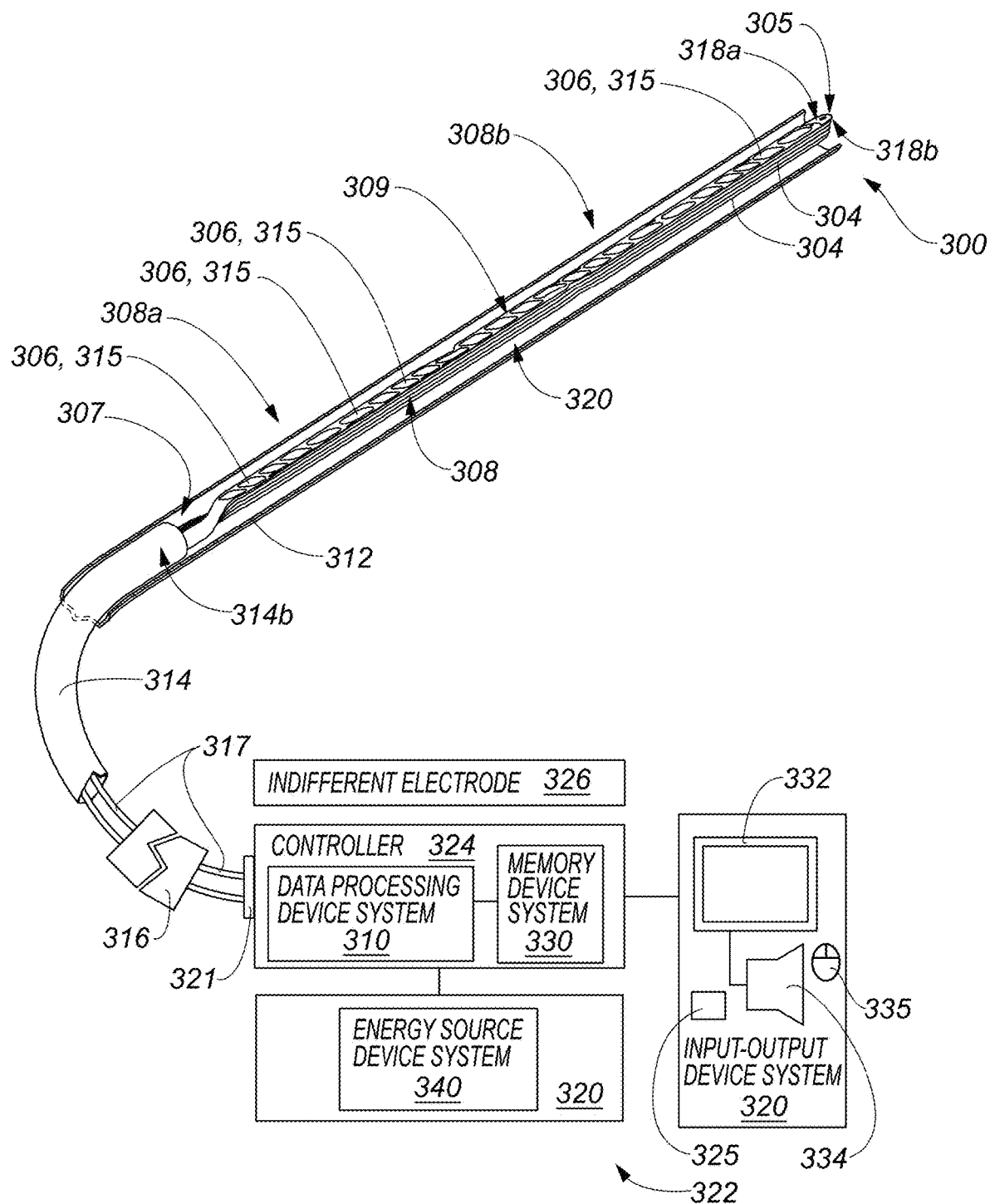
FIG. 3B includes a different viewing direction of the structure of the transducer-based device of FIG. 3A, according to some embodiments.
Figure 3C:
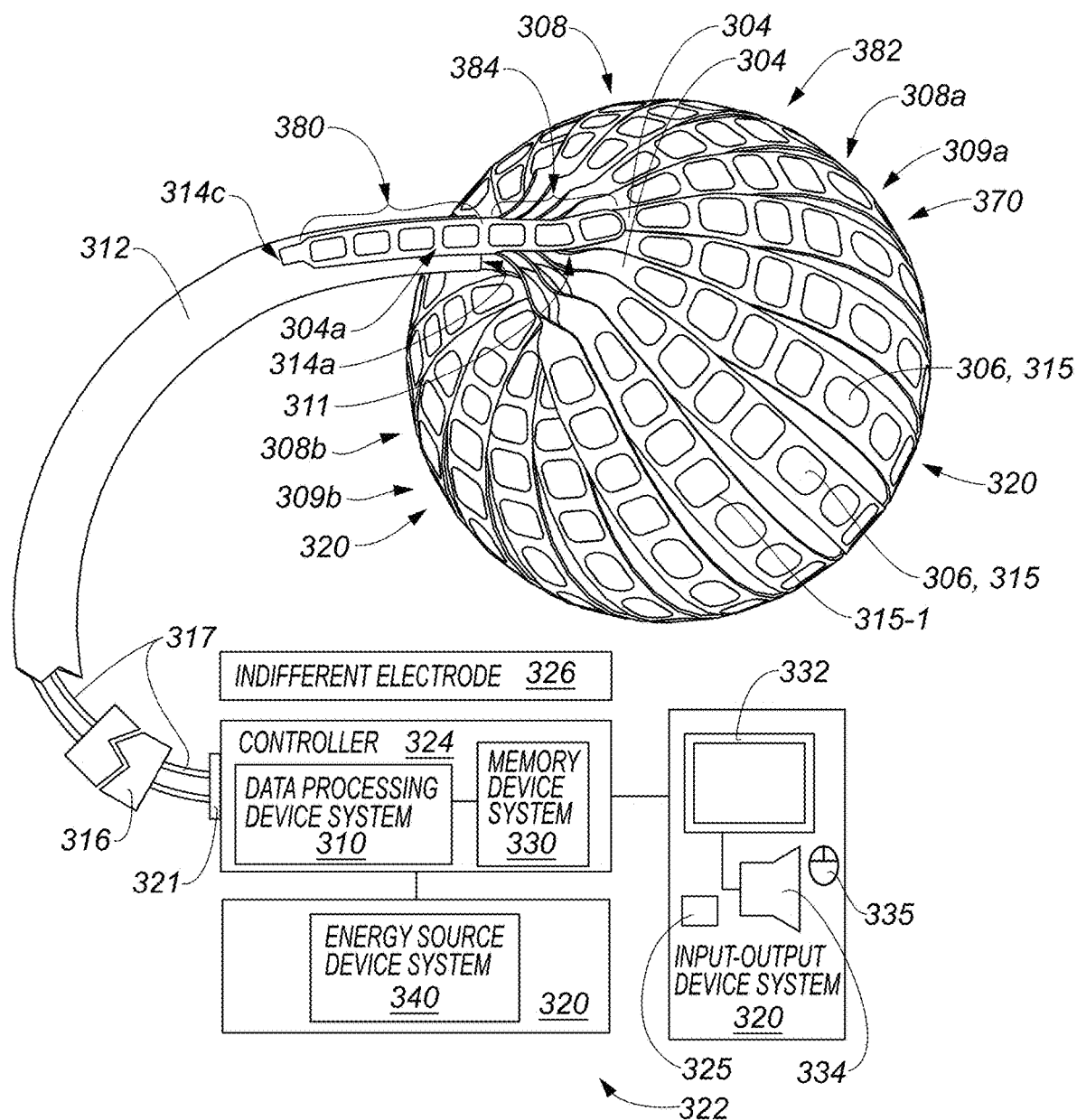
FIG. 3C includes a representation of the structure of the transducer-based device of FIGS. 3A and 3B in a deployed or expanded configuration, according to some embodiments.
Figure 3D:
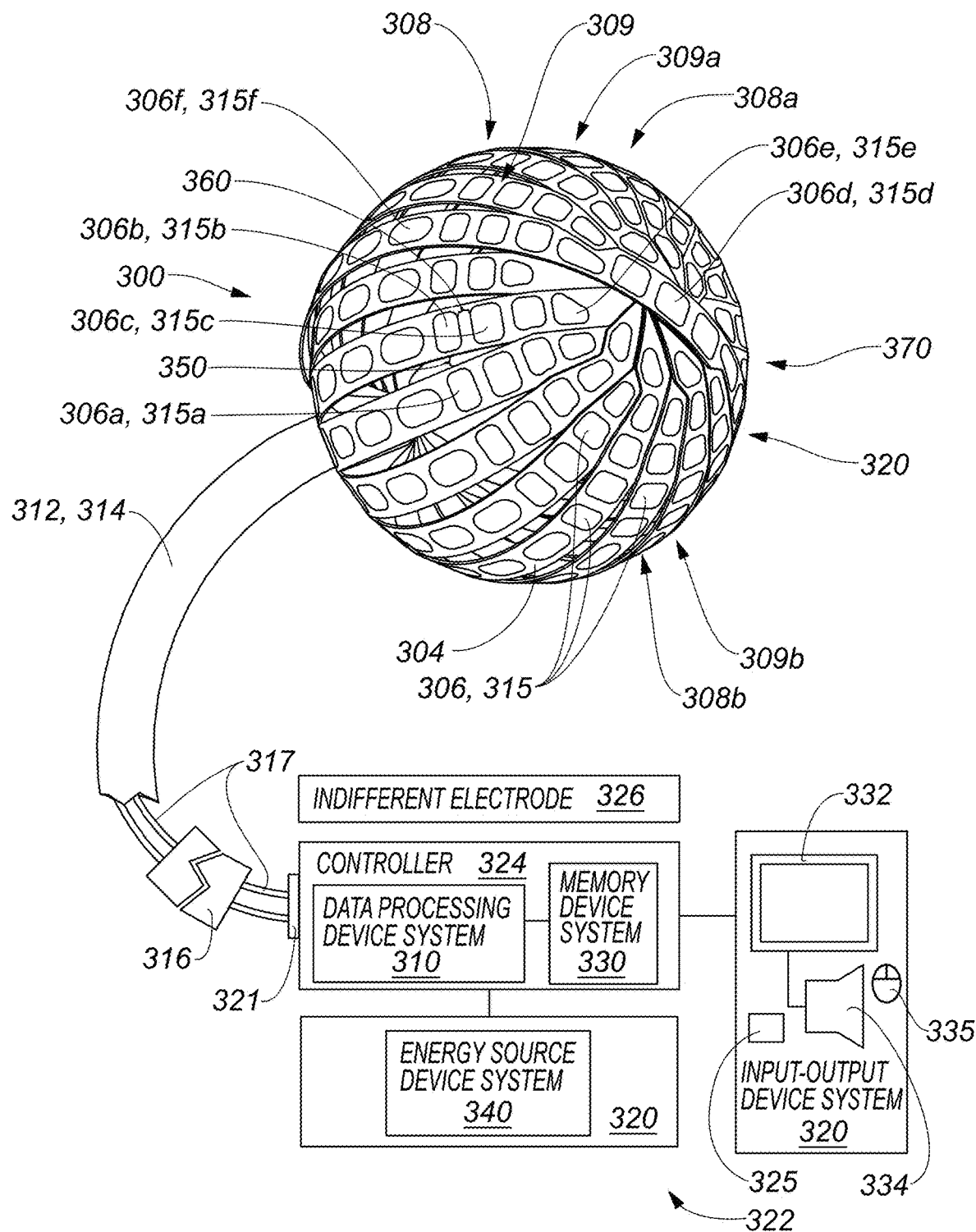
FIG. 3D includes a different viewing direction of the structure of the transducer-based device of FIG. 3C, according to some embodiments.

FIGS. 3A, 3B, 3C and 3D (collectively, FIG. 3) include a transducer-based device system (e.g., a portion thereof shown schematically) that includes a transducer-based device 300 according to one illustrated embodiment. Transducer-based device 300 includes a plurality of elongate members 304 (not all of the elongate members called out in each of FIGS. 3A, 3B, 3C and 3D) and a plurality of transducers 306 (not all of the transducers called out in FIG. 3) (some of the transducers 306 called out in FIG. 3D as 306a, 306b, 306c, 306d, 306e and 306f). FIG. 3B includes a representation of a portion of the transducer-based device 300 shown in FIG. 3A but as viewed from a different viewing direction. FIG. 3D includes a representation of a portion of the transducer-based device 300 shown in FIG. 3C but as viewed from a different viewing direction. It is noted that for clarity of illustration, all the elongate members shown in FIGS. 3C and 3D are not represented in FIGS. 3A and 3B. As will become apparent, the plurality of transducers 306 is positionable within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arranged to form a two- or three-dimensional distribution, grid or array of the transducers capable of mapping, ablating or stimulating an inside surface of a bodily cavity or lumen without requiring mechanical scanning. As shown, for example, in FIGS. 3A and 3B, the plurality of transducers 306 are arranged in a distribution receivable in a bodily cavity (not shown). In various ones of the FIGS. 3, each of at least some of transducers 306 includes a respective electrode 315 (not all of the electrode 315 called out in each of the FIGS. 3, some of the electrodes in FIG. 3D called out as 315a, 315b, 315c, 315d, 315e and 315f).

The elongate members 304 are arranged in a frame or structure 308 that is selectively movable between an unexpanded or delivery configuration (e.g., as shown in FIGS. 3A, 3B) and an expanded or deployed configuration (e.g., as shown in FIGS. 3C, 3D) that may be used to position elongate members 304 against a tissue surface within the bodily cavity or position the elongate members 304 in the vicinity of the tissue surface. In some embodiments, structure 308 has a size in the unexpanded or delivery configuration suitable for delivery through a bodily opening (e.g., via catheter sheath 312) to the bodily cavity. In various embodiments, catheter sheath 312 typically includes a length sufficient to allow the catheter sheath to extend between a location at least proximate a bodily cavity into which the structure 308 is to be delivered and a location outside a body comprising the bodily cavity. In some embodiments, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit). The elongate members 304 can include a plurality of different material layers. Each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity or the requirements for successful ablation of a desired pattern.

Figure 4:
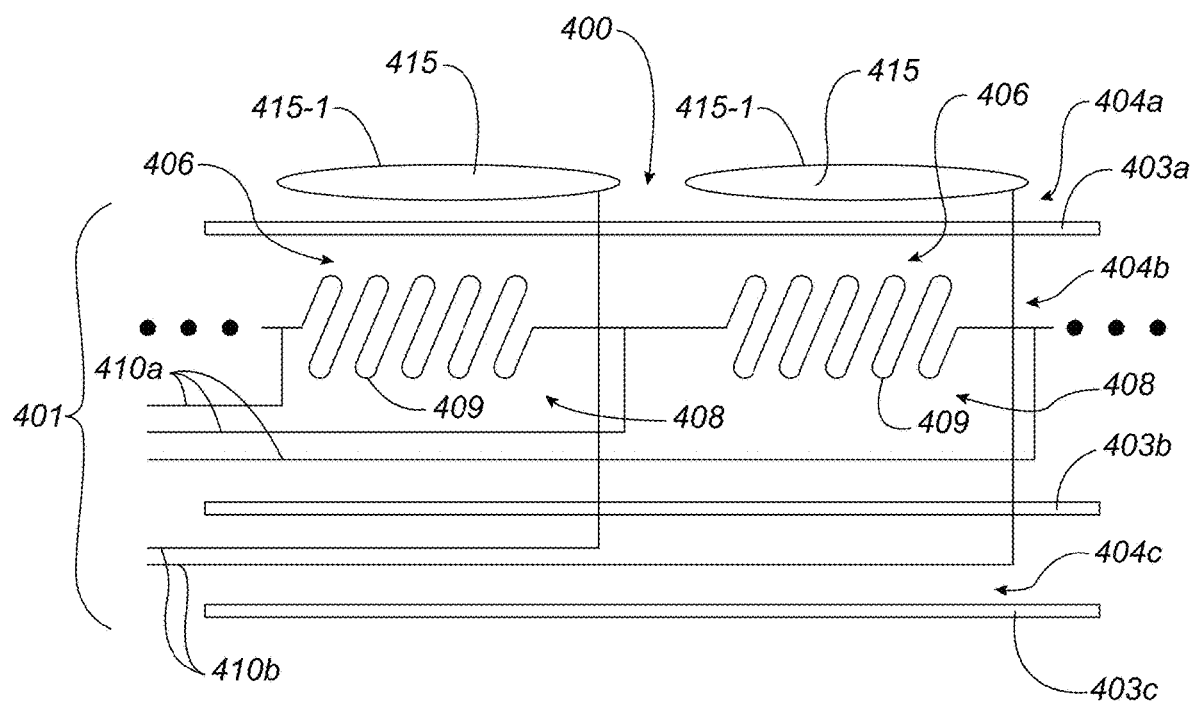
FIG. 4 includes a schematic representation of a transducer-based device that includes a flexible circuit structure according to various example embodiments.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415. It is noted that other electrodes employed in other embodiments may have electrode edges arranged to form different electrodes shapes (for example as shown by electrode edges 315-1 in FIG. 3C).

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias (not shown) in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In some embodiments, the one or more structural layers may include at least one electrically conductive surface (e.g., a metallic surface) exposed to blood flow. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (not shown) (e.g., an intra-cardiac cavity or chamber). The energy delivered to the tissue structures may be sufficient for ablating portions of the tissue structures. The energy delivered to the tissue may be delivered to cause monopolar tissue ablation, bipolar tissue ablation, or blended monopolar-bipolar tissue ablation by way of non-limiting example.

Energy that is sufficient for tissue ablation may be dependent upon factors including transducer location, size, shape, relationship with respect to another transducer or a bodily cavity, material or lack thereof between transducers, et cetera. For example, a pair of electrodes that each is approximately 10 mm$^2$ in surface area and present along a same structural member (e.g., an elongate member 304 in various ones of FIG. 3) may be expected, in some circumstances, to sufficiently ablate intra-cardiac tissue to a depth of approximately 3.1 mm with 2 W of power and to a depth of approximately 4.4 mm with 4 W of power. For yet another non-limiting example, if each electrode in this pair instead has approximately 20 mm$^2$ of surface area, it may be expected that such pair of electrodes will sufficiently ablate intra-cardiac tissue to a depth of approximately 3.1 mm with 4 W of power and to a depth of approximately 4.4 mm with 8 W of power. In these non-limiting examples, power refers to the average power of each electrode summed together, and the depth and power values may be different depending upon the particular shapes of the respective electrodes, the particular distance between them, a degree of electrode-to-tissue contact, and other factors. It is understood, however, that for the same control or target temperature, a larger electrode will achieve a given ablation depth sooner than a smaller electrode. A smaller electrode (e.g., an electrode with a smaller surface area) may need to operate at a higher target temperature to achieve the same ablation depth as compared to a larger (e.g., surface area) electrode (a phenomenon driven by a greater divergence of heat flux of smaller electrodes). Put differently, a maximum ablation depth (e.g., reached when the temperature profile approaches steady state) of a relatively smaller electrode is typically shallower than that of a relatively larger electrode when ablating at the same control or target temperature, and consequently, a given, less than maximum, ablation depth typically is a larger proportion of the final, maximum, ablation depth for a relatively smaller electrode and typically is reached later in the ablation as compared to a relatively larger electrode. This circumstance may be associated with a lower total power provided to the relatively smaller electrode as compared to a relatively larger electrode, but, nonetheless, the power density present in the relatively smaller electrode may be expected to be somewhat higher as compared to the relatively larger electrode. The phrase "power density" in this context means output power divided by electrode area. Note that power density approximately drives the realized control or target temperature, but in various cases, this is a simplification, and as indicated above, the relationship between power density and realized control or target temperature may be modified by such factors as electrode size, shape, separation, and so forth. It is further noted that when a comparison is made between a relatively larger electrode operated at a lower control temperature versus a relatively smaller electrode operated at a higher temperature, further complications may arise when limits on compensation for electrode size with temperature are also dictated, at least in part, by a desire to reduce occurrences of thermal coagulation of blood or steam formation in the ablated tissue. It is noted that power levels in irrigated electrode systems are typically higher (e.g., in the tens of Watts) than those described above.

In some embodiments, each electrode 415 is employed to sense or sample an electrical potential in the tissue proximate the electrode 415 at a same or different time than delivering energy sufficient for tissue ablation. In some embodiments, each electrode 415 is employed to sense or sample intra-cardiac voltage data in the tissue proximate the electrode 415. In some embodiments, each electrode 415 is employed to sense or sample data in the tissue proximate the electrode 415 from which an electrogram (e.g., an intra-cardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring to FIGS. 3A, 3B, 3C, and 3D transducer-based device 300 can communicate with, receive power from or be controlled by a transducer-activation system 322. In some embodiments, elongate members 304 can form a portion of an elongated cable 316 of leads 317 (e.g., control leads, data leads, power leads or any combination thereof), for example by stacking multiple layers, and terminating at a connector 321 or other interface with transducer-activation system 322. The leads 317 may correspond to the electrical connectors 216 in FIG. 2 in some embodiments. The transducer-activation device system 322 may include a controller 324 that includes a data processing device system 310 (e.g., from FIG. 1) and a memory device system 330 (e.g., memory device system 130 from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

Transducer-activation device system 322 includes an input-output device system 320 (e.g., from FIG. 1) communicatively connected to the data processing device system 310 (e.g., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, one or more keyboards, one or more mice (e.g., mouse 335), one or more joysticks, one or more track pads, one or more touch screens or other transducers to transfer information to, from, or both to and from a user, for example a care provider such as a physician or technician. For example, output from a mapping process may be displayed on a display device system 332. Input-output device system 320 may include one or more user interfaces or input/output (I/O) devices, for example one or more display device systems 332, speaker device systems 334, keyboards, mice, joysticks, track pads, touch screens or other transducers employed by a user to indicate a particular selection or series of selections of various graphical information. Input-output device system 320 may include a sensing device system 325 configured to detect various characteristics including, but not limited to, at least one of tissue characteristics (e.g., electrical characteristics such as tissue impedance, tissue conductivity, tissue type, tissue thickness) and thermal characteristics such as temperature. In this regard, the sensing device system 325 may include one, some, or all of the transducers 306 (or 406 of FIG. 4) of the transducer based device 300, including the internal components of such transducers shown in FIG. 4, such as the electrodes 415 and temperature sensors 408.

Transducer-activation device system 322 may also include an energy source device system 340 including one or more energy source devices connected to transducers 306. In this regard, although various ones of FIG. 3 show a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 is fewer than the number of transducers in some embodiments. The energy source device system 340 may for example, be connected to various selected transducers 306 to selectively provide energy in the form of electrical current or power (e.g., RF energy), light or low temperature fluid to the various selected transducers 306 to cause ablation of tissue. The energy source device system 340 may for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, although not shown in various ones of FIGS. 3, the indifferent electrode 326 may be communicatively connected to the energy source device system 340 via one or more communication lines in some embodiments. In addition, although shown separately in various ones of FIGS. 3, indifferent electrode 326 may be considered part of the energy source device system 340 in some embodiments. In various embodiments, indifferent electrode 326 is positioned on an external surface (e.g., a skin-based surface) of a body that comprises the bodily cavity into which at least transducers 306 are to be delivered.

It is understood that input-output device system 320 may include other systems. In some embodiments, input-output device system 320 may optionally include energy source device system 340, transducer-based device 300 or both energy source device system 340 and transducer-based device 300 by way of non-limiting example. Input-output device system 320 may include the memory device system 330 in some embodiments.

Structure 308 can be delivered and retrieved via a catheter member, for example a catheter sheath 312. In some embodiments, a structure provides expansion and contraction capabilities for a portion of the medical device (e.g., an arrangement, distribution or array of transducers 306). The transducers 306 can form part of, be positioned or located on, mounted or otherwise carried on the structure and the structure may be configurable to be appropriately sized to slide within catheter sheath 312 in order to be deployed percutaneously or intravascularly. FIGS. 3A, 3B show one embodiment of such a structure. In some embodiments, each of the elongate members 304 includes a respective distal end 305 (only one called out in each of FIGS. 3A, 3B), a respective proximal end 307 (only one called out in each of FIGS. 3A, 3B) and an intermediate portion 309 (only one called out in each of FIGS. 3A, 3B) positioned between the proximal end 307 and the distal end 305. The respective intermediate portion 309 of each elongate member 304 includes a first or front surface 318a that is positionable to face an interior tissue surface within a bodily cavity (not shown) and a second or back surface 318b opposite across a thickness of the intermediate portion 309 from the front surface 318a. In some embodiments, each of the elongate members 304 is arranged front surface 318a-toward-back surface 318b in a stacked array during an unexpanded or delivery configuration similar to that described in co-assigned International Application No.: PCT/US2012/022061 and co-assigned International Application No.: PCT/US2012/022062. In many cases a stacked array allows the structure 308 to have a suitable size for percutaneous or intravascular delivery. In some embodiments, the elongate members 304 are arranged to be introduced into a bodily cavity (again not shown) distal end 305 first. A flexible, elongated, catheter body 314 is used to deliver structure 308 through catheter sheath 312 according to some embodiments.

In a manner similar to that described in co-assigned International Application No.: PCT/US2012/022061 and co-assigned International Application No.: PCT/US2012/022062, each of the elongate members 304 is arranged in a fanned arrangement 370 in FIGS. 3C, 3D. In some embodiments, the fanned arrangement 370 is formed during the expanded or deployed configuration in which structure 308 is manipulated to have a size too large for percutaneous or intravascular delivery. In some embodiments, structure 308 includes a proximal portion 308a having a first domed shape 309a and a distal portion 308b having a second domed shape 309b. In some embodiments, the proximal and the distal portions 308a, 308b each include respective portions of elongate members 304. In some embodiments, the structure 308 is arranged to be delivered distal portion 308b first into a bodily cavity when the structure is in the unexpanded or delivery configuration as shown in FIGS. 3A, 3B. In various embodiments, the proximal and distal portions 308a, 308b do not include a domed shape in the delivery configuration (for example, as shown in FIGS. 3A, 3B). In some embodiments, the first domed shape 309a of the proximal portion 308a and the second domed shape 309b of the distal portion 308b are arranged in a clam shell configuration in the expanded or deployed configuration shown in FIGS. 3C, 3D.

The transducers 306 can be arranged in various distributions or arrangements in various embodiments. In some embodiments, various ones of the transducers 306 are spaced apart from one another in a spaced apart distribution in the delivery configuration shown in FIGS. 3A, 3B. In some embodiments, various ones of the transducers 306 are arranged in a spaced apart distribution in the deployed configuration shown in FIGS. 3C, 3D. In some embodiments, various pairs of transducers 306 are spaced apart with respect to one another. In some embodiments, various regions of space are located between various pairs of the transducers 306. For example, in FIG. 3D the transducer-based device 300 includes at least a first transducer 306a, a second transducer 306b, and a third transducer 306c (all collectively referred to as transducers 306). In some embodiments each of the first, the second, and the third transducers 306a, 306b, and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In various embodiments, a first region of space 350 is between the respective electrodes 315a, 315b of the first and the second transducers 306a, 306b. In some embodiments, the first region of space 350 is not associated with any physical portion of structure 308. In some embodiments, a second region of space 360 associated with a physical portion of device 300 (e.g., a portion of an elongate member 304) is between the second and the third transducers 306b, 306c. In various embodiments, the second region of space 360 is between the respective electrodes 315b, 315c of the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having a one or more surfaces, at least a portion of the one or more surfaces defining one or more openings in the structure. In these embodiments, a region of space not associated with any physical portion of the structure may extend over at least part of an opening of the one or more openings.

In some embodiments, a first transducer set (e.g., a first set including one or more of transducers 306) is arranged (e.g., axially, circumferentially, or both axially and circumferentially arranged) along, across, or over a portion of catheter body 314 while a second set (e.g., a second set including one or more of transducers 306) is located on structure 308 extending outwardly from a distal end 314a of catheter body 314. An example first transducer set 380 and example second transducer set 382 are shown in FIG. 3C according to some embodiments. In various example embodiments, transducer-based device 300 includes a first transducer set (e.g., first transducer set 380) located proximally of a distal end 314a of catheter body 314 while a second transducer set (e.g., second transducer set 382) is located on structure 308 extending outwardly from the distal end 314a of catheter body 314 (which is better seen in FIG. 3B). In some of these various example embodiments, structure 308 is selectively moveable between a delivery configuration (e.g., FIGS. 3A, 3B) in which the first transducer set 380 and the second transducer set 382 are concurrently arranged in respective arrangements sized for movement through a lumen of catheter sheath 312, and an expanded or deployed configuration (e.g., FIGS. 3C, 3D) in which the second transducer set 382 is arranged in a respective arrangement sized too large for delivery through the lumen of catheter sheath 312 while the first transducer set 380 is arranged in a respective arrangement sized for movement through the lumen of the catheter sheath 312. For example, in some embodiments of the expanded or deployed configuration, each of various transducers 306 in the first transducer set 380 is moveable inwardly into or outwardly from the lumen of catheter sheath 312 while the transducers 306 in the second transducer set 382 are arranged in an arrangement too large for movement inwardly into the lumen of the catheter sheath 312. Advantageously, these embodiments may allow particular transducers (e.g., transducers 306 in the first transducer set 380 to be introduced into or removed from a bodily cavity when the structure 308 is repositioned in the bodily cavity in the expanded or deployed configuration. Repositioning of the structure 308 in the bodily cavity may be required due to variances in a size of the cavity (e.g., a larger than expected size) or variances in an expected positioning of various anatomical landmarks. In either case, additional transducers 306 may be brought into play or out of play as the specific circumstance may require. Bringing a particular transducer 306 into play within a bodily cavity may include appropriately positioning the transducer for a desired sensing function, an energy transmission function, or a sensing and energy transmission function within the bodily cavity.

In FIG. 3C, structure 308 includes an at least one elongate member 304a (also shown in FIG. 3A) according to some embodiments. At least one elongate member 304a is sized and arranged to position at least some of a first set of the transducers 306 (e.g., first transducer set 380) diametrically opposite from a portion 314b (best seen in FIG. 3B) of an outer surface of catheter body 314, the portion of the outer surface not including any transducer. In some example embodiments, portion 314b includes at least a semicircular portion of an outer surface of catheter body 314. In some embodiments, various ones of the elongate members 304 of structure 308 extend outwardly away from the distal end 314a of the catheter body 314 while at least one elongate member 304 (e.g., at least one elongate member 304a) extends outwardly from a location (e.g., location 314c) on the catheter body 314 spaced proximally inward from the distal end 314a of the catheter body 314. In some embodiments, one or more transducers 306 of the first transducer set 380 are located within a region of space between location 314c and distal end 314a. In some embodiments, elongate member 304a is sized and arranged to position first transducer set 380 along the catheter body 314 inwardly from the distal end 314a of the catheter body 314 while positioning a third transducer set 384 outwardly from the distal end 314a of catheter body 314, each of the first and the third transducer sets 380, 384 located on elongate member 304a. In some embodiments, elongate member 304a is sized and arranged to position at least some of transducers 306 over a twisted region 311 of each of at least some of the other elongate members 304. In some embodiments, respective portions of each of at least three of the elongate members 304 are arranged front surface 318a-toward-back surface 318b along a first direction (for example indicated by arrow 318 in FIG. 3A) to form a stacked array in the delivery configuration (e.g., FIG. 3A), and at least one portion of the respective front surface 318a of at least one elongate member 304a is arranged to face in a direction (e.g., represented by arrow 319 in FIG. 3A) other than the first direction in the delivery configuration. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

FIGS. 6A-6F include respective data generation and flow diagrams, which may implement various embodiments of method 600 by way of associated computer-executable instructions according to some example embodiments. In various example embodiments, a memory device system (e.g., memory device systems 130, 330) is communicatively connected to a data processing device system (e.g., data processing device systems 110 or 310, otherwise stated herein as "e.g., 110, 310") and stores a program executable by the data processing device system to cause the data processing device system to execute various embodiments of method 600 via interaction with at least, for example, a transducer-based device (e.g., transducer-based devices 200, 300, or 400). In these various embodiments, the program may include instructions configured to perform, or cause to be performed, various ones of the instructions associated with execution of various embodiments of method 600. In some embodiments, method 600 may include a subset of the associated blocks or additional blocks than those shown in FIGS. 6A-6F. In some embodiments, method 600 may include a different sequence indicated between various ones of the associated blocks shown in FIGS. 6A-6F.

Figure 5A:
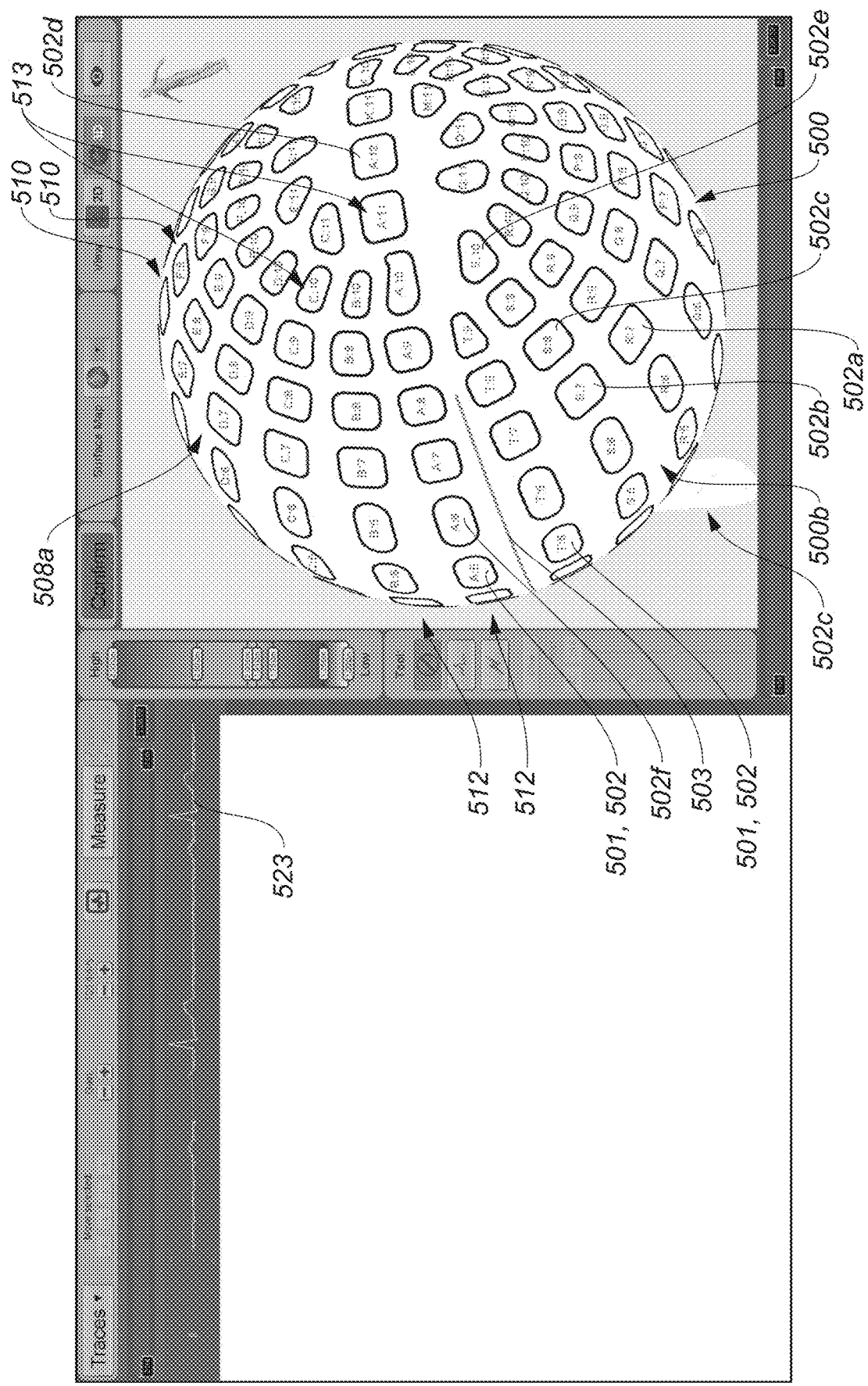
FIG. 5A includes a graphical interface according to various example embodiments, the graphical interface including a graphical representation of at least a portion of a transducer-based device including a plurality of transducer graphical elements.

In some embodiments, block 604 is associated with computer-executable instructions (e.g., graphical representation instructions or graphical interface instructions or display instructions provided by a program) configured to cause an input-output device system (e.g., input-output device system 120 or 320) to display a graphical representation. FIG. 5A illustrates a graphical interface including a graphical representation 500 provided by the input-output device system according to one example embodiment provided in accordance with display instructions associated with block 604 in FIG. 6A. In some embodiments, the graphical representation 500 includes a three-dimensional graphical representation of at least a portion of a transducer-based device (e.g., structure 308 in FIG. 3) and is provided in accordance with the computer-executable program instructions associated with block 606. The instructions associated with block 606 may be configured to access a predefined model (e.g., a computer-aided-design ("CAD") or other computer-readable model stored in memory device system 130, 330) of the at least the portion of the transducer-based device and display the at least the portion of the transducer-based device according to such model. In some embodiments encompassing FIG. 5A, the representation of the transducer-based device is provided by or among various elements of graphical representation 500. In some embodiments, the graphical interface depicts the transducer-based device as including a first domed portion 508a associated with a first domed portion of the transducer-based device (e.g., proximal portion 308a when having the first domed shape 309a) and a second domed portion 508b associated with a second domed portion of the transducer-based device (e.g., distal portion 308b having the second domed shape 309b). A separation graphical element 503 may be employed between the first and the second domed portions 508a, 508b in some embodiments, but may be omitted in other embodiments. Various other transducer-based devices may be depicted according to the instructions associated with block 606 in other embodiments. FIGS. 5A, 5B, 5C, 5D, 5E, 5F, 5G, 5H, 5I, 5J, 5K, 5J, 5L, and 5M (collectively FIG. 5) are presented in this disclosure in association with various embodiments. It is understood that each of these embodiments need not be associated with all of the FIG. 5, and in some cases will only be associated with a subset of the FIG. 5.

In some embodiments according to FIG. 5A, a plurality of graphical elements 501 (only two called out) are depicted (e.g., according to the instructions associated with block 606) among various elements of graphical representation 500. In various embodiments, each of the graphical elements 501 is respectively associated with a respective one of a plurality of transducer sets. Each respective transducer set includes at least one of a plurality of transducers included as part of the transducer-based device (e.g., transducer-based devices 200, 300, or 400) and each respective transducer set has at least one different transducer than another of the other transducer sets. In various particular embodiments, each respective transducer set has at least one different transducer than each of the other transducer sets.

Figure 5B:
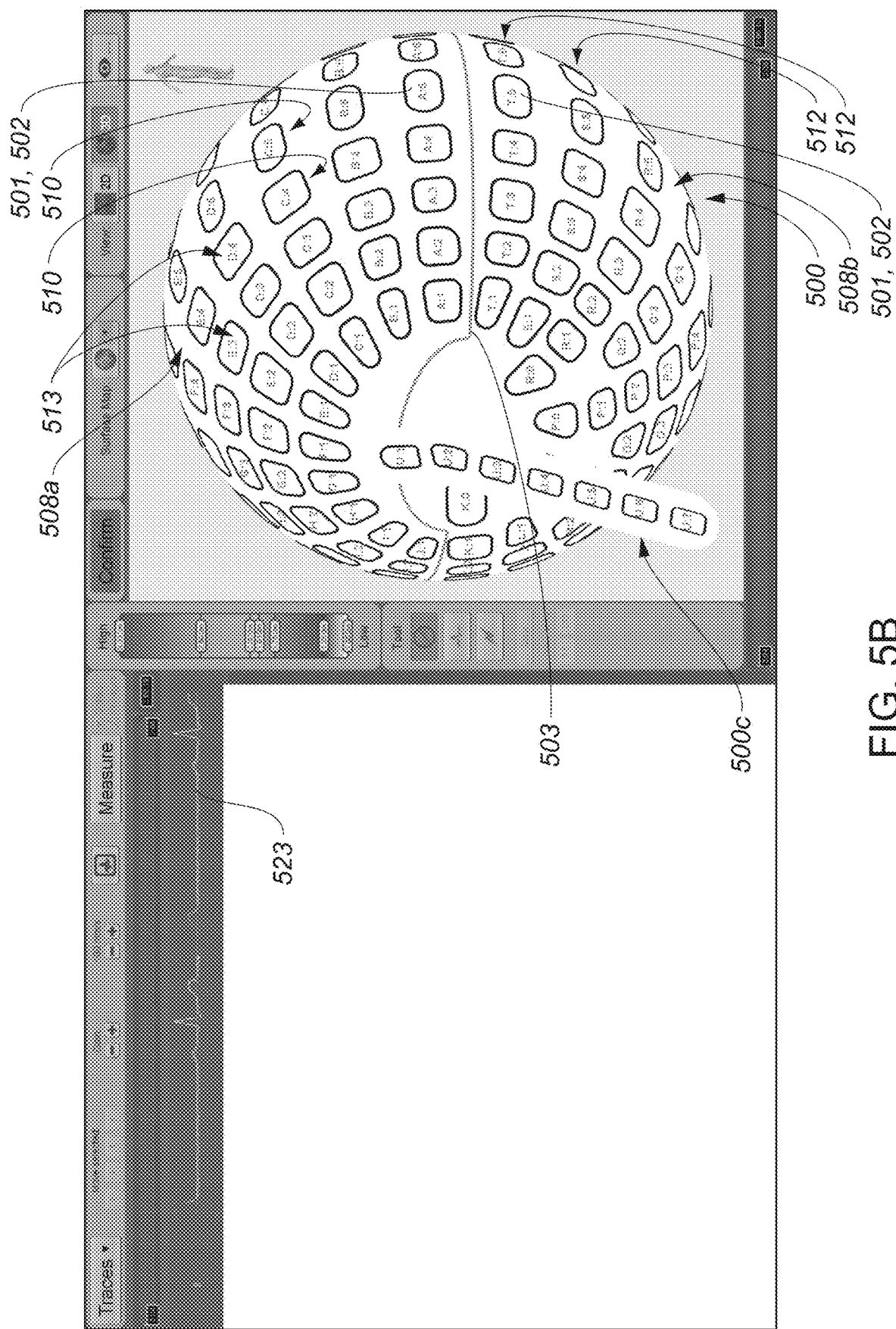
FIG. 5B includes the graphical interface of FIG. 5A, but shows a different viewing direction of the transducer-based device as compared to FIG. 5A in accordance with various example embodiments.

FIG. 5B shows the graphical interface in which the display instructions have been configured to cause (for example, in response to a user input via an input-output device system such as 120, 320) the three-dimensional graphical representation of the transducer-based device to be manipulated so as to be viewed from a different viewing angle than that shown in FIG. 5A. In some embodiments, the depiction of the transducer-base device may include various other elements thereof. For example, FIG. 5B depicts the transducer-based device as including an elongated portion 500c (e.g., extending from or toward domed portion 508a in some embodiments). In various embodiments, elongated portion 500c is representative of a particular element that is the same or similar to at least one elongate member 304a in various ones of FIG. 3B. It is noted that three-dimensional representations of at least portion of the transducer-based device are shown in FIGS. 5A, 5B, 5C, 5D and 5L.

Referring to some embodiments encompassing FIG. 5A, each of at least some of the graphical elements 501 is provided by a respective one of a plurality of transducer graphical elements 502 that include at least a first transducer graphical element 502a, a second transducer graphical element 502b, and a third transducer graphical element 502c (e.g., all the transducer graphical elements forming part of a group of transducer graphical elements 502). In some embodiments, each transducer graphical element 502 is associated with a single respective transducer of the transducer-based device. In some example embodiments, each transducer graphical element 502 is representative of a respective transducer of the transducer-based device. In some example embodiments, each transducer graphical element 502 is representative of a location or position of a respective transducer of the transducer-based device. In some embodiments, the graphical representation 500 includes a first spatial relationship between the transducer graphical elements 502 that is consistent with a second spatial relationship between the corresponding transducers associated with the transducer graphical elements 502. For example, in some embodiments, the transducer graphical elements 502 in the three dimensional graphical representation 500 in FIGS. 5A, 5B may exhibit a same spatial relationship that the transducers 309 exhibit in the transducer based device 300 in FIG. 3C. Or, in some embodiments, the transducer graphical elements 502 in other graphical representations 500 in others of FIG. 5 may exhibit a respective or corresponding spatial relationship that the transducers 309 exhibit in the transducer based device 300 in FIGS. 3C and 3D. In this regard, in some embodiments, the graphical representation 500 may include a first spatial relationship between the transducer graphical elements 502 that is consistent with a second spatial relationship between the corresponding transducers associated with the transducer graphical elements 502 when the corresponding transducers are arranged in a deployed configuration (e.g., FIGS. 3C, 3D). In some embodiments, each particular depicted transducer graphical element 502 is shown having a shape that is consistent with the particular transducer (or portion thereof) that the particular transducer graphical element 502 is representative of. For example, in FIG. 5A, transducer graphical element 502d includes an essentially square shape with rounded corners that is consistent with the square, rounder cornered shape of the electrode 315d of transducer 306d shown in FIG. 3D. Additionally, in FIG. 5A, transducer graphical element 502e includes an essentially triangular shape with rounded corners that is consistent with the triangular, rounded cornered shape of the electrode of transducer 306e shown in FIG. 3D. Further, in FIG. 5A, transducer graphical element 502f includes an essentially oval shape that is consistent with the oval shape of the electrode 315f of transducer 306f shown in FIG. 3D. Others transducer graphical elements 502 in FIGS. 5A and 5B have shapes that are consistent with respective ones of the electrodes shown in FIGS. 3C and 3D. A graphical representation 523 of an electrocardiogram (ECG/EKG) signal 523 is also shown in the graphical interface of various ones of FIG. 5.

Figure 5C:
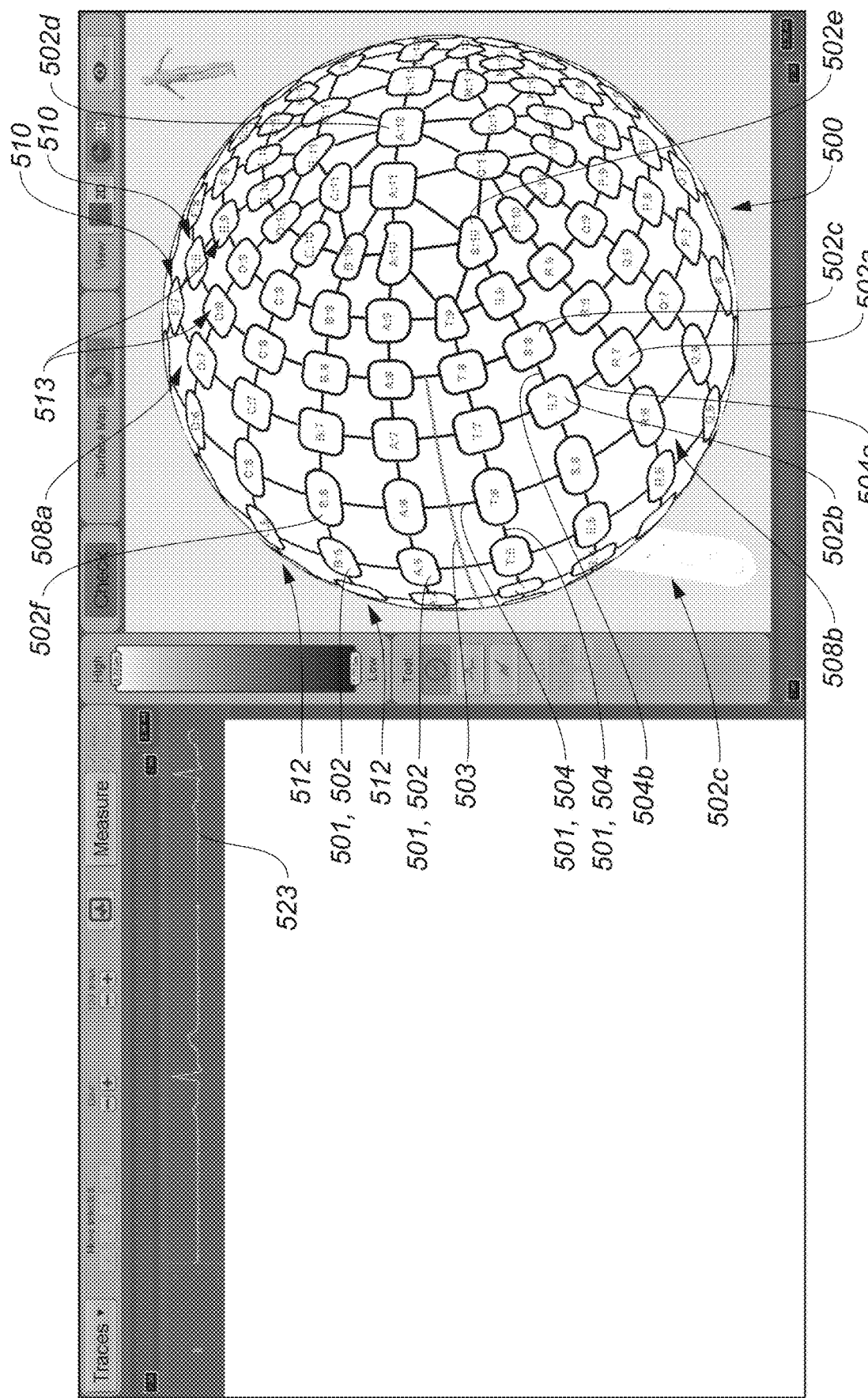
FIG. 5C includes the graphical representation provided by the graphical interface of FIG. 5A with the addition of various between graphical elements positioned between various ones of transducer graphical elements in accordance with various example embodiments.
Figure 5D:
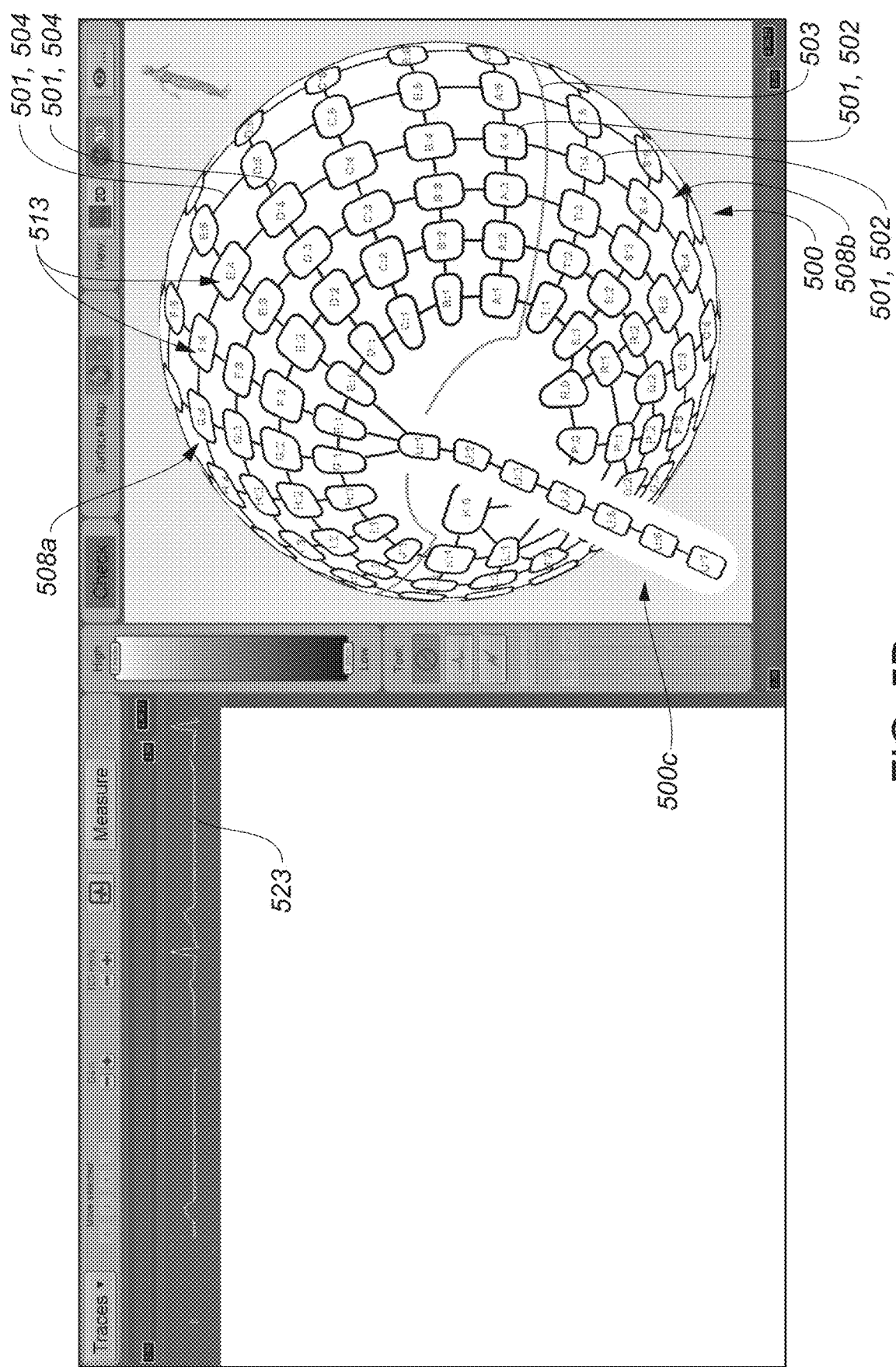
FIG. 5D includes the graphical interface of FIG. 5C, but shows a different viewing direction of the transducer-based device as compared to FIG. 5C in accordance with various example embodiments.

In some example embodiments, graphical elements 501 may include alternate or additional forms. For example FIG. 5C shows an example embodiment in which each of at least some of the graphical elements 501 are provided by a respective one of a plurality of between graphical elements 504 including a first between graphical element 504a and a second between graphical element 504b (e.g., all the between graphical elements collectively referred to as between graphical elements 504). FIG. 5D shows an embodiment of the graphical interface in which the display instructions have been configured to cause (for example, in response to a user input via an input-output device system such as 120, 320) the depiction of the transducer-based device to manipulated so as to be viewed from a different viewing angle than that shown in FIG. 5C. In some embodiments, between graphical elements 504 are shown in addition to various ones of the transducer graphical 502 shown in FIGS. 5A and 5B. In some embodiments, between graphical elements 504 are provided separately or with other embodiments of graphical elements 501. In various embodiments, each of the between graphical elements 504 is associated with a set of at least two (e.g., a group) of the transducers of the transducer-based device. In some example embodiments, each of the between graphical elements 504 is associated with a pair of transducers in the transducer-based device. In some example embodiments, each between graphical element 504 is associated with a region of space between a respective pair of transducers in the transducer-based device. In some example embodiments, each between graphical element 504 is associated with a region of space between a respective pair of adjacent ones of the transducers in the transducer-based device.

In some embodiments, first transducer graphical element 502a is associated with a first transducer (e.g., first transducer 306a) of the transducer-based device, second transducer graphical element 502b associated with a second transducer (e.g., second transducer 306b) of the transducer-based device, and third transducer graphical element 502c associated with a third transducer (e.g., third transducer 306c) of the transducer-based device. In some embodiments, each of the transducer graphical elements 502a, 502b and 502c has a shape that is consistent with a shape of the respective electrode 315a, 315b, 351c of the corresponding one of the transducers 306a, 306b and 306c. In some embodiments, the first between graphical element 504a is associated with a first region of space that is between the first and the second transducers and the second between graphical element 504b is associated with a second region of space that is between the second and the third transducers. In some embodiments, the first region of space is a region of space that is not associated with any physical part of the transducer-based device (e.g., first region of space 350) and the second region of space is a region of space that is associated with a physical part of the transducer-based device (e.g., second region of space 360). In some embodiments, each of the first and the second between graphical elements 504a, 504b is associated with a region of space that does not include a transducer of the transducer-based device. In some embodiments, each of the first and the second between graphical elements 504a, 504b is associated with a region of space that does not include any transducer. It is understood that a "region of space" need not be a vacant space but can include physical matter therein.

In some embodiments, the first between graphical element 504a is positioned between the second and the first transducer graphical elements 502b, 502a among the graphical representation 500. In some embodiments, the second between graphical element 504b is positioned between the second and the third transducer graphical elements 502b, 502c among the graphical representation 500. In other example embodiments, other spatial relationships exist between the transducer graphical elements 502 and the between graphical elements 504 in the graphical representation.

The transducer graphical elements 502, the between graphical elements 504, or both may have different sizes, shapes or forms than those shown in the illustrated embodiment. In some embodiments, at least one particular one of the transducer graphical elements 502 may be depicted with a different shape, size, or form than the respective one of the shape, size or form of the respective portion of the particular transducer to which the particular one of the transducer graphical elements 502 corresponds. In some embodiments, different ones of the between graphical elements 504 may be depicted with different shapes, sizes, or forms.

With reference to various ones of FIGS. 5, at least a portion of the transducer graphical elements 502, and at least a portion of the between graphical elements 504 are arranged in a plurality of rows 510 (two called out in FIG. 5A) and a plurality of columns 512 (two called out in FIG. 5A). In some embodiments, each row corresponds to a respective one of number "0", "1", "2", "3", "4", "5", "6", "7", "8", "9", "10", and "11", and each column 512 corresponds to a respective one of letters "A", "B", "C", "D", "E", "F", "G", "H", "I", "J", "K", "L", "M", "N", "O", "P", "Q", "R", "S", and "T", each of the numbers and letters used as part of the unique identifier 513 (only two called out with reference numeral 513 in FIG. 5A) of each transducer graphical element 504. In some embodiments, the plurality of rows 510 and columns 512 correspond to condition in which structure 308 is in the deployed configuration. In some embodiments, a portion of each of the columns 512 corresponds to region of space associated with a physical portion of the transducer-based device (e.g., an elongate member 304). In some embodiments, each of the columns 512 corresponds to at least a portion of the transducers located on a particular elongate member of a transducer-based device (e.g., an elongate member 304). In some embodiments, at least one of the columns 512 includes at least one transducer graphical element 502 having a shape that is different than the respective shape comprised by any of the transducer graphical elements 502 included in at least one other of the columns 512. For example, the "A" column 512 includes a transducer graphical element 502 identified as "A:10" that has a shape that is different than any of the transducer graphical elements 502 comprised by at least one of the other columns 512. In some embodiments, at least a first one of the rows 510 includes identically shaped transducer graphical elements 502 (e.g., row 510 that includes transducer graphical elements 502 identified as "A:6", "B:6", "C:6", "D:6", "E:6", "F:6", "G:6", "H:6", "I:6", "J6", "K:6", "L:6", "M:6", "N:6", "O:6", "P:6", "Q:6", "R:6", "S:6" and "T:6"), and at least a second one of the rows 510 includes differently shaped transducer graphical elements 502 (e.g., row 510 that includes transducer graphical elements 502 identified as "A:10", "B:10", "C:10", "D:10", "E:10", "F:10", "G:10", "H:10", "I:10", "K:10", "L:10", "M:10", "N:10", "O:10", "P:10", "Q:10", "R:10", and "S:10"). In some example embodiments, a portion of each of the rows 510 corresponds to regions of space not associated with any physical portion of the transducer-based device (e.g., regions of space 350 between adjacent ones of the elongate members 304). In other example embodiments, different numbers of transducer graphical elements 502 and different numbers and spatial arrangements of between graphical elements 504 may be depicted in the graphical representation. In other example embodiments, different numbers and spatial arrangements of rows 510 and columns 512 may be depicted in the graphical representation. In various embodiments, each of the between graphical elements (e.g., between graphical elements 504) depicted in the graphical representation are representative of a respective physical path extending between a respective pair of transducers of the transducer-based device. Each of the physical paths may extend over a physical surface of the transducer-based device or over a portion of an opening defined by a physical surface of the transducer-based device. In the embodiment shown in FIG. 5C, each between graphical element 504 is representative of a respective physical path extending between the respective transducers associated with the adjacent pair of transducer graphical elements 502 that the between graphical element 504 extends between. In the embodiment shown in FIG. 5C, each adjacent pair of the transducer graphical elements 502 may be provided along a row 510 (two called out in FIG. 5C) of the graphical elements 501, along a column 512 (two called out in FIG. 5C) of the graphical elements 501, or diagonally between a row 510 and a column 512.

Referring back to FIGS. 5A, 5B, the plurality of rows 510 and the plurality of columns 512 are depicted as a three-dimensional arrangement in the graphical representation. In some embodiments, at least two of the plurality of columns 512 are depicted in the graphical representation extending along respective directions that converge with respect to one another. In some embodiments, at least two of the plurality of columns 512 are depicted in the graphical representation extending along non-parallel directions and at least two of the plurality of rows 510 is depicted extending along parallel directions. In some embodiments, the rows 510 and the columns 512 are depicted in the graphical representation in an arrangement in which the columns 512 are circumferentially arranged. In some embodiments, the rows 510 and the columns 512 are depicted in the graphical representation in an arrangement having a generally spherical shape. The plurality of columns 512 may be depicted like lines of longitude, and the plurality of rows 510 may be depicted like lines of latitude. Although the rows 510 and columns 512 are illustrated in FIGS. 5A-5D as circumferential lines (like lines of longitude and latitude), such rows 510 and columns 512 can take other forms, as shown, for example, in FIGS. 5E and 5F, discussed in more detail below, according to some embodiments.

Figure 5E:
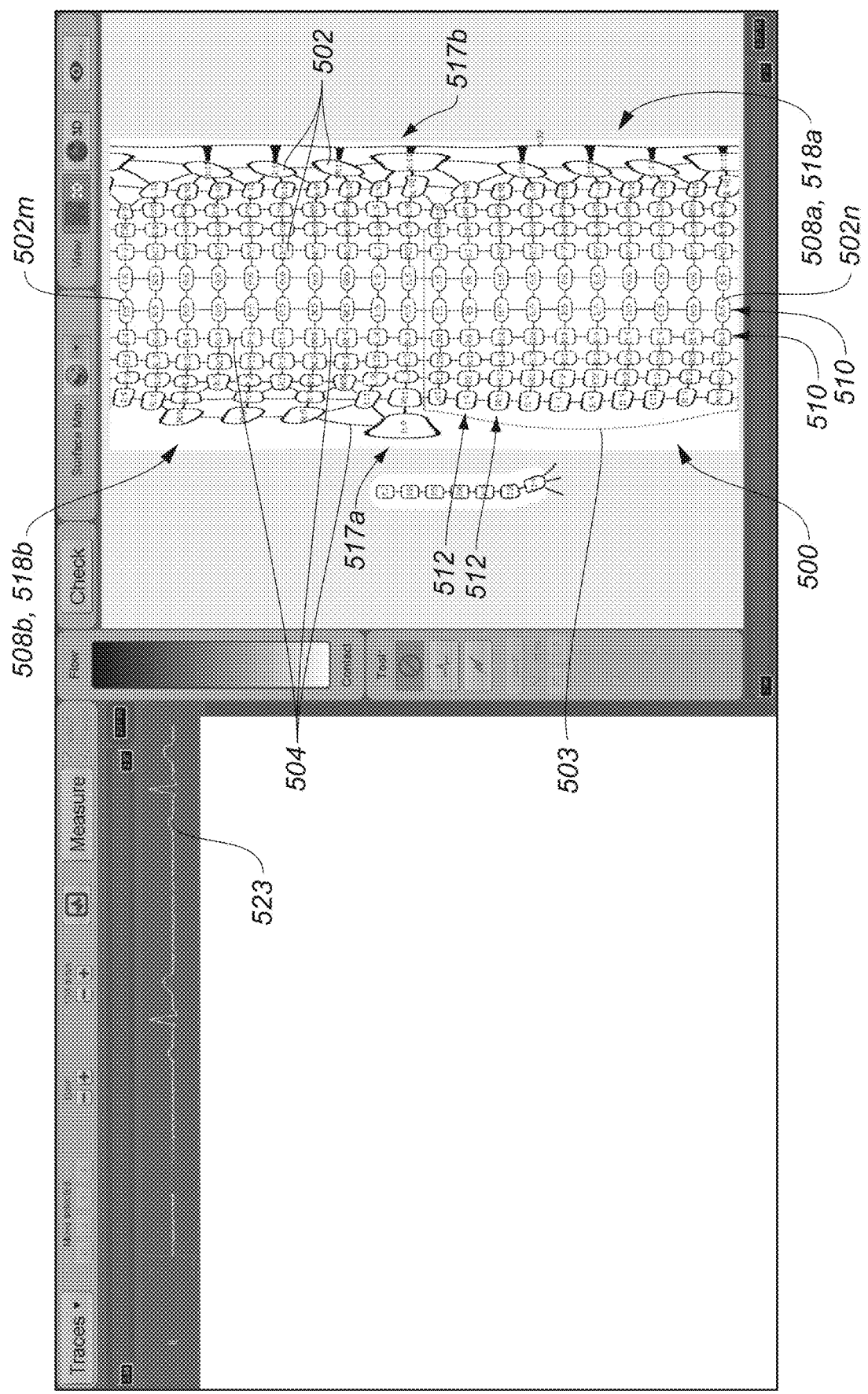
FIG. 5E includes a two-dimensional graphical representation of the transducer-based device illustrated in FIGS. 5C and 5D in accordance with various example embodiments.
Figure 5F:
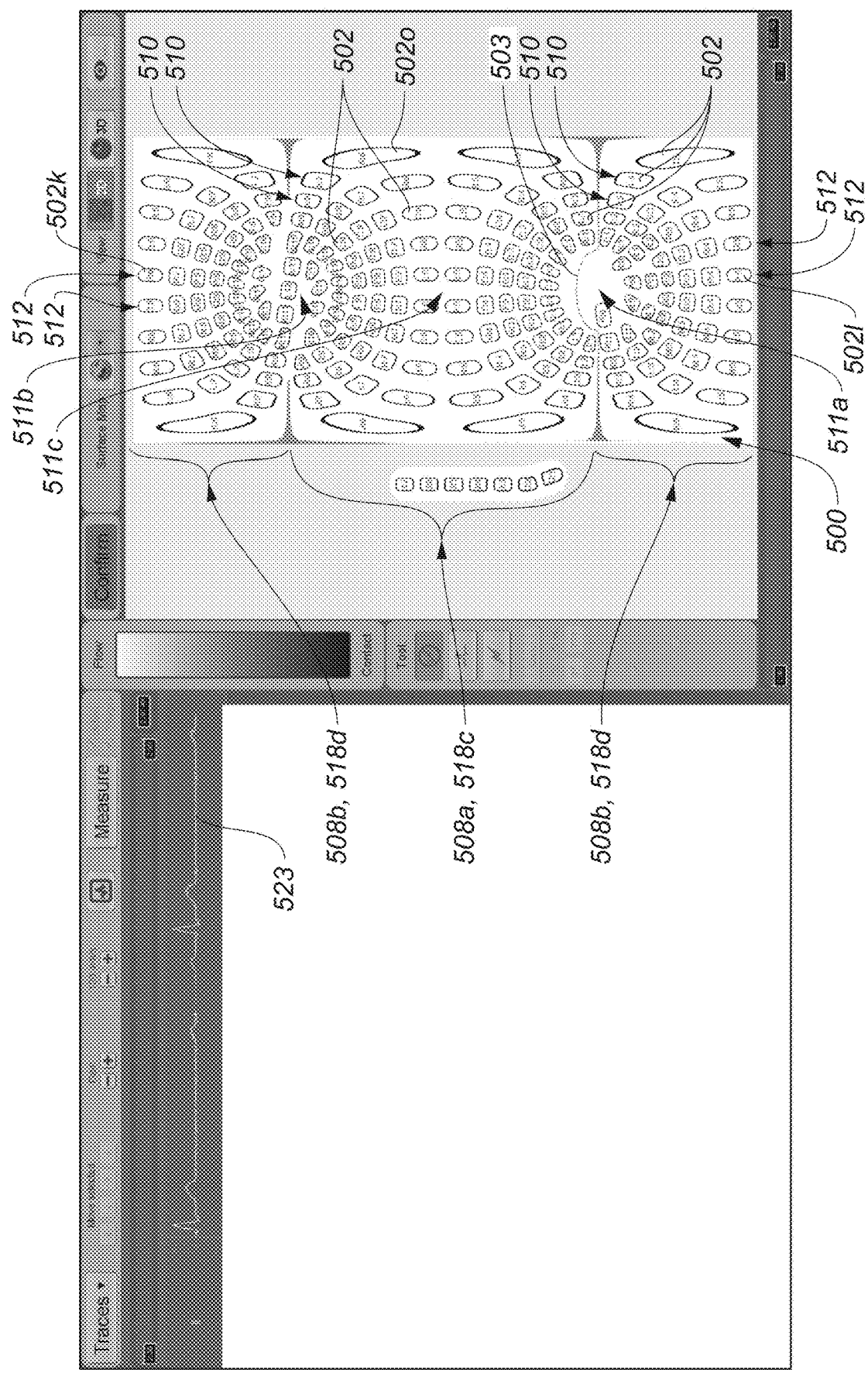
FIG. 5F includes a two-dimensional graphical representation of the transducer-based device illustrated in FIGS. 5A and 5B in accordance with various example embodiments.

The display instructions (e.g., according to block 604, 606, or both) may include instructions (e.g., instructions responsive to a user input made via an input-output device system) configured to vary the depiction of the portion of the transducer-based device between a three-dimensional representation (e.g., as depicted in various ones of FIGS. 5A, 5B, 5C, and 5D) and a two dimensional representation (e.g., as depicted by FIG. 5E or 5F). Various two-dimensional representations are possible in various embodiments. For example, the two-dimensional representation depicted in FIG. 5E may be generated according to the display instructions according to a Mercator projection or other three-dimensional-to-two-dimensional projection, known in the art, according to some embodiments. In other embodiments, the two-dimensional representation need not be a projection from a three-dimensional model, and may merely be any two-dimensional representation, e.g., including an arrangement of transducers.

The two-dimensional representation depicted in FIG. 5E, according to some embodiments, represents the first domed portion 500a (e.g., shown in FIGS. 5C, 5D) of the depicted transducer-based device as first Mercator projection 518a and the second domed portion 500b (e.g., shown in FIGS. 5C, 5D) of the depicted transducer-based device as a second Mercator projection 518b. The first and the second Mercator projections 518a and 518b advantageously allow for simultaneous viewing of all the transducer graphical elements 502 and the between graphical elements 504. Columns 512 and rows 510 are depicted two-dimensionally in FIG. 5E. In some embodiments, separation element 513 is also depicted in a two-dimensional configuration.

As discussed above, other two-dimensional representations may be implemented and may be user-selectable for viewing. For example, FIG. 5F illustrates a transverse Mercator projection employed according to some embodiments. In FIG. 5F, the transverse Mercator projection includes two portions 518c, 518d, each of the portions 518c, 518d representative of a respective one of first and second domed portions 500a and 500b in the corresponding three-dimensional representation. In FIG. 5F, portion 518d of the transverse Mercator projection is shown as two parts, each part at least depicting the transducer graphical elements 502 in a respective one of two parts of the domed portion 508b. In FIG. 5F, portion 518c is representative of first domed portion 508a. In some embodiments, various ones of the columns 512 radiate outwardly radially or quasi-radially from particular ones of a plurality of pole regions 511a and 511b represented in the graphical representation 500. In some embodiments, various ones of the rows 510 are circumferentially arranged about particular ones of a plurality of pole regions 511a and 511b.

In some embodiments, at least some of the between graphical elements 504 are not shown in various ones of the displayable two-dimensional representations. For example, in FIG. 5F, between graphical elements 504 have been selectively controlled, e.g., in response to user input, not to be visible among the graphical representation. In various embodiments, the transducer graphical elements 502 shown in each of the FIGS. 5E and 5F are arranged with respect to one another according to a spatial relationship that corresponds to a spatial relationship that the transducer graphical elements are arranged in the three-dimensional representations shown in various ones of FIGS. 5A, 5B, 5C, 5D and 5L. In various embodiments, the transducer graphical elements 502 shown in each of the FIGS. 5E and 5F are arranged with respect to one another according to a spatial relationship that corresponds to a spatial relationship that particular transducers that the transducer graphical elements 502 correspond to, are arranged with respect to one another when a supporting structure (e.g., structure 308) is in a deployed configuration.

Various computer-executable instructions may be configured to control various input element control functions (e.g., mouse drag functions, touch screen drag functions) between various operating modes such as rotating and panning modes. A rotating mode may be advantageously used for manipulation of a three-dimensional representation of a transducer-based device or other portions of the graphical representation 500 to allow for viewing one or more portions of the three-dimensional representation of the transducer-based device or various portions of the graphical representation 500 that were not previously viewable (e.g., a manipulation between the views shown in FIGS. 5A and 5B or a manipulation between the views shown in FIGS. 5C and 5D). In some embodiments, a panning mode may be advantageously used for manipulation of a two-dimensional representation of the transducer-based device or other portions of the graphical representation 500 to allow for viewing of different arrangements of various graphical elements in the representation of a transducer-based device or other portions of the graphical representation 500. For example, in FIG. 5F, an up-down panning manipulation (e.g., caused in response to a mouse drag or touch screen drag function) may adjust a size of each of the portions 518d that are representative of domed portion 508b (e.g., one of the portions 518d increasing in size while the other portion 518d decreases in size) or in some cases combine the plurality of portions 518d into a fewer number of portions (e.g., a single portion 518d), or in some cases divide portion 518c representative of the first domed portion 508a into a plurality of portions 518c.

In some embodiments, a rotating mode may be advantageously used for manipulation of a two-dimensional representation of the transducer-based device or other portions of the graphical representation 500 to allow for viewing of different arrangements of various graphical elements in the transducer-based device or other portions of the graphical representation 500. For example, in FIG. 5F, a rotation mode (for example, caused in response to a mouse drag or touch screen drag function) may be employed to rotate or revolve various ones of the transducer graphical elements 502 or other elements of the graphical representation 500 about a selected one of two pole regions 511a and 511b. It is noted in some embodiments, a particular rotation of a first set of graphical elements about one of the pole regions 511a and 511b in a first particular rotational direction (e.g., a clockwise direction) may be automatically accompanied by a particular rotation of a second set of graphical elements about the other of the pole regions 511a and 511b in second particular rotation direction different than the first particular rotational direction (e.g., a counterclockwise direction).

It is noted that, even though an entirety of the representation of the transducer-based device may be shown in the two-dimensional representation, various panning or rotation modes such as described above may be employed to position various ones of the displayed graphical elements in a configuration that may provide a better understanding of a particular relationship between the graphical elements. For example, in some embodiments, the transducer graphical elements 502*k* and 502*l* respectively identified as "P:5" and "P:6" in FIG. 5F correspond to an adjacent pair of transducers, but are displayed apart from one another in the two portions 518*b*. A rotation (for example as described above) about one of the two pole regions 511*a*, 511*b* may be used to position the transducer graphical elements 502*k* and 502*l* respectively identified as "P:5" and "P:6" closer together, for example in the medial region 511*c* to better convey information describing the adjacency of the transducers corresponding to the transducer graphical elements 502*k* and 502*l*. In some example embodiments, a rotation (for example as described above) about one of the two pole regions 511*a*, 511*b* may be used to position the transducer graphical elements 502*k* and 502*l* adjacently together without any others of the transducer graphical elements 502 positioned therebetween.

In some embodiments, the respective transducers of the adjacent pair of transducers (e.g., an adjacent pair of transducers 306) corresponding to transducer graphical elements 502*k* and 502*l* are located a same structural member (e.g., a same one of elongate members 304). In some embodiments, a region of space that includes a physical portion of the transducer-based device is located between the respective transducers of the adjacent pair of transducers (e.g., an adjacent pair of transducers 306) corresponding to transducer graphical elements 502*k* and 502*l*. In various embodiments, the rotation mode synchronizes rotation about one of the pole regions 511*a*, 511*b* with the rotation about the other of the pole regions 511*a*, 511*b* such that various transducer graphical elements 502 representative of an adjacent pair of transducers maintain a spatial relationship when rotated into the medial region 511*c* that is consistent with the spatial relationship of the corresponding adjacent transducers. In FIG. 5F, various columns of adjacent transducer graphical elements 502 radially extend or converge towards each of the pole regions 511*a* and 511*b*. The synchronized rotation about one of the pole regions 511*a*, 511*b* with the rotation about the other of the pole regions 511*a*, 511*b* allows each of the columns to continue to radially extend or converge towards each of the pole regions 511*a* and 511*b* at least while the columns are positioned in portion 518*c*

In some embodiments, various ones of these manipulation modes may allow the user to better understand a relationship or interaction between the transducer graphical elements 502 and any displayed physiological information (e.g., intracardiac information) displayed in the graphical representation (e.g., as described below at least with respect to FIGS. 5G-5M). In some embodiments, various ones of these manipulation modes may allow the user to better understand a relationship of various ones of the transducers corresponding to various ones of the transducer graphical elements to facilitate a selection or non-selection thereof. It is noted that various ones of the manipulations modes are not limited to the two-dimensional representation of FIG. 5F and may be employed with other forms of two-dimensional representations. For example, in some embodiments, the transducer graphical elements 502*m* and 502*n* respectively identified as "T:5" and "A:5" in FIG. 5E correspond to an adjacent pair of transducers (e.g., an adjacent pair of transducers 306), but are displayed apart from one another. An up-down panning manipulation (for example as described above) may be employed to better visualize the adjacency of the transducers corresponding to the transducer graphical elements 502*m* and 502*n* respectively identified as "T:5" and "A:5". In some embodiments, the respective transducers of the adjacent pair of transducers (e.g., an adjacent pair of transducers 306) corresponding to transducer graphical elements 502*m* and 502*n* are located on different structural members (e.g., different or separate ones of elongate members 304). In some embodiments, a region of space that does not include any physical portion of the transducer-based device is located between the respective transducers of the adjacent pair of transducers (e.g., an adjacent pair of transducers 306) corresponding to transducer graphical elements 502*m* and 502*n*.

A Mercator projection such as that employed in embodiments associated with FIG. 5E may include various distortions in some of the elements (e.g., transducer graphical elements 504) at least proximate the boundary regions 517*a*, 517*b* of the projection. In some embodiments, the columns 512 of graphical elements 512 act like converging lines of longitude in a three-dimensional representation (e.g., FIGS. 5A, 5B, 5C and 5D) and the distortions at least proximate the boundary regions 517*a*, 517*b* may be provided to account or compensate for the convergence of columns 512. It is noted, however, that a panning mode (e.g., a left-right panning mode) that may move one of the boundary regions 517*a*, 517*b* inwardly or centrally within the graphical representation may in some embodiments, maintain the distortions in the various graphical regions that occupy or move along with the moved one of the boundary regions 517*a*, 517*b*. Moving these distorted regions inwardly or centrally within the field of view of the user may not provide, in some cases, a readably understandable representation of various facets of these graphical elements (e.g., a spatial relationship therebetween). The two-dimensional representation depicted in FIG. 5F, on the other hand, centralizes the graphical elements (e.g., transducer graphical elements 502) that are located in the boundary regions 517*a*, 517*b* of FIG. 5F centrally proximate the pole regions 511*a*, 511*b* of FIG. 5F with reduced levels of distortions. In this regard, the graphical representation of FIG. 5F provides a good understanding of the various relationships (e.g., spatial relationships) associated with "pole" areas (e.g., areas where the columns 312 converge like lines of longitude) of the corresponding three-dimensional representation. On the other hand, the graphical representation of FIG. 5E provides a good understanding of the various relationships (e.g., spatial relationships) associated with "equatorial areas (e.g., equatorial regions of columns 312 when acting like lines of longitude) of the corresponding three-dimensional representation. In some embodiments, two or more different two-dimensional representations are concurrently displayed via an input-output device system (e.g., 120, 320). In some embodiments, both of the two-dimensional representations shown in FIGS. 5E and 5F are concurrently displayed via an input-output device system (e.g., 120, 320).

In each of the FIGS. 5E and 5F, each of the transducer graphical elements 502 has a respective shape that is the same, or generally the same as, a shape of at least a portion of a corresponding transducer (e.g., transducer 306) that the transducer graphical element represents. In some embodiments, each of the transducer graphical elements 502 has a respective shape that is the same, or generally the same, as shape of an electrode (e.g., electrode 315) of a corresponding transducer (e.g., transducer 306) that the transducer graphical element represents. In each of the FIGS. 5E and 5F, the shape of each of at least some of the transducer graphical elements 502 is distorted and deviates in some aspects from the respective shape of a corresponding electrode. Unlike a distortion caused by the use of "perspective" (e.g., a varying of an appearance of objects in respect to their perceived relative distance and positions) in corresponding three-dimensional representations (e.g., FIGS. 5A, 5B, 5C, 5D), various graphical elements in FIGS. 5E and 5F employ other forms of distortion (for example, as described above in this description). For example, in FIG. 5F, increased levels of distortions (e.g., increased sizes or dimensions, increased stretching) accompany various ones of the transducer graphical elements 502 that are increasingly spaced from pole regions 511a and 511b. In FIG. 5E, increased levels of distortions (e.g., increased sizes or dimensions, increased stretching) accompany various ones of the transducer graphical elements 502 that are spaced relatively close to the boundary regions 517a, 517b as compared with various ones of the transducer graphical elements that are located relatively far from the boundary regions 517a, 517b. In either case, and unlike the perspective-based distortions employed in some three-dimensional representations, some of the more highly distorted transducer graphical elements 504 include enlarged shapes (e.g., relative to less distorted graphical elements 502 displayed centrally in each of two-dimensional representations) and correspond to transducers that would be spaced relatively farther from a viewer (e.g., with the less distorted transducer graphical elements 502 corresponding to transducers that would be spaced relatively closer to the viewer).

In some embodiments associated with FIG. 5F, a rotation mode may be employed to rotate at least some of the transducer graphical elements 502 about one of the pole regions 511a and 511b and changes in the shape or size of various ones of transducer graphical elements 502 during the rotation may occur. In some embodiments associated with FIG. 5F, a rotation mode may be employed to rotate at least some of the transducer graphical elements 502 about one of the pole regions 511a and 511b to vary a level of distortion comprised by various ones of transducer graphical elements 502. For example, the transducer graphical element 502o identified as "A:6" may in some embodiments, be rotated about pole region 511b with its size or level distortion reducing as it rotates toward medial region 511c.

Referring back to FIG. 6A, the computer-executable display instructions associated with block 604 may include, in some embodiments, various instructions configured to allow for variations in the viewable content of the graphical representation. The computer-executable display instructions associated with block 604 may include various instructions (e.g., computer-executable instructions associated with block 606) configured to allow for selective inclusions of the transducer graphical elements 502 and the selective inclusion of the between graphical elements 504 among the graphical representation 500. (In this regard, although block 606 is shown separately from block 604, block 606 may be a particular implementation of block 604 and such block may be combined into a single block.) In some example embodiments, the display instructions associated with block 606 may include instructions that allow for the selective inclusion of identification labels 513 that identify various ones of the transducer graphical elements 502. In various example embodiments, each of the identification labels 513 employs an alpha-numeric format including a letter representative of the column 512 in which a corresponding transducer graphical element is located and a number representative of a location of the transducer graphical element 502 in the corresponding column 514. Other identification schemes may be employed in other embodiments.

Figure 6A:
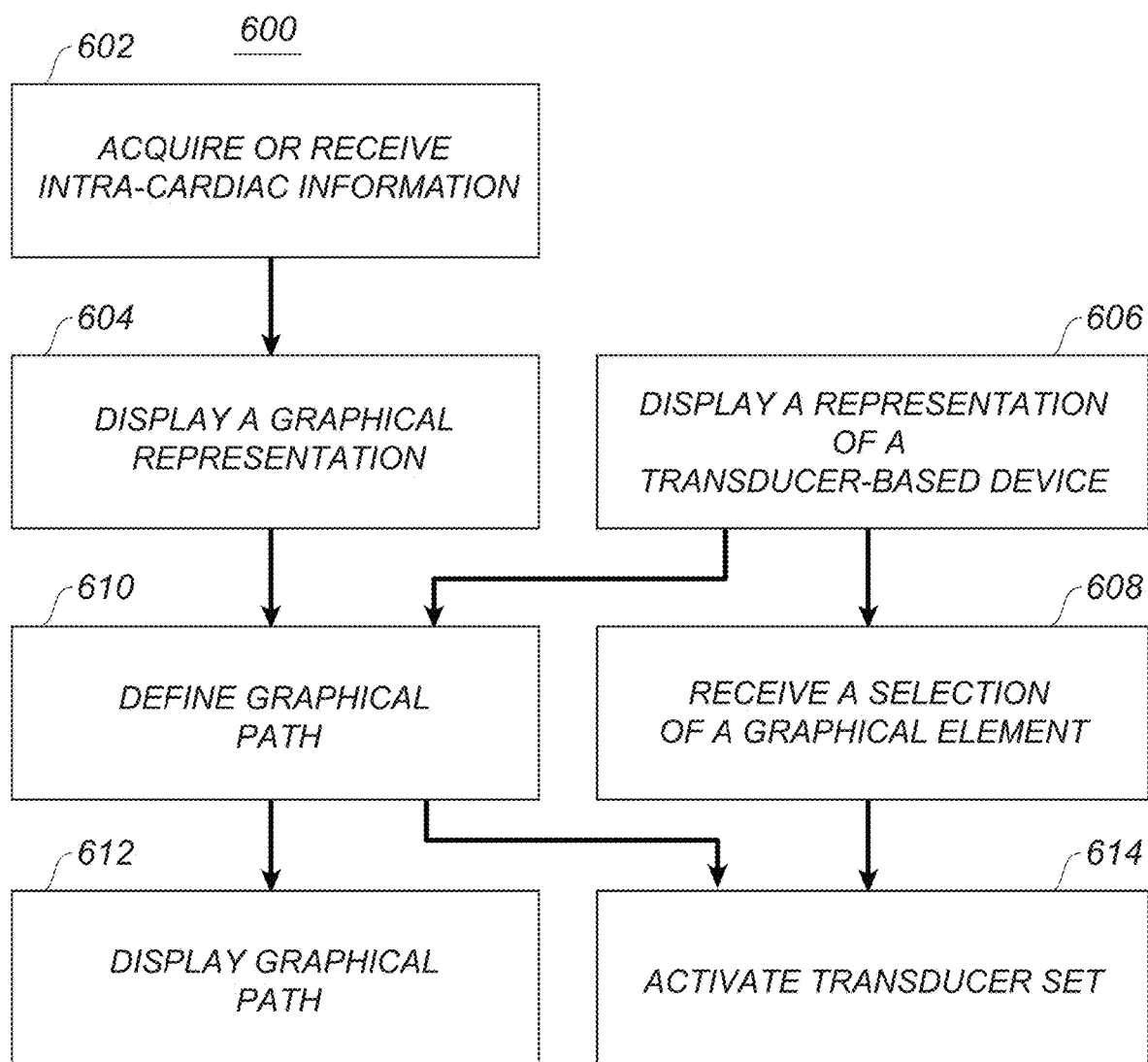

Having discussed embodiments associated with blocks 604 and 606 in FIG. 6A, a discussion will now begin regarding embodiments where block 604 follows block 602. (Recall that block 606 may be included within block 604 and the arrow from block 602 to 604 may also point toward block 606, in some embodiments.) Block 602, in some embodiments, is associated with instructions (e.g., input instructions included in a program) that cause the data processing device system (e.g., data processing device systems 110 or 310) to acquire or receive intra-cardiac information. Intra-cardiac information can take various forms, including, but not limited to, e.g., electrical information or a derivation thereof (e.g., electrical potential information, such as intra-cardiac electrogram information; electrical impedance information, such as fluidic or non-fluidic cardiac tissue impedance information; electrical conductivity information, such as fluidic or non-fluidic cardiac tissue electrical conductivity), thermal information or a derivation thereof (e.g., temperature information), fluid property information or a derivation thereof (e.g., blood flow information, blood pressure information), force information or a derivation thereof (e.g., contact information), and mapping information or a derivation thereof (e.g., electrical mapping; physical feature mapping, such as anatomical feature mapping). In various embodiments, intra-cardiac information may be related to any physiological parameter information related to a heart chamber. In various embodiments, intra-cardiac information may include any information related to, or resulting from an interaction with intra-cardiac tissue. By way of non-limiting example, interaction with intra-cardiac tissue may include an interaction made by way of a diagnostic procedure or treatment procedure.

Figure 6B:
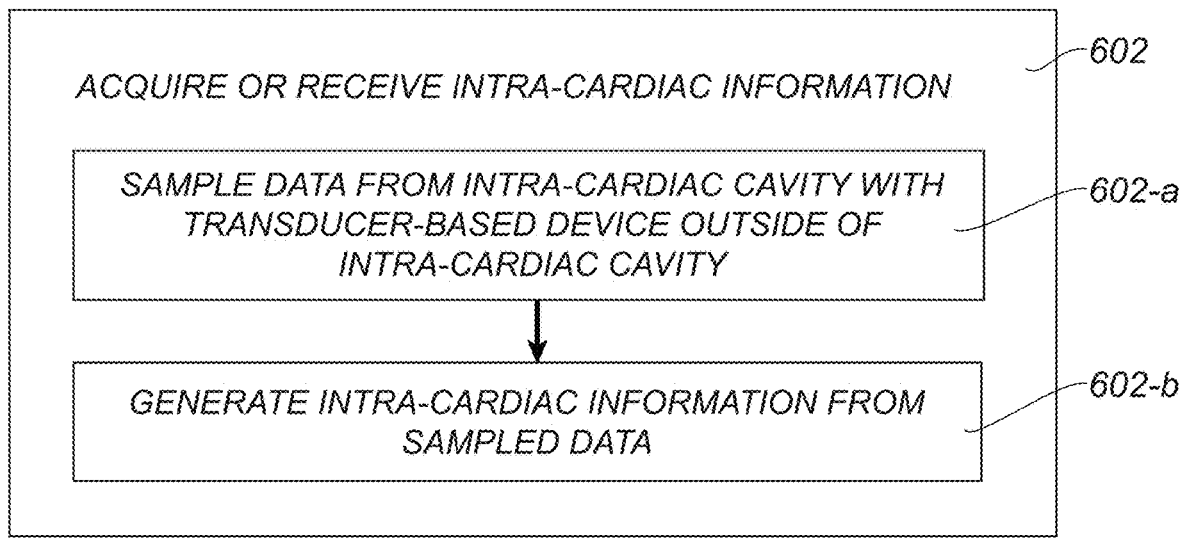

Intra-cardiac information may be acquired or received by various methods and from various device systems. For example, FIG. 6B shows an exploded view of block 602, according to some embodiments. In particular, FIG. 6B includes a sub-block 602-a associated with computer-executable instructions that receive or acquire the intra-cardiac information via data sampling performed by a transducer-based device system (e.g., which may be at least part of the data input-output device system 120, 320) deployed externally from an intra-cardiac chamber or cavity (e.g., outside the chamber or cavity or outside a body comprising the chamber or cavity). In this regard, the method 600 may include a sub-block 602-b in which the intra-cardiac information is generated (e.g., via generation instructions executable by a data-processing device system, e.g., 110, 310) from data provided or sampled (e.g., according to the computer-executable sampling instructions associated with block 602-a) by the transducer-based device system deployed externally from the intra-cardiac chamber or cavity. Such generation according to block 602-b, in some embodiments, may involve the associated instructions configuring the data processing device system (e.g., 110, 310) to recognize and identify (e.g., in memory device system 130, 330) the incoming sampled data or a derivation thereof as a set of respective intra-cardiac information (e.g., as an electrocardiogram or other form of intra-cardiac information discussed herein). By way of non-limiting example, various transducer-based device systems employed as per block 602-a may include various fluoroscopy device systems, ultrasound device system, magnetic resonance device systems, computerized tomography device systems, and transthoracic electrocardiographic mapping device systems. It is noted that some of the embodiments associated with block 602-*a* are considered to employ non-invasive methods or technologies.

Figure 6C:
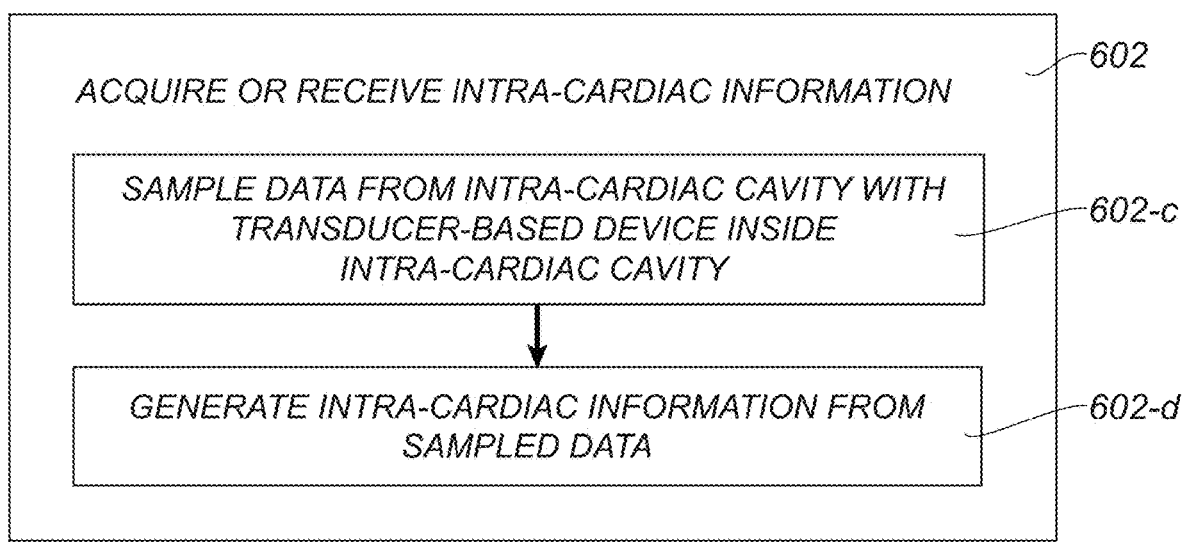
Figure 6D:
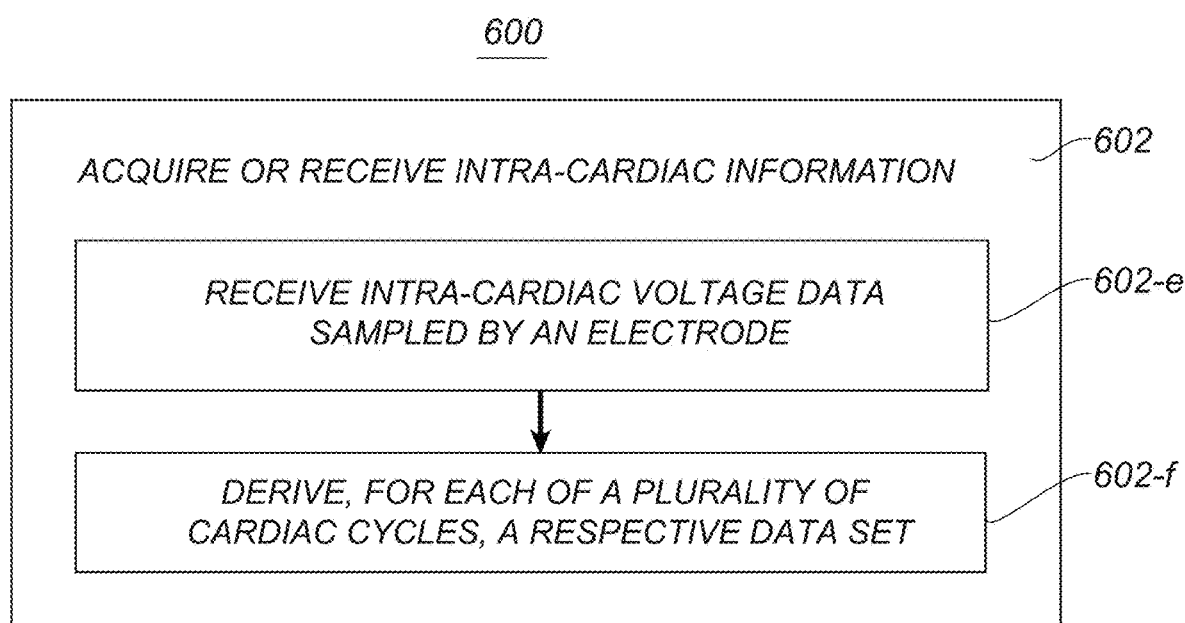

FIG. 6C shows an exploded view of block 602, according to some embodiments. In particular, FIG. 6C includes a sub-block 602-*c* associated with computer-executable instructions that are configured to cause reception or acquisition of the intra-cardiac information via data sampling performed by a transducer-based device system (e.g., which may be at least part of the data input-output device system 120, 320) deployed internally to an intra-cardiac chamber or cavity. In this regard, the method 600 may include a sub-block 602-*d* in which the intra-cardiac information is generated (e.g., via generation instructions executed by a data-processing device system (e.g., 110, 310) from data provided or sampled (e.g., by the sampling instructions associated with block 602-*c*) by the transducer-based device system deployed internally within the intra-cardiac chamber or cavity (e.g., inside the chamber or cavity). Such generation according to block 602-*d*, in some embodiments, may involve the associated instructions configuring the data processing device system (e.g., 110, 310) to recognize and identify (e.g., in memory device system 130, 330) the incoming sampled data or a derivation thereof as a set of respective intra-cardiac information (e.g., as an intra-cardiac electrogram or other form of intra-cardiac information discussed herein). By way of non-limiting example, various transducer-based device systems that may be internally deployed within an intra-cardiac chamber include by way of non-limiting example transducer-device systems 200, 300. Various transducer-based device systems employed as per block 602-*c* may include various intravascularly deployable or percutaneously deployable catheter device systems. Various transducer-based device systems employed as per block 602-*c* may include detection capabilities, mapping capabilities, diagnostic capabilities, treatment capabilities or any combination thereof. It is noted that some of the embodiments associated with block 602-*c* may be considered to employ invasive methods or technologies.

Referring back to FIG. 6A, the displaying of the graphical representation according to the computer-executable instructions associated with block 604 may in some embodiments, include causing displaying of a graphical representation of intra-cardiac information generated, acquired, or received according to the computer-executable instructions associated with block 602. Various embodiments may process or analyze (e.g., according to the instructions associated with block 604) the transducer data received by the data processing device system according to the computer-executable instructions associated with block 602 in order to, for example, generate and cause the displayed graphical representation 500 to include the intra-cardiac information. Various embodiments may process or analyze the transducer data received by the data processing device system according to the instructions associated with block 602 in order to, for example, generate and possibly cause the displayed graphical representation 500 to include a map of the intra-cardiac information. In various embodiments, the data is sampled by a transducer-based device system from a plurality of locations in a cardiac chamber and the generation instructions associated with block 602 cause mapping of each of a plurality of parts of the intra-cardiac information to a respective one of the plurality of locations in the cardiac chamber. In some of these various embodiments, the display instructions associated with block 604 are configured to cause an input-output device system (e.g., 120, 320) to display the plurality of parts of the intra-cardiac information with a first spatial relationship that is consistent with a second spatial relationship between the plurality of locations in the cardiac chamber (e.g., a map of the parts of the intra-cardiac information is displayed). In some embodiments, the transducer-based device includes a plurality of transducers (e.g., transducer-based device 200, 300) and the sampling instructions (e.g., 602-*c*) are configured to cause the sampled data to be sampled concurrently from the plurality of locations in the cardiac chamber.

It should be noted that some embodiments need not be limited to any particular form of processing or analysis of the transducer data received by the data processing device system according to the instructions associated with block 602. Although various display procedures can be implemented according to the computer-executable instructions associated with block 604 to display intra-cardiac information, these display procedures can be performed at other times, such as any time during the generation of or after the display of a graphical representation of at least a portion of a transducer-based device (e.g., as per the computer-executable instructions associated with block 606).

An example of a display of a graphical representation that at least depicts intra-cardiac information according to various embodiments (such as those represented by block 604 in FIG. 6A) would be a mapping locating the position of the ports of various bodily openings positioned in fluid communication with a cardiac chamber. For example, in some embodiments, it may be desired to determine intra-cardiac information indicating the locations of various ones of the pulmonary veins or the mitral valve that each interrupts an interior surface of an intra-cardiac cavity such as a left atrium.

In some example embodiments, the mapping is based at least on locating such bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling of heated transducer elements by fluid. A slightly heated arrangement of transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (e.g., force sensors). A set of force detection transducers positioned around the tissue that forms the interior surface of the bodily cavity and across the bodily openings or ports of the bodily cavity can be used to determine which of the transducers are not engaged with the tissue, which is indicative of the locations of the ports.

Figure 5G:
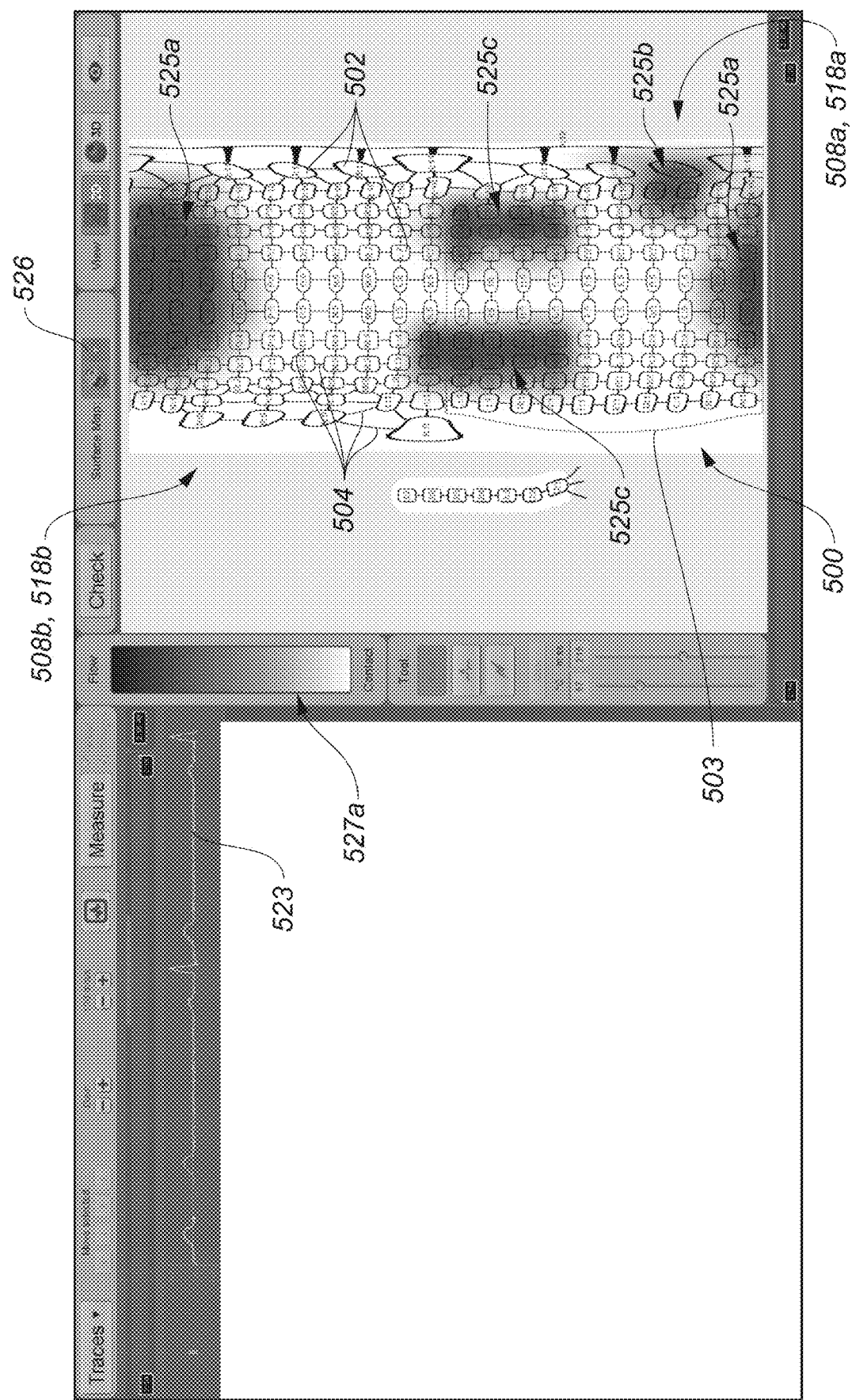
FIG. 5G includes an addition of various intra-cardiac information among the graphical representation of the transducer-based device illustrated in FIG. 5E in accordance with various example embodiments.

The graphical interface of FIG. 5G includes various regions 525a, 525b, and 525c (e.g., part of a plurality if regions collectively referred to as regions 525) added to the graphical representation 500 shown in FIG. 5E. The regions 525 could be displayed according to the instructions associated with block 604 in FIG. 6A in some embodiments. Although, such regions 525 could be displayed at other times or according to other instructions. In some embodiments, the graphical interface depicted in FIG. 5G is generated after the transducer-based device is received in a bodily cavity having various anatomical features of interest and the drop-down selection box 526 identified as "Surface Map" is activated via the input-output device system to select a mode referred to as "Flow". Techniques for flow-based mapping techniques are disclosed in commonly assigned U.S. patent Application Publication No.: US 2008/0004534. In various embodiments associated with various ones of FIGS. 5, the anatomical features of interest are ports of a mitral valve and various pulmonary veins positioned in fluid communication with an intra-cardiac cavity (e.g., a left atrium in some embodiments). In these various embodiments, the transducers of the transducer-based device are distributed adjacent respective regions in the intra-cardiac cavity that can include relatively lower blood flow regions (e.g., adjacent a tissue surface of the intra-cardiac cavity) and relatively higher flow regions (e.g., over the ports of the intra-cardiac cavity). It is noted that relatively lower blood flow regions in the intra-cardiac cavity may occur when a transducer is positioned in contact with a tissue surface to restrict blood flow at the contacted tissue. In some example embodiments, a relatively large number of transducers in the distribution advantageously allow for each of the transducers to be positioned adjacent their corresponding regions with little or no repositioning of the transducer-based device thereby facilitating an obtaining of transducer-based data concurrently from multiple locations in the bodily cavity.

Figure 5H:
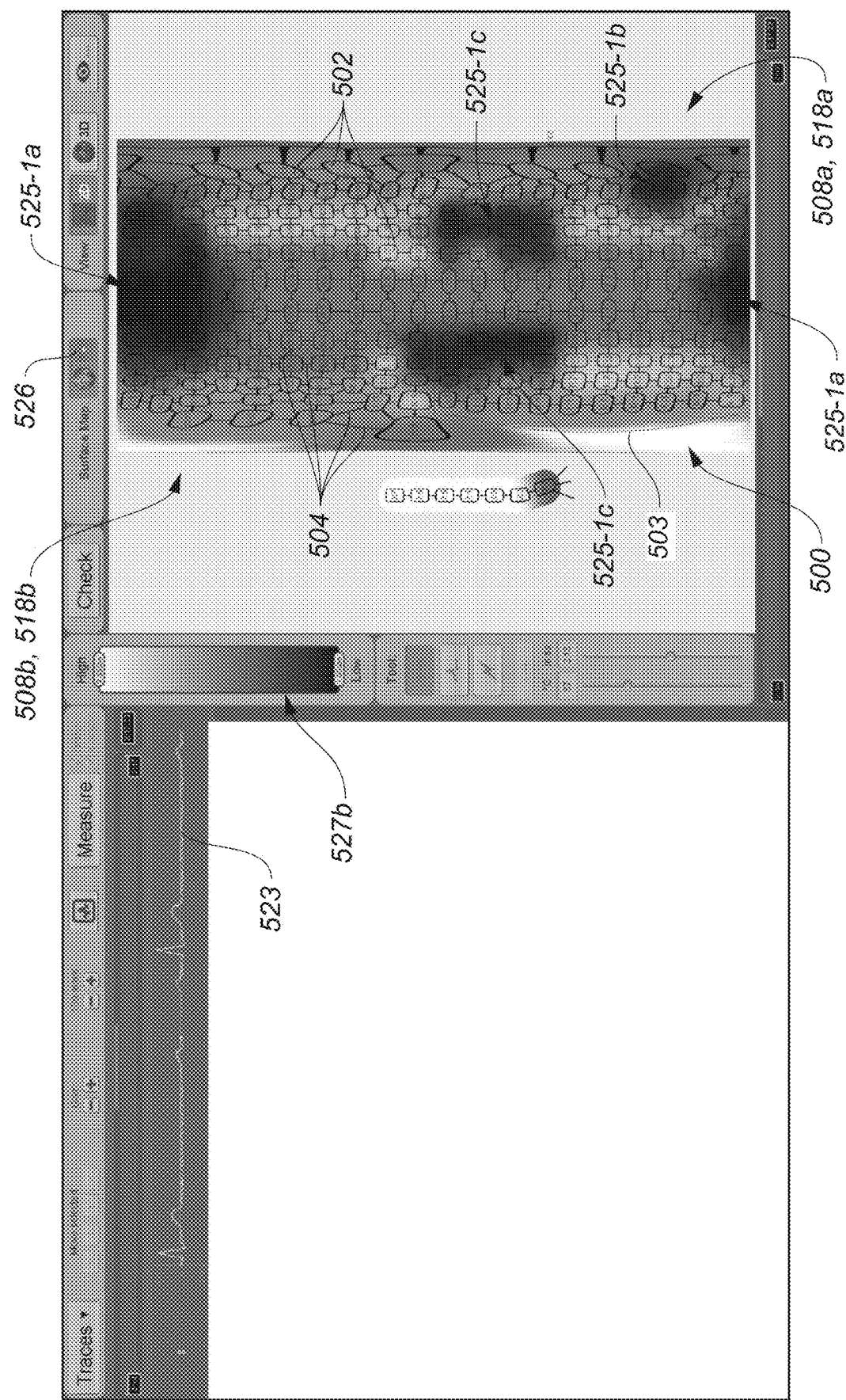
FIG. 5H includes an addition of various intra-cardiac information among the graphical representation of the transducer-based device illustrated in FIG. 5E, the intra-cardiac information representative of sampled intra-cardiac electrical data in accordance with various example embodiments.

One or more of the above-discussed mapping procedures may be implemented according to instructions associated with block 604 to display a graphical representation 500 that includes intra-cardiac information that indicates at least a portion of one or more anatomical features based at least on an analysis of the transducer data provided according to block 602. In some of these embodiments, the one or more anatomical features are the ports of various bodily openings (e.g., pulmonary veins, left atrial appendage, mitral valve) positioned in fluid communication with the intra-cardiac cavity and the transducer data includes data containing various blood flow data within the bodily cavity. In various embodiments, the data sampled according to block 602 is temperature data and the graphical representation 500 includes a graphical representation of at least some of the temperature data or a derivation thereof. For example, in various embodiments in which the use of convective cooling of heated transducer elements by fluid is employed to distinguish blood flow adjacent to the tissue that forms the interior surface(s) of a cardiac chamber from blood flow across the ports of the cardiac chamber, temperature data associated with the convective cooling can be sampled and displayed to provide the graphical representation of the intra-cardiac information. In FIG. 5G, the relatively large region 525a (e.g., shown as two parts in this particular orientation of the two-dimensional representation) is associated with the mitral valve, region 525b is associated with the left atrial appendage, and regions 525c are associated with various pulmonary vein groups. Each of the regions 525 is depicted in the graphical representation 500 with a graduated pattern provided by the flow identifier 527a in the graphical interface of FIG. 5G. In some embodiments, flow identifier 527a provides a graduated scale from a condition indicated as "Contact" (e.g., when a transducer is contact with cardiac tissue) to a condition indicated as "Flow" (e.g., when a transducer overlies a port in the cardiac chamber). A graduated pattern can be employed to indicate various regions in the graphical representation corresponding to different regions of flow in the intra-cardiac cavity. The identified regions 525 may be identified by any suitable methods including the use of gray-scale patterns, different colors, different opacities, different intensities and different shapes. It is understood that other embodiments may employ other techniques to identify regions in the graphical representation corresponding to a desired anatomical feature. For example, transducer-based data containing blood and tissue impedance information may be employed to determine regions 525 as shown in FIG. 5H. In various embodiments, drop-down selection box 526 may be operated to allow for the selective inclusion in the graphical representation of impedance data (e.g., tissue impedance data) or conductivity data (e.g., tissue conductivity data). In FIG. 5H, the relatively large region 525-1a (e.g., shown as two parts in this particular orientation of the two-dimensional representation) is associated with the mitral valve, region 525-1b is associated with the left atrial appendage, regions 525-1c are associated with various pulmonary vein groups. Each of the regions 525 is depicted in the graphical representation 500 with a graduated pattern provided by the impedance identifier 527b in the graphical interface of FIG. 5H. In some embodiments, impedance identifier provides a graduated scale from a condition indicated as "Low" (e.g., when a transducer overlying a port in the cardiac chamber is used to measure the electrical impedance of blood) to a condition indicated as "High" (e.g., when a transducer adjacent cardiac tissue is used to measure the electrical impedance of cardiac tissue). A graduated pattern can be employed to indicate various regions in the graphical representation corresponding to different regions of impedance in the intra-cardiac cavity. The identified regions 525 may be identified by any suitable methods including the use of gray-scale patterns, different colors, different opacities, different intensities, and different shapes. It is understood that other embodiments may employ other techniques to identify regions in the graphical representation corresponding to a desired anatomical feature.

Identification of the regions 525 may be motivated for various reasons. For example, in embodiments in which transducers of transducer-based device are activated to treat, diagnose, or investigate various regions in a bodily cavity, the identification of various regions 525 and their spatial relationship relative to one another may impact the efficacy of the treatment, diagnostic, or investigative procedure. For example, in situations in which at least some of the transducers of a transducer-based device are employed to ablate various regions within an intra-cardiac cavity (e.g., to treat atrial fibrillation), ablation of a pulmonary vein may result in an undesired condition referred to as pulmonary stenosis. Identification of various ones of the regions 525c (e.g., 525-1c) in the graphical representation along with their spatial relationship with various ones of the transducers at various times may be employed to reduce occurrences of this undesired condition.

Without limitation, other forms of intra-cardiac data (e.g., as received, acquired, provided, generated, or sampled per block 602) that may form part of the graphical representation 500 may include pressure data (e.g., blood pressure data, contact pressure data), electrophysiological activation timing data, isochronal data, propagation data, electrophysiological isopotential data, and other electrophysiological voltage data. Without limitation, various maps of intra-cardiac data may include tissue contact maps (e.g., contact maps inferred from flow data, impedance data, conductivity data), activation maps indicating the local activation times associated with a particular cardiac event, isochronal maps where contour lines may delineate regions of equal activation times associated with a particular cardiac event, propagation maps providing a dynamic representation of the moving activation wave-front associated with a particular cardiac event, isopotential maps, and various other voltage maps associated with intra-cardiac electrical activity. Various representations (e.g., maps) of intra-cardiac information may include portions corresponding to values measured at specific locations within an intra-cardiac cavity and portions corresponding to values that are interpolated (for example, interpolated from values measured at specific locations within an intra-cardiac cavity).

Figure 5I:
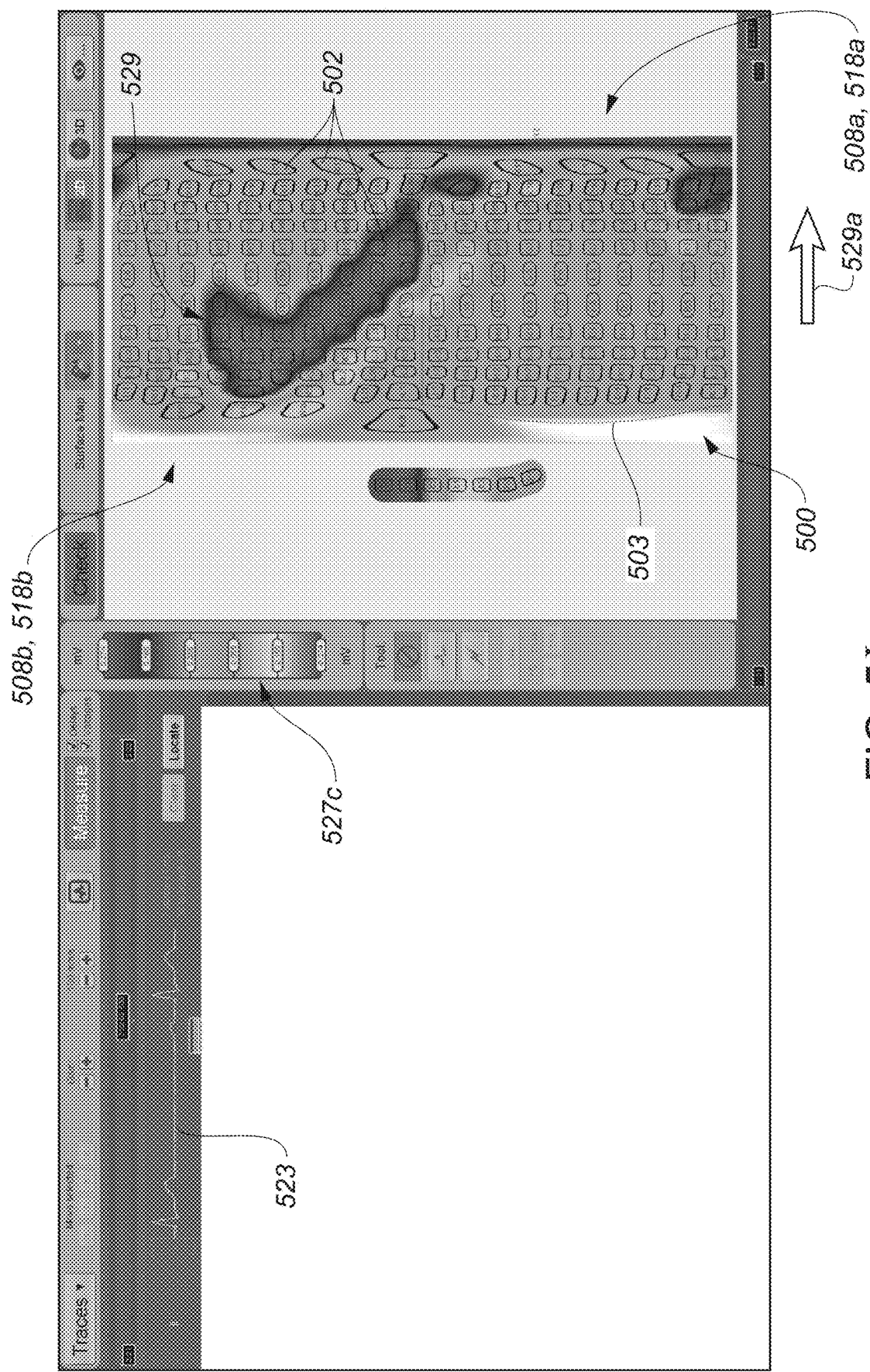
FIGS. 5I, 5J, and 5K include an addition of various intra-cardiac information among the graphical representation of the transducer-based device illustrated in FIG. 5E, the intra-cardiac information changing across three successive times represented by FIGS. 5I, 5J, and 5K, respectively, in accordance with various example embodiments.
Figure 5J:
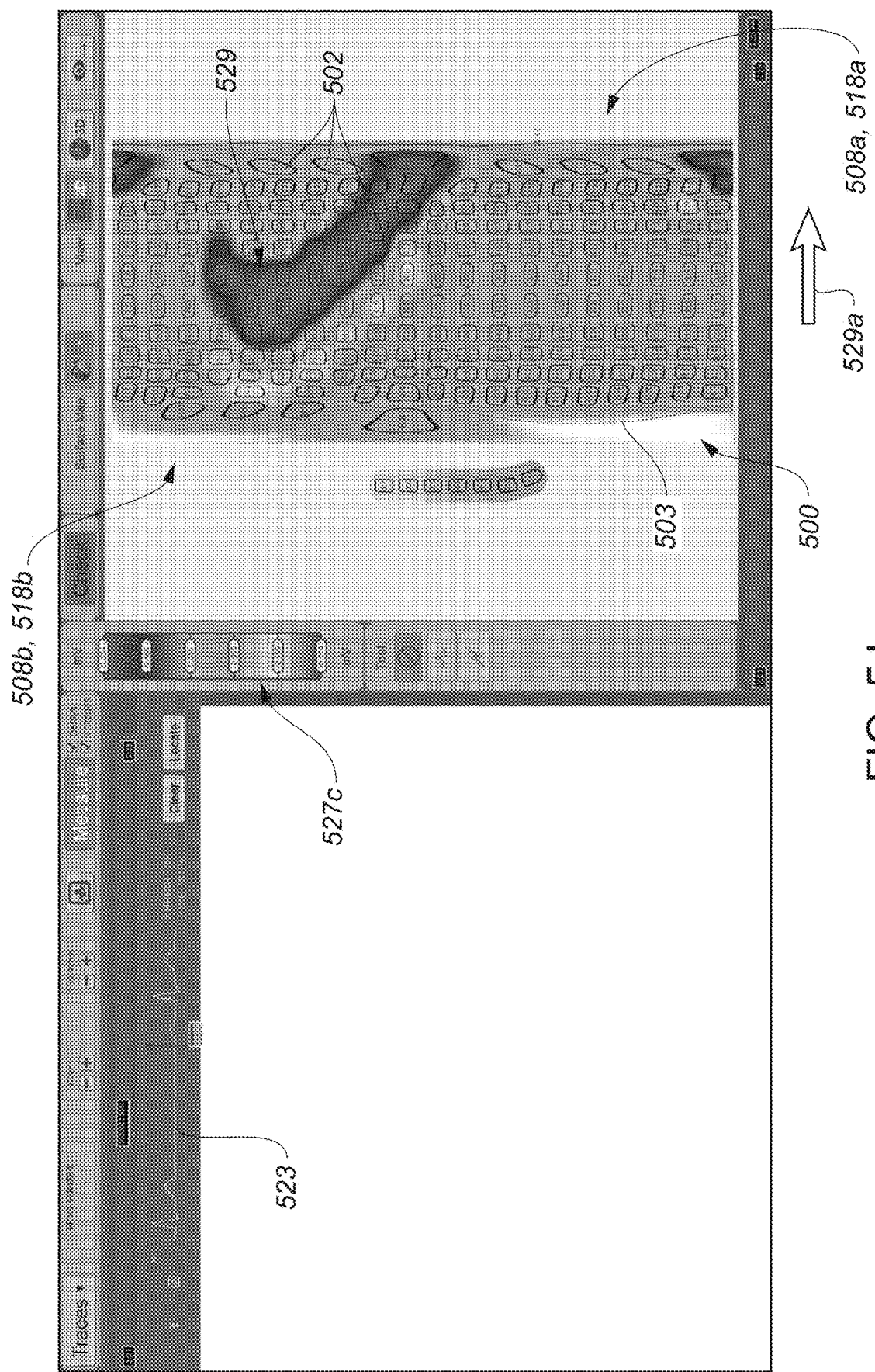
Figure 5K:
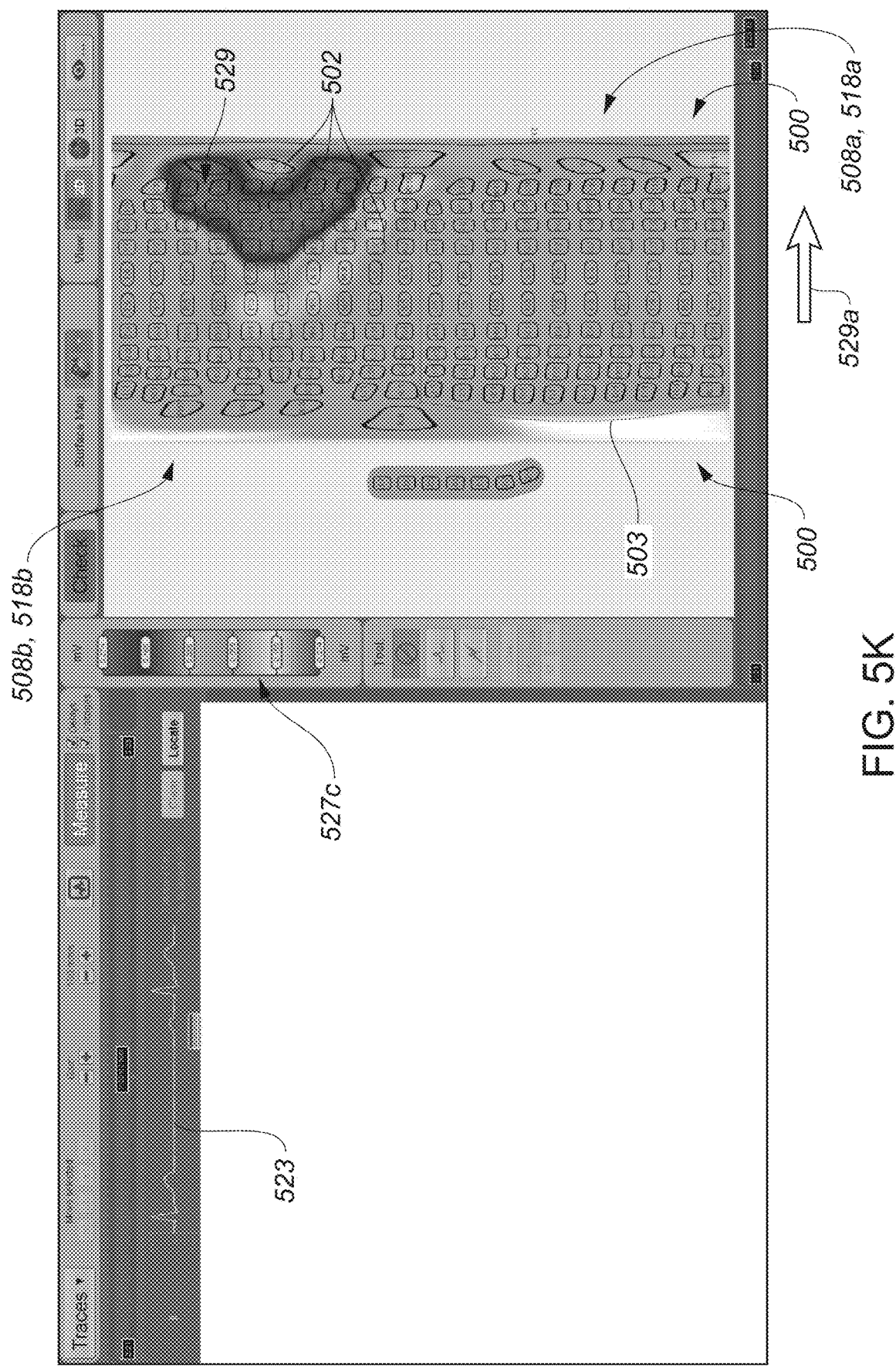

In some embodiments, intra-cardiac information is depicted in the graphical representation statically or relatively statically. That is, the displayed intra-cardiac data remains unaltered or relatively unaltered during a defined display period. In some embodiments, intra-cardiac information is depicted in the graphical representation 500 such that variances in the intra-cardiac information are shown occurring over a defined display period. In some embodiments, the graphical representation includes an animation of changes in intra-cardiac information. FIGS. 5I, 5J, and 5K show graphical representation 500 including changes in intra-cardiac information occurring at three successive particular times during a display period. In some embodiments, the intra-cardiac information displayed in each of FIGS. 5I, 5J, and 5K includes intra-cardiac voltage data showing a distribution of voltage values of intra-cardiac electrogram data sampled (e.g., using a transducer-based device system 200, 300) at a particular time (i.e., each of the FIGS. 5I, 5J, and 5K associated with a respective different particular time), each of the voltage values associated with intra-cardiac electrogram data or information sampled at the particular time at a respective one of a plurality of locations in an intra-cardiac cavity (e.g., by respective transducers).

In some embodiments, the displayed voltage values include positive values, negative values, or both positive and negative values. For example, various positive and negative voltage values are indicated in the graphical representation 500 shown in each of FIGS. 5I, 5J, and 5K, a magnitude and positive or negative indication varying in accordance with the voltage identifier 527c. The voltage values shown in FIGS. 5I, 5J, and 5K may be identified by any suitable methods including the use of gray-scale patterns, different colors, different opacities, different intensities, and different shapes. In some embodiments, a grey-scale or color-scale pattern extending across both a positive and negative range is employed to represent the various voltage values or ranges of voltage values. In various embodiments, at least some of the displayed voltage values may include a peak value corresponding to a peak amplitude portion of a waveform representative of the intra-cardiac electrogram data or information associated with the particular displayed voltage values. In various embodiments, at least some of the displayed voltage values may include a non-peak value corresponding to non-peak amplitude portion of a waveform representative of the intra-cardiac electrogram data or information associated with the particular displayed voltage values. Without limitation, various ones of the displayed voltage values may include derivations of the actual measured voltage values (e.g., values derived from the actual measured voltage values) including RMS values, peak-to-peak values.

In various embodiments, the sequence depicted in FIGS. 5I, 5J, and 5K shows time-varying changes in the voltage values associated with the intra-cardiac voltage data or information sampled at respective ones of a plurality of locations in an intra-cardiac cavity. By concurrently sensing intra-cardiac voltage data at each of plurality of locations within an intra-cardiac cavity at various successive times, a relationship indicating changes among all the voltage values associated the intra-cardiac voltage data or information sampled at various successive times across all of a plurality of locations in an intra-cardiac cavity is shown. For example, FIGS. 5I, 5J, and 5K include a depiction of various voltage values represented by moving wave-front 529 (sometimes referred to as propagation 529). In this case, the moving wave-front 529 of voltage values propagates generally in a direction indicated by arrow 529a (not part of the graphical representation 500 but provided to clarify the direction of propagation of wave-front 529 shown in the sequence depicted in FIGS. 5I, 5J, and 5K). It is understood that the propagation of the wave-front 529 of voltage values is not limited to the direction indicated by arrow 529a, but rather, is influenced by various physiological factors associated with the flow of various electrical signals within the cardiac tissue.

In some embodiments, the appearance of a propagating wave-front 529a is caused by changes in the voltage values at each of a plurality of locations in the graphical representation 500, the changes at each particular location represented by changes in a visual characteristic of the voltage value at that particular location. In this regard, an essentially real-time or quasi-real-time representation of the propagation of various electrical signals within an intra-cardiac cavity may be depicted.

It is noted that in various example embodiments such as those associated with various ones of FIGS. 5G, 5H, 5I, 5J, and 5K, at least some of the graphical elements 501 (e.g., transducer graphical elements 502, between graphical elements 504) are depicted as overlaid or superimposed on the displayed graphical representation 500 that includes a depiction of the acquired intra-cardiac information. In various embodiments, various ones of the graphical elements 501 (e.g., various ones of the transducer graphical elements 502) are depicted with a transparent, semi-transparent, or translucent appearance that allows a user to view regions of the intra-cardiac information that underlie each of the various ones of the graphical elements 501 or visual changes in the regions of the intra-cardiac information that underlie each of the various ones of the graphical elements 501. This configuration can be especially advantageous when one hundred, two hundred, or even more transducers are employed percutaneously to sample or gather the intra-cardiac information from a cardiac chamber. A graphical representation 500 that employs a similar, equal, or greater number of graphical elements 501 (e.g., transducer graphical elements 502, between graphical elements 504 or both transducer graphical elements 502 and between graphical elements 504) may obstruct a required viewing of the displayed intra-cardiac information, especially when transducer graphical elements 502 having a shape consistent with the shapes of corresponding ones of the transducers are employed or when transducer graphical elements having distorted appearances (e.g., enlarged distorted appearances described above) are employed. These situations may be effectively mitigated by the use of various graphical elements 501 having a transparent, semi-transparent, or translucent appearance.

Having described examples of the graphical representation displayed according to the instructions associated with block 604 in FIG. 6A, the definition of a graphical path (e.g., via input-output device system, 120, 320) according to some embodiments will be described with respect to block 610 in FIG. 6A. In various embodiments, the defined graphical path is depicted in the graphical representation 500, for example, among (a) the graphical elements 501, (b) the representation of the intra-cardiac information, or both (a) and (b). In various embodiments, the graphical path may be defined, at least in part, based on (a) a positional relationship between various ones of the graphical elements 501, (b) a positional relationship between various regions of the representation of the intra-cardiac information, (c) a positional relationship between various ones of the graphical elements 501 and various regions of the representation of the intra-cardiac information, or a combination of two or more of (a), (b) and (c).

The graphical path defined in accordance with the computer-executable instructions associated with block 610 may take various forms, shapes, or configurations including embodiments that include, by way of non-limiting example, an elongated portion, a continuous portion, an interrupted portion, a linear portion, an arcuate portion, a portion defining an obtuse angle, a portion defining an acute angle, a beginning portion (e.g., a portion defining or associated with a beginning or start of the definition of the graphical path), an end portion (e.g., a portion defining or associated with an end or termination of the definition of the graphical path), an open or closed circumferential portion, or any combination thereof. In various embodiments, a graphical path defined in accordance with the instructions associated with block 610 may include a plurality of graphical-path-elements. In various embodiments, a graphical path defined in accordance with the instructions associated with block 610 may include selection of some but not all of a plurality of selectable graphical-path-elements.

The definition of the graphical path in accordance with the instructions associated with block 610 may be accomplished at least in part by execution of various instructions by the data processing device system (e.g., exemplified by data processing device systems 110 or 310) responsive to various user instructions, inputs or actions. For instance, in some embodiments, a user instruction, input, or action may originate from a user selecting a particular region or regions of graphical representation 500. In this case, various instructions may configure the data processing device system to recognize this user instruction when it is received via an input-output device system (e.g., 110, 310) as a user instruction to form or define at least a portion of the graphical path. For example, user selection of a region 525c in FIGS. 5L and 5M may cause the data processing device system (configured according to the instructions associated with block 610) to define a graphical path 505 including transducer graphical elements 502 and between graphical elements 504 (shown, e.g., in solid-colored interior darkening) around such region 525c (e.g., by identifying transducers where the absolute value of the data, which causes region 525c, decreases to match the lighter colored regions in representation 500).

Definition of the graphical path may be motivated for different reasons. For example, in some embodiments, an activation (e.g., according to computer-executable instructions associated with block 614) of various transducer sets of a transducer-based device (e.g., 200, 300, or 400), initiated during or after the completion of the definition of the graphical path according to the instructions associated with block 610, may cause energy sufficient for tissue ablation along an ablation path corresponding to the defined graphical path. Advantageously in some embodiments, the ability to define a graphical path based at least on a graphical representation that includes at least a representation of intra-cardiac information may allow for enhanced results, or a possible reduction in undesired results during a subsequent ablation of cardiac tissue within an intra-cardiac cavity (e.g., an intra-cardiac cavity that is the source of the intra-cardiac information) when the graphical path acts as a template for a desired ablation path. In this regard, a desired ablation path may be defined based at least on a modeled graphical path that may be generated based at least on various possible constraints indicated by the graphical representation of the intra-cardiac information. For example, various representations of intra-cardiac information that indicate at least a portion of one or more anatomical features (e.g., various cardiac ports provided by the pulmonary veins, left atrial appendage, mitral valve as shown in FIGS. 5G and 5H by way of non-limiting example) may be used to assist a user in defining a graphical path that acts as a basis for a subsequent ablation path that takes into consideration (e.g., avoids) these anatomical features and reduce occurrences of undesired complications (e.g., stenosis which may arise if ablative energy is applied to particular ones of these anatomical features).

In various embodiments, the graphical representation 500 includes a representation of various transducers of a transducer-based device (e.g., 200, 300 or 400) positioned within the intra-cardiac cavity. For example, a mapping indicating a particular positioning, pose, or orientation of the transducer-based device in the intra-cardiac cavity, and in particular, a spatial positioning between various ones of the transducers and various regions of the depicted intra-cardiac information may be displayed. It is noted that in various embodiments, the intra-cardiac information that is displayed (e.g., via the instructions associated with block 604) need not be static and may include changes in the displayed appearance thereof, for example during the generation of the graphical path or thereafter. In some embodiments, the graphical representation 500 may form a basis for the definition of a particular graphical path that identifies particular ones of the transducers that may be suitable to ablate along an ablation path corresponding to the defined graphical path. Other motivations may drive the definition of the graphical path in other embodiments.

Figure 5L:
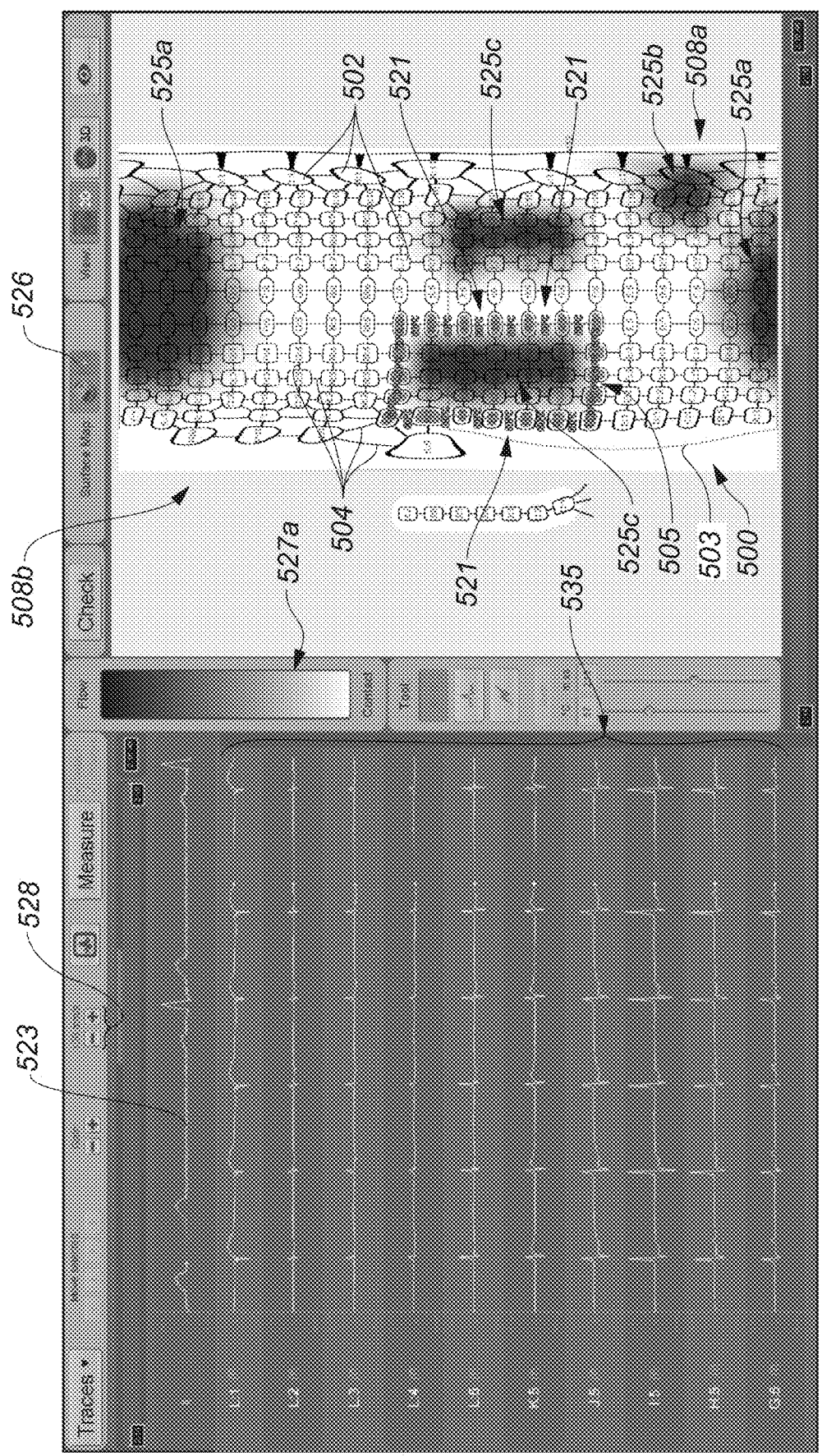
FIG. 5L includes a two-dimensional representation of a graphical path provided by a graphical interface, the graphical path including a selection of various graphical elements according to various example embodiments.
Figure 5M:
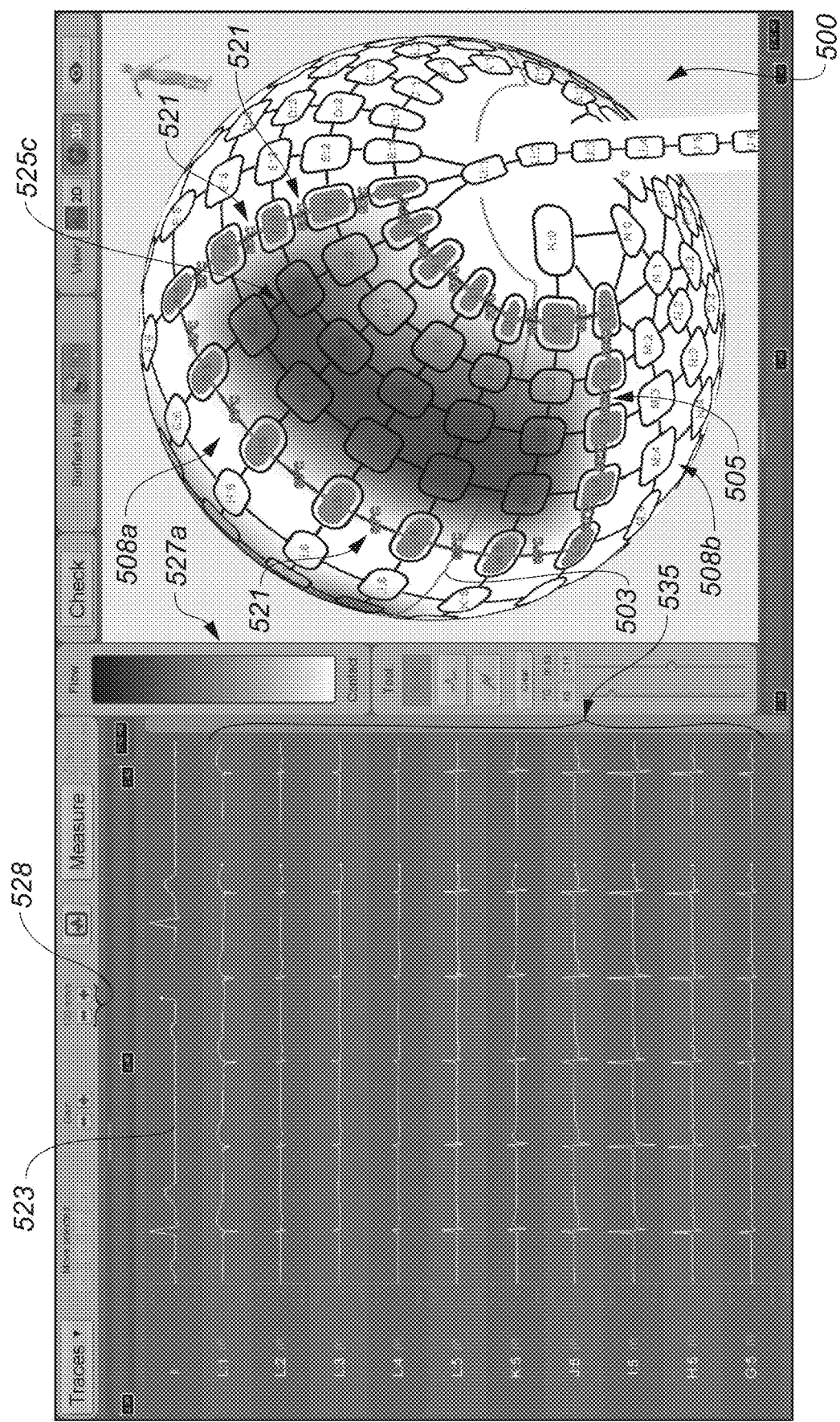
FIG. 5M includes a three-dimensional representation of a graphical path provided by a graphical interface, the graphical path including a selection of various graphical elements according to various example embodiments.

Block 612 in FIG. 6A may be associated with instructions configured to cause display of the graphical path (e.g., 505) defined according to the instructions associated with block 610. Such instructions may configure a data processing device system (e.g., 110, 310) to change a visual characteristic (e.g., changing a color or overlaying a graphical object on top) of at least part of each of at least some of the selected graphical elements in the graphical path (e.g., 505). For example, various ones of the particular illustrated embodiments shown in FIGS. 5L, 5M show a plurality of portions of a graphical path 505 displayed according to the instructions associated with block 612 as graphical elements 501 with solid-colored interior darkening, each selected portion of the graphical path 505 indicating a selection of at least one of the graphical elements 501. FIG. 5L shows at least a two-dimensional representation of the graphical path 505, while FIG. 5M shows at least a three-dimensional representation of the graphical path 505, according to various embodiments. In some embodiments, the graphical path displayed according to the instructions associated with block 612 is displayed among a graphical representation of intra-cardiac information. Such intra-cardiac information may include "flow-based" intra-cardiac information similar to or the same as that shown in FIG. 5G, as shown in each of FIGS. 5L and 5M, but it is understood that other forms of intra-cardiac information may be displayed in other embodiments. In some embodiments, various combinations of the display instructions associated with block 604, the display instructions associated with block 606, and the display instructions associated with block 612 are provided by a same set of display instructions.

In the particular illustrated embodiments shown in FIGS. 5L and 5M, additional information 521 is displayed upon a selection indicating a particular one of the graphical elements 501. In these particular embodiments, the information 521 includes target temperature information associated with each of the transducers corresponding to the particular ones of the directly or indirectly selected transducer graphical elements 502. In some embodiments, the information 521 is related to, or reflective of systems-based or hardware-based information. In some embodiments, the information 521 is related to, or reflective of physiological parameter information. In some embodiments, target temperature information may be employed to monitor or control the transmittance of tissue ablation energy from a particular one of the transducers. In various embodiments temperature data is sensed by a particular temperature sensor (e.g., temperature sensor 408) provided by a particular transducer. The temperature data may in some embodiments, be compared with the target temperature to monitor or control the transmittance of tissue ablation energy from the particular transducers. Other forms of information 521 may be displayed in other embodiments. It is noted that in some embodiments, the display of information 521 occurs in response to a selection of various ones of the graphical elements 501. Advantageously, the selective inclusion of information 521 only for the selected ones of the graphical elements 501 may reduce a cluttering the display region if the information 521 were provided for a significant number of (e.g., a majority) or all of the selectable graphical elements 501. This limited display of additional information 521 may be especially important when several hundreds of selectable graphical elements 501 are displayed.

In various embodiments, a plurality of graphical representations of electrograms 535 are additionally displayed (e.g., by the display instructions associated with block 604) by the graphical interface, each of the electrograms 535 derived from data sampled by a respective transducer (e.g., transducer 306, 406) corresponding to particular one of the transducer graphical elements 502 selected along the graphical path (e.g., 505). For example, the electrograms 535 in FIGS. 5L and 5M may be generated or derived according to the computer-executable instructions associated with block 602-d from intra-cardiac voltage data sampled in accordance with the computer-executable instructions associated with block 602-c. In various embodiments, each of the electrograms 535 is a unipolar or monopolar electrogram.

Returning to FIG. 6A, block 608 includes instructions configured to cause a reception of a selection of a graphical element, according to some embodiments. In some embodiments, the computer-executable instructions associated with block 608 are provided in a program that includes instructions configured to cause the data processing device system (e.g., 110, 310) to receive a selection from the input-output device system of a transducer graphical element (e.g., transducer graphical element 502), for example, to generate at least in part a graphical path (e.g., as per the instructions associated with block 610) similar to or the same as the graphical path 505 shown in FIGS. 5M and 5L. In this regard, although blocks 608 and 610 are shown separately in FIG. 6A, block 608 may be part of block 610, according to some embodiments. In some embodiments, the selection according to block 608 may occur by a user mouse-click or other user interface selection occurring at the display location of the graphical element or may occur by a user inputting (e.g., via a keyboard) an identifier (e.g., 513) associated with the selected graphical element. However, the invention is not limited to any particular manner of selecting a graphical element.

The selection of one or more graphical elements according to the instructions associated with block 608 in FIG. 6A may cause, in some embodiments, an activation of at least some transducer sets of a transducer-based device (e.g., 200, 300, or 400) according to instructions associated with block 614. In some embodiments, block 614 includes instructions configured to cause an activation of each of at least some of the transducer sets of the transducer-based device (e.g., again exemplified by transducer based devices 200, 300, or 400) in response to receiving a selection of a corresponding one of the graphical elements (e.g., graphical elements 501) in accordance with selection instructions included in block 608.

In some embodiments, the program may include activation instructions (e.g., in accordance with block 614) configured to, in response to receiving the selection (e.g., in accordance with block 608) of a transducer graphical element (e.g., transducer graphical element 502), cause, via the input-output device system, activation of the respective transducer of the transducer-based device corresponding to the selected transducer graphical element. In various embodiments, the instructions configured to activate the respective transducer corresponding to the selected transducer graphical element include instructions that are configured to cause energy from an energy source device system (e.g., energy source device system 340) to be delivered to the respective transducer, the energy sufficient for tissue ablation in some of these various embodiments. In some embodiments, a sensing device system (e.g., provided at least in part by a number of the transducers) is arranged to sense intra-cardiac information or physiological parameter information at a respective location at least proximate the respective transducer corresponding to the selected transducer graphical element with the energy delivered to the transducer. In some of these various embodiments, an indifferent electrode (e.g., indifferent electrode 326) is provided (e.g., usually to an external surface or skin-based surface of a body) while the transducer-based device is received in a bodily cavity within the body. A portion of the tissue-ablating energy delivered to the respective transducer corresponding to the selected transducer graphical element may be transmitted from the respective transducer to the indifferent electrode in a process typically referred to as monopolar ablation. Other forms of activation of the respective transducer corresponding to the selected transducer graphical element are possible in other embodiments. In some embodiments, activation of the respective transducer corresponding to the selected transducer graphical element under the influence of the instructions configured to activate the respective transducer is referred to as monopolar activation. Monopolar activation can include activation for monopolar ablation or monopolar electrogram generation by way of non-limiting example.

For another example, in some embodiments, the instructions associated with block 608 are provided in a program that includes selection instructions configured to cause, due to execution of the selection instructions by the data processing device system (e.g., again exemplified by data processing device systems 110 or 310), reception of a selection from the input-output device system of a between graphical element (e.g., between graphical elements 504). In accordance with the instructions associated with block 614 the program may include activation instructions configured to, in response to receiving the selection, cause activation, via the input-output device system, of a respective set of two or more of the transducers (e.g., a pair of the transducers in some embodiments) of the transducer-based device corresponding to the between graphical element.

Advantageously, activating a set of two or more of the transducers based on a selection of a single graphical element (e.g., between graphical element 504) provides for a workflow that is less cumbersome and more expeditious than individually selecting the respective graphical elements (e.g., transducer graphical elements 502) associated with each transducer of the set of two or more of the transducers, especially when 50, 100, 200 or even over 300 or more transducer graphical elements are provided in the graphical representation. This is even more advantageous, when a single graphical element (e.g., between graphical element 504) provides additional information (e.g., spatial information) relating each of the transducers in the set of two or more of the transducers. For example, a between graphical element 504 can indicate a distance between or acceptability-of-activation of transducers of a corresponding transducer pair, and, accordingly, the between graphical element 504 provides, in some embodiments, information about the corresponding group (e.g., pair) of transducers and, thereby, makes the selection process more efficient. In addition, allowing selection of the between graphical elements for corresponding transducer activation can provide a more intuitive user-interface in certain applications. For example, such an arrangement allows a user to make selections along an ablation path or a path along which data is to be obtained, without having to focus on the transducers required to make that ablation path or acquire that data. The user can, for example, just select a path using between graphical elements (e.g., user-based selection(s)/constituent selection(s)), and the corresponding transducers are automatically selected (e.g., machine-based selection(s)/constituent selection(s)) in response. Since various ones of the between graphical elements need not be tied to any physical portion of the transducer-based device, they can be freely designed to reflect the path (e.g., over tissue or fluid) in which their corresponding transducers will interact when activated (e.g., by causing ablation or gathering data). In this regard, if the between graphical elements are configured to accurately represent their respective path segments in which ablation or data gathering will occur, according to some embodiments, the user can gain an even better understanding of the expected results of activation of the corresponding transducers. This advantageously increases the likelihood that an ablation path that is consistent with a displayed graphical path will result in various embodiments.

In various embodiments where the instructions according to block 614 are configured to cause a data processing device system to activate a respective set or group of two or more of the transducers, the instructions according to block 614 include instructions that are configured to cause energy from an energy source device system (e.g., energy source device system 340) to be delivered to the respective set of two or more of the transducers, the energy sufficient for tissue ablation in some of these various embodiments. In some embodiments, a sensing device system (e.g., sensing device system 325) is arranged to sense at least one tissue electrical characteristic (e.g., an example of intra-cardiac information) at respective locations at least proximate each transducer of the respective set or group of two or more of the transducers with the energy delivered to the respective set of two or more of the transducers. In some example embodiments, a selected between graphical element (e.g., between graphical element 504) is representative of a physical path extending between a respective pair of the transducers associated with the selected between graphical element and the energy is sufficient for ablating a portion of tissue extending along the physical path. A portion of the tissue-ablating energy may be transmitted between the respective pair of the transducers in a process typically referred to as bipolar ablation. In some embodiments, an indifferent electrode (e.g., indifferent electrode 326) is provided (e.g., usually to an external surface or skin-based surface of a body) while the transducer-based device is received in a bodily cavity within the body. Some of the tissue-ablating energy may be transmitted between the respective pair of the transducers while some of the tissue-ablating energy may be transmitted from various ones of the respective pair of the transducers to the indifferent electrode in a process typically referred to as blended monopolar-bipolar ablation. The term "bipolar ablation" as used in this disclosure is to be interpreted broadly to include blended monopolar-bipolar ablation in some embodiments.

In addition to embodiments where the instructions according to block 614 are configured to cause a data processing device system to cause bipolar ablation, the instructions according to block 614, in some embodiments, are configured to cause a data processing device system to cause multi-transducer monopolar ablation with the respective set of two or more of the transducers, e.g., dual monopolar ablation for two transducers, or triple monopolar ablation for three transducers. In such cases, for example, the respective set of two or more of the transducers may be 'queued' for monopolar ablation, such that monopolar ablation occurs for each transducer in the respective set of two or more of the transducers within some period of time, but not necessarily at the same time or even contiguously one right after another. In this regard, references herein to the occurrence of monopolar ablation for more than one transducer may include this multi-transducer monopolar ablation according to some embodiments. In addition, any reference herein to the occurrence of bipolar ablation may be replaced with the occurrence of dual monopolar ablation (or other multi-transducer monopolar ablation when more than two transducers are involved), according to some embodiments. In some cases in which multi-monopolar ablation is employed, energy transfer sufficient to cause tissue ablation is not transferred between the particular transducers employed by the multi-monopolar ablation. Rather, in these cases energy sufficient for tissue ablation is transmitted between each of these particular transducers and an indifferent electrode (e.g., indifferent electrode 326). In various embodiments, the activation instructions associated with block 614 may be configured to cause transmission, initiated during or after completion of the definition of the graphical path (e.g., graphical path 505) of energy sufficient for tissue ablation from at least each respective transducer corresponding to each transducer graphical element (e.g., 502) selected, indicated or passed through by the graphical path defined in accordance with the computer-executable instructions associated with block 610. In some embodiments, the computer-executable instructions associated with block 614 that are, in some embodiments, configured to activate the respective transducer corresponding to the selected transducer graphical element include instructions that are configured to cause a sensing device system (e.g., sensing device system 325) to detect, sense or sample electrophysiological data including intra-cardiac voltage data (an example of intra-cardiac information in some embodiments) at a location in a bodily cavity or chamber at least proximate the respective transducer. The detected electrophysiological activity can be displayed as an intra-cardiac electrogram via the input-output device system (e.g. electrograms 535 shown in FIGS. 5L and 5M). In some embodiments, detection of electrophysiological activity in an intra-cardiac cavity at a location at least proximate various ones of the transducers occurs continuously and is not necessarily dependent on a particular selection of a graphical element 501.

Figure 7A:
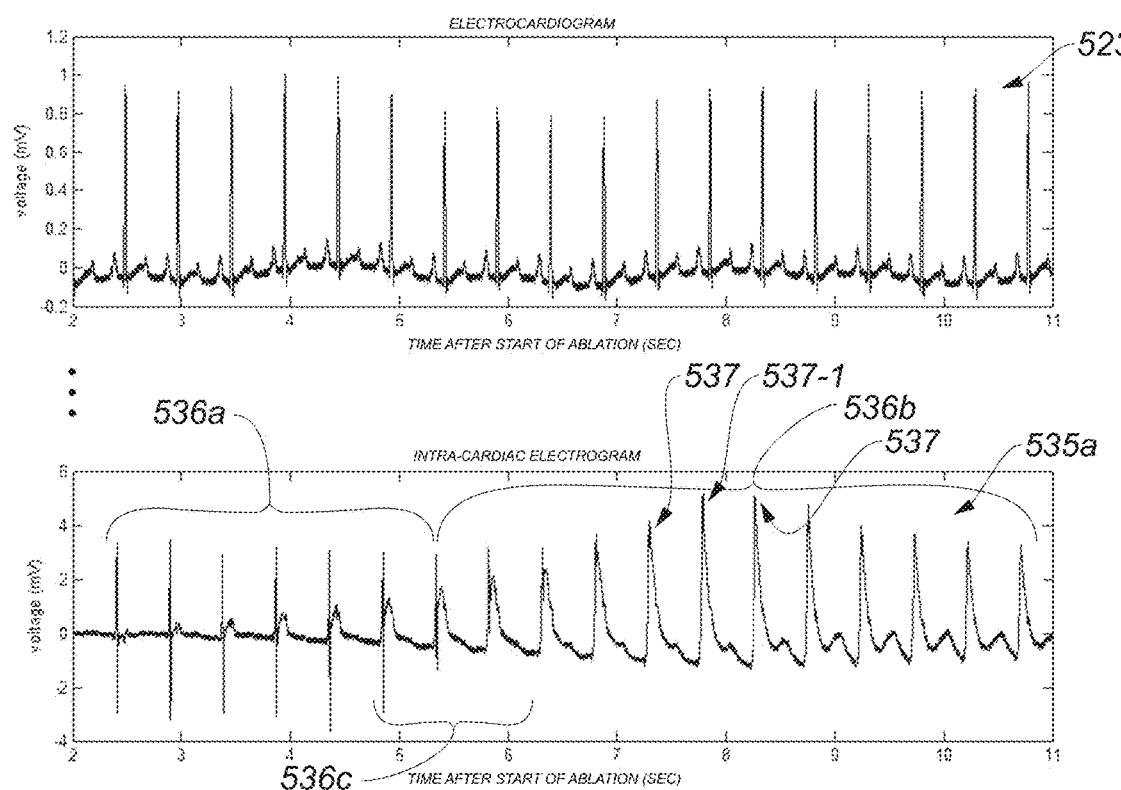
FIG. 7A includes a view of an intra-cardiac electrogram spanning a period of time that commences after a start of a tissue ablation procedure according to some embodiments.

In some embodiments, the detected, sensed, or sampled intra-cardiac information (e.g., sampled intra-cardiac voltage data) is employed to assess various levels of lesion (e.g., an ablated tissue region) transmurality achieved at various times during a tissue ablation process (e.g., a cardiac tissue ablation process). For example, FIG. 7A shows an example intra-cardiac electrogram 535a during a cardiac tissue ablation procedure, which may be displayed, e.g., as part of the graphical representations of any of FIG. 5 (e.g., as at least part of one of the subpanels displaying one or more graphical representations of at least one of the intra-cardiac electrograms 535 shown in the panel of intra-cardiac electrograms displayed by the graphical representation in FIGS. 5L and 5M). In FIG. 7A, the cardiac tissue ablation procedure is performed by transmitting RF ablation energy via one particular transducer electrode (e.g., a particular electrode 315, 415) during the generation of the intra-cardiac electrogram 535a. In this particular case, the cardiac tissue ablation procedure is performed by transmitting RF ablation energy (e.g., energy sufficient to cause tissue ablation) via one particular transducer electrode (e.g., a particular electrode 315, 415) during the sampling of intra-cardiac voltage data from which the intra-cardiac electrogram 535a is derived. In some embodiments, the displayed intra-cardiac electrogram 535a data is provided from data sampled during a time period starting when or after the ablation of the cardiac tissue begins. Changes in the intra-cardiac electrogram data throughout the time period are displayed as the cardiac tissue ablation procedure proceeds. In some embodiments, the same electrode that is employed to perform the cardiac tissue ablation is employed to sample the intra-cardiac voltage data. In other cases, a transducer other than a transducer employed to perform the tissue ablation may be employed to sample the intra-cardiac voltage data (e.g., the sampling or sensing transducer electrode is distinct from the ablation transducer or electrode). In some embodiments, a same electrode is employed to concurrently sample and ablate the cardiac tissue (e.g., the sampling or sensing transducer electrode is the ablation transducer or electrode). It is noted, however, that intra-cardiac data may be sampled by a transducer other than an ablation transducer in other cases (for example, a sampling by an intra-cardiac voltage sampling transducer at a location at least proximate a tissue ablated by an ablation transducer). In some embodiments, intra-cardiac voltage data is sampled by an electrode while the electrode is positioned at a same location in an intra-cardiac cavity throughout a tissue ablation period that can encompass a plurality of cardiac cycles. An electrocardiogram (ECG/EKG) 523a may also be additionally provided (e.g., by the graphical interface shown in various ones of FIG. 5) to further interrelate various portions of the intra-cardiac electrogram 535a to various cardiac cycles or portions thereof as described below. Electrocardiograms provide an interpretation of the electrical activity of the heart over a time period. Electrocardiograms are detected by electrodes attached to an external or skin-based surface of the body and are recorded or displayed by a device external to the body. In this regard, electrocardiograms are generated transthoracically (i.e., across the thorax or chest).

Unlike electrograms provided by various conventional systems, electrogram 535a has a particularly well established form with relatively low noise that is typically characteristic of the electrograms provided by the various transducer-based device systems disclosed herein due at least to the structure of the transducers described according to FIG. 4, above. In this particular case, electrogram 535a includes a biphasic portion 536a (e.g., an electrogram portion that contains both positive and negative voltage peaks) during the early phases of the cardiac ablation procedure. It is noted that that electrogram 535a is typically biphasic in nature prior to ablation. The present inventors have noted, however, that the biphasic portion 536a is typically transient in nature during the actual ablation and transitions into monophasic portion 536b (e.g., an electrogram portion that contains or primarily contains either only positive voltage peaks or only negative voltage peaks or contains only positive voltage peaks that are much greater than the absolute value of the negative voltage peaks (e.g., at least two, three, or four times greater)). In this regard, it is noted that the transformation from the biphasic portion 536a to the monophasic portion 536b occurs over a plurality of cardiac cycles (shown approximately by reference numeral 536c for the embodiments of FIG. 7A, but other durations of transformations will occur depending upon at least ablative energy delivery characteristics and tissue characteristics). The present inventors have further noted that the various monophasic peaks in the monophasic portion 536b increase in amplitude and reach a maximum value (e.g., maximum peak 537-1), then reduce in amplitude, and eventually plateau as the ablation progresses, as described below in detail with respect to FIG. 7.

Figure 7B:
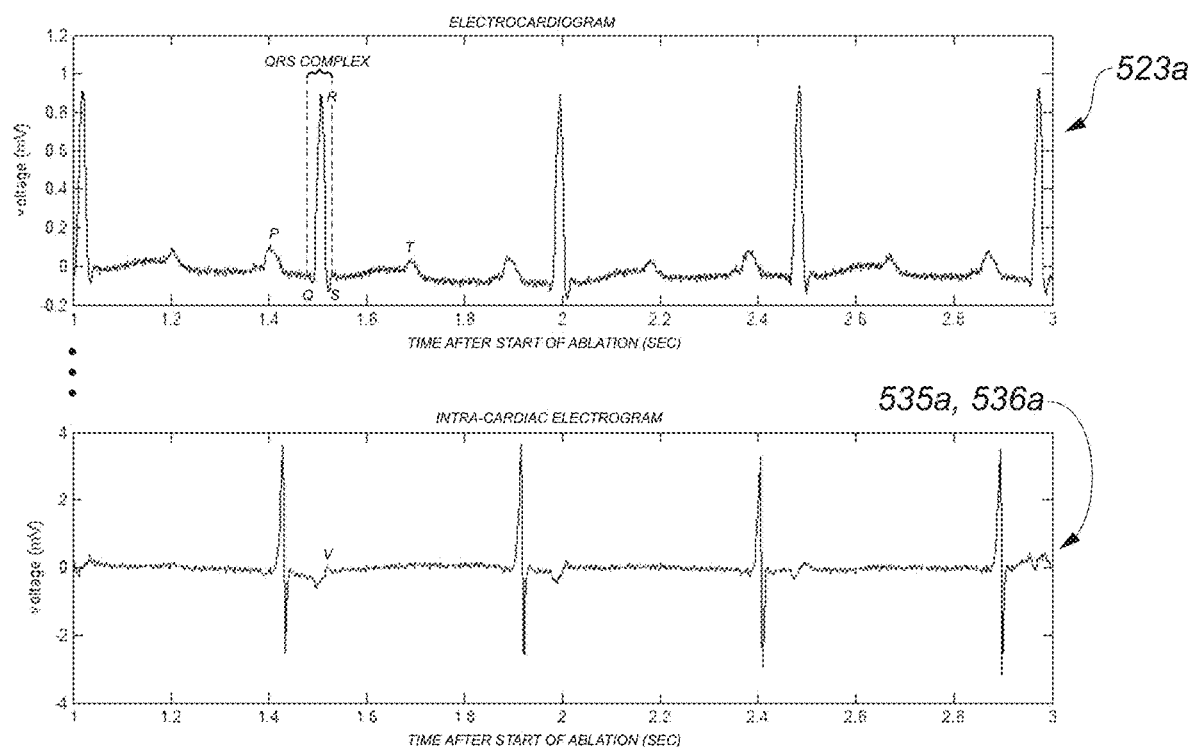
FIGS. 7B, 7C, and 7D include portions of the intra-cardiac electrogram of FIG. 7A at three successive times during the period of time displayed according to some embodiments.
Figure 7C:
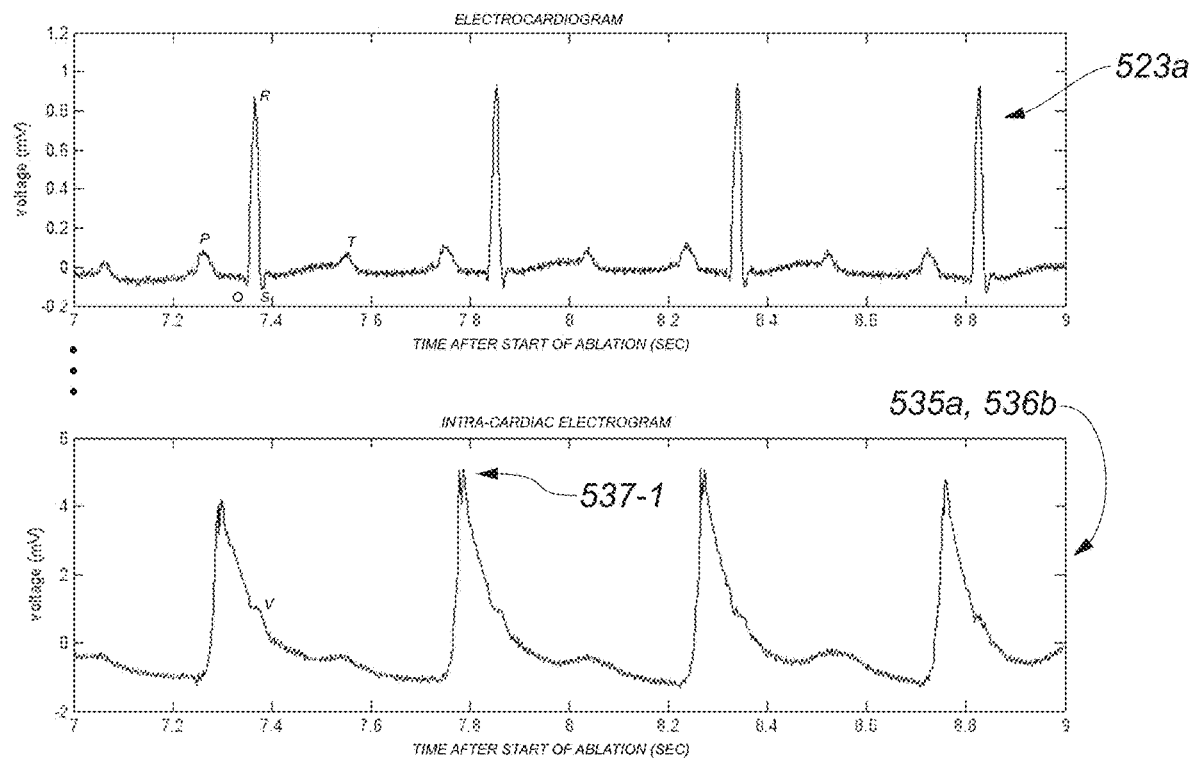
Figure 7D:
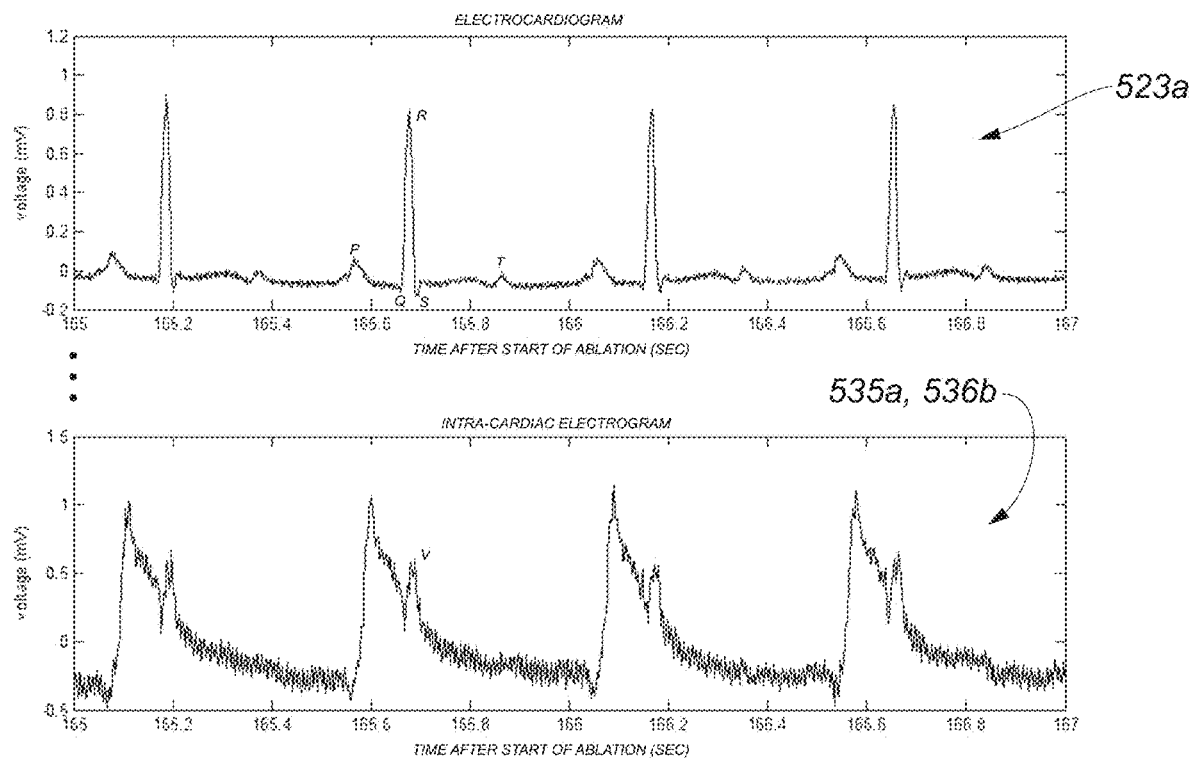

For clarity, FIGS. 7B, 7C, and 7D are provided to show detailed portions of intra-cardiac electrogram 535a during different times during the cardiac tissue ablation procedure that spans a plurality of cardiac cycles. As employed herein, the phrase "cardiac cycle" refers to a time period of a complete heartbeat from its generation to the beginning of the next beat, and includes the diastole, the systole, and an intervening pause. A frequency of the cardiac cycle is described by the heart rate, which is typically expressed as beats per minute. Diastole represents the period of time when the ventricles are relaxed (e.g., not contracting). During diastole, blood is passively flowing from the left atrium and right atrium into the left ventricle and right ventricle, respectively. The blood flows through the mitral and tricuspid valves (also known as the atrioventricular valves) separating the atria from the ventricles. The right atrium receives blood from the body through the superior vena cava and inferior vena cava. The left atrium receives oxygenated blood from the lungs through four pulmonary veins that enter the left atrium. At the end of diastole, both atria contract, propelling blood into the ventricles. Systole occurs when the left and right ventricles contract and eject blood into the aorta and pulmonary artery, respectively. During systole, the aortic and pulmonic valves open to permit ejection into the aorta and pulmonary artery. The atrioventricular valves are closed during systole, therefore no blood is entering the ventricles; however, blood continues to enter the atria though the vena cava and pulmonary veins. Throughout the cardiac cycle, blood pressure increases and decreases. The cardiac cycle is coordinated by a series of electrical impulses that are produced by specialized heart cells found within the sinoatrial node and the atrioventricular node.

Each of FIGS. 7B, 7C, and 7D include respective portions of the electrocardiogram (ECG/EKG) 523*a* of FIG. 7A occurring during the respective times associated with each of the respective figures. It is noted that the various information (e.g., X axis and Y axis headers, scales) may not be present in the actual content displayed (e.g., via a respective subpanel in one or more of FIG. 5), but are included herein for the convenience of discussion. Typically, an electrocardiogram (e.g., 523, 523*a*) has five deflections or peaks identified as the P wave, Q wave, R wave, S wave, and T wave, the deflections or peaks collectively marking a cardiac cycle. It is noted that a U Wave (not identified in FIGS. 7B, 7C and 7D) may follow the T wave in the cardiac cycle, but such U wave is typically of low amplitude and may not be visible in various electrocardiograms. The Q, R, and S waves generally occur in rapid succession, and the combination of three of these waves is typically referred to as the QRS complex. The QRS complex generally corresponds to the depolarization of the right and left ventricles of the heart, and at least the R wave thereof is readily visible in electrocardiograms. The P wave marks a deflection in the electrocardiogram produced by excitation of the atria of the heart, while the T wave represents the repolarization (or recovery) of the ventricles in the electrogram. Ventricular systole begins at the QRS complex, and atrial systole begins at the P wave.

A V wave in the electrogram 535*a* typically corresponds to the ventricular depolarization corresponding to at least the R wave portion of the QRS complex in the electrocardiogram 523*a*. The V wave is typically not as pronounced or prominent in intra-cardiac electrograms as the R wave is in electrocardiograms. A magnitude of the V wave may vary from electrogram to electrogram when each electrogram is derived from respective data sampled from a respective different location within an intra-cardiac cavity. It is understood that the indication of the P wave, Q wave, R wave, S wave, T wave, and V wave in various ones of FIG. 7 are provided for convenience of discussion and may not actually form part of the display of the respective electrocardiogram or the display of the respective intra-cardiac electrogram as the case may be.

FIG. 7B includes a display of at least part of the biphasic portion 536*a* of intra-cardiac electrogram 535*a* (e.g., as displayed by the graphical interface of FIG. 5). Little changes in the amplitude and other characteristics of the peaks of the biphasic pulses in portion 536*a* appear during this time in the ablation procedure. FIG. 7C includes at least part of the monophasic portion 536*b* of intra-cardiac electrogram 535*a* including peak 537-1. In this particular case, peak 537-1 has an amplitude of approximately 5 millivolts and occurs approximately 7.8 seconds after the start of the tissue ablation, although the invention is not limited to such amplitude and timing, which depend on many factors, such as tissue thickness, ablation energy, ablation-electrode-to-tissue-contact, etc. Peak 537-1 marks an occurrence of a particular situation in which the intra-cardiac electrogram 535*a* (and, in particular, the monophasic portion 536*b*) reaches a maximum voltage value or a maximum amplitude. Peak 537-1 marks an occurrence of a particular situation in which the amplitude of a peak 537 of a portion of the intra-cardiac electrogram 535*a* (and, in particular, the monophasic portion 536*b*) derived from data sampled during a particular cardiac cycle during the ablation reaches an overall maximum value or peak value as compared with the amplitudes of the respective peaks of other portions of the intra-cardiac electrogram 535*a* that are derived from data sampled during the other cardiac cycles occurring during the ablation. It is noted that, in some embodiments, intra-cardiac electrogram 535*a* may be considered to be a monophasic intra-cardiac electrogram according to definitions set forth above with respect to monophasic portion 536*b*.

FIG. 7D includes at least part of the monophasic portion 536*b* of intra-cardiac electrogram 535*a* in which an amplitude of various ones of the monophasic pulses has plateaued and reached a voltage value of approximately 1 millivolt which remains relatively constant (e.g., +/−15% or +/−0.3 millivolts in some embodiments) during this time in the tissue ablation. The indicated time in FIG. 7D spans a range of 165 to 167 seconds after the start of the ablation, although the invention is not limited to the plateau region occurring within such a time span.

Figure 7E:
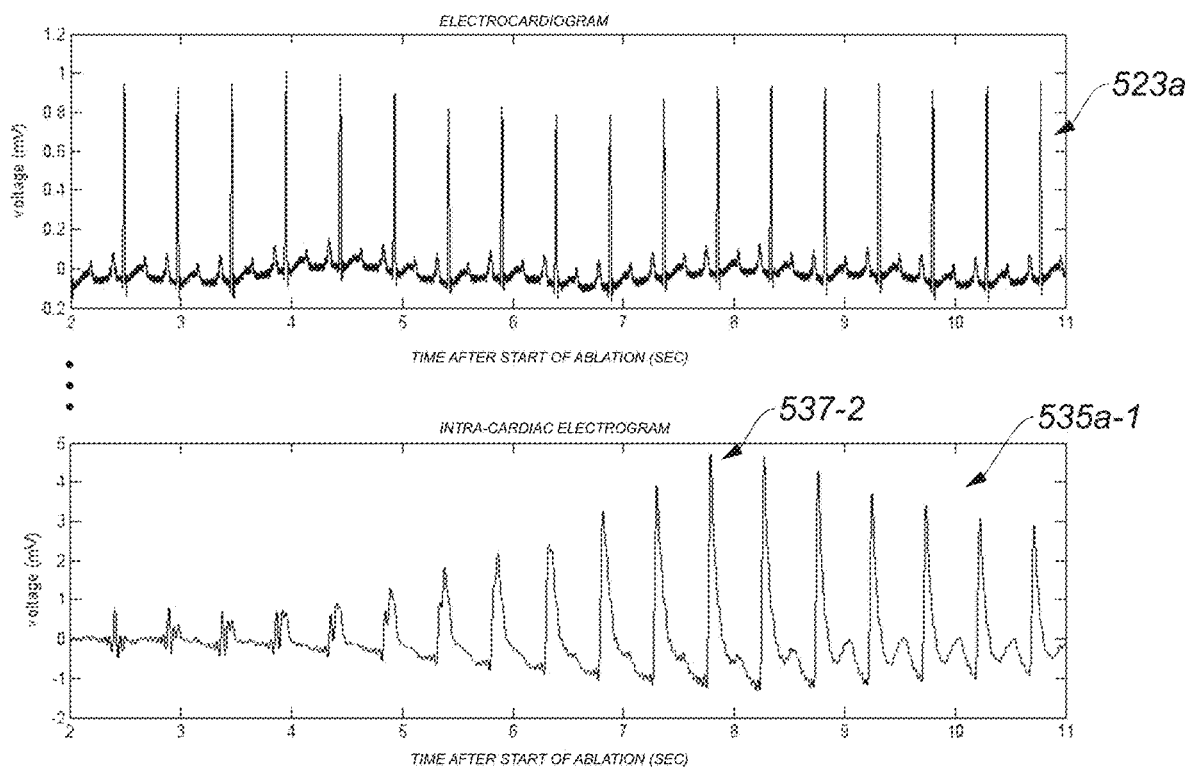
FIG. 7E includes a low pass filtered version of the intra-cardiac electrogram of FIG. 7A displayed according to some embodiments.

It is noted that, in some embodiments, the sampled intra-cardiac information from which the intra-cardiac electrogram 535*a* is derived may be filtered (e.g., by way of low pass filtering) to change the displayed appearance of the intra-cardiac electrogram 535*a*. For example, FIG. 7E shows a filtered electrogram 535*a*-1, which is a frequency-weighted version of the intra-cardiac electrogram 535*a* shown in FIG. 7A. In this particular case, a low pass filter was employed to reduce various biphasic components in the biphasic portion 536*a* of intra-cardiac electrogram 535*a*. A maximum peak 537-2 (corresponding to maximum peak 537-1) having an amplitude of approximately 5 millivolts and occurring approximately 7.8 seconds after the start of the tissue ablation is also shown, although, as discussed above, the invention is not limited to such amplitude and peak timing.

Figure 7F:
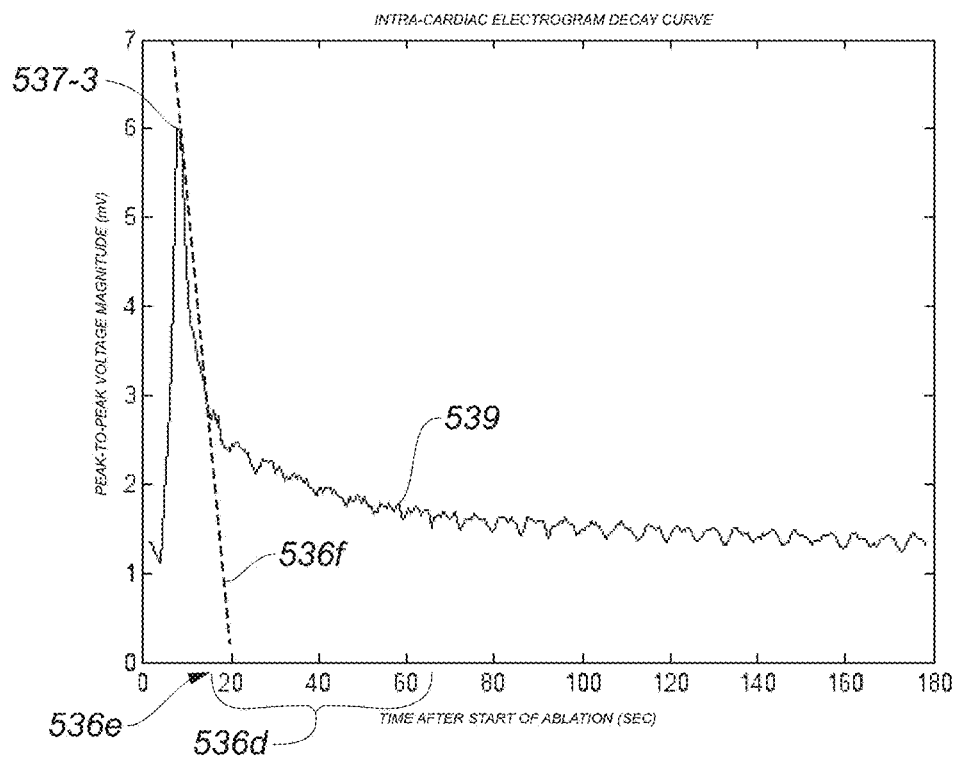
FIG. 7F includes a graph of a distribution of a plurality of data sets, each of the data sets derived from intra-cardiac voltage data sampled during a respective one of a plurality of cardiac cycles, the intra-cardiac voltage data employed to derive the intra-cardiac electrogram of FIG. 7E according to some embodiments.

FIG. 7F includes a graph of a distribution 539 of a plurality of data sets derived from intra-cardiac voltage data sampled by an electrode (e.g., 315, 415) over a period of time that includes a plurality of cardiac cycles, according to some embodiments. In some embodiments, each of the data sets is derived from the intra-cardiac voltage data (e.g., intra-cardiac electrogram data, in some embodiments) sampled by the electrode during a respective one of the plurality of cardiac cycles. In some embodiments, each of the data sets provides a respective point or group of points in the plotted distribution 539. For example, each of the data sets may be generated from the electrogram 535*a*-1 of FIG. 7E. In this regard, each of the data sets (e.g., data points in FIG. 7F, in some embodiments) may represent a maximum peak-to-peak voltage value magnitude (or a maximum minus minimum voltage value) of the electrogram (e.g., 535*a*-1) during a respective one of the cardiac cycles (e.g., a cardiac cycle defined by one of the groups of P, Q, R, S, and T waves in the electrocardiogram 523*a*). In some embodiments, if negative voltage values are present, a minimum value is considered to be the largest negative value that gives the greatest voltage range when compared with a maximum positive value. It is noted that other embodiments may alternately employ data sets representative of absolute maximum values (an absolute value of a peak positive or negative value), positive peak values, or negative peak values. Each respective one of the data sets may be plotted as a function of the particular sampling time, during the ablation, of the particular data (e.g., sampled during the respective cardiac cycle) from which the respective one of the data sets was derived. For example, if a data point in the distribution 539 is derived from a cardiac cycle represented in an intra-cardiac electrogram spanning a particular time period from 10 seconds after ablation to 10.5 seconds after ablation, the respective data point in the distribution could be plotted on the distribution 539 at time 10.25 seconds (or any other time) within the particular time period, with the same defined time-plotting convention consistently used for each other data point with respect to its own cardiac cycle.

The present inventors have noted that the respective values of the data sets (e.g., as shown in FIG. 7F) increase relatively quickly after the start of the ablation and reach a maximum peak typically at the point in time at least proximate to the occurrence of maximum peak 537-2 in intra cardiac electrogram 535a-1 in FIG. 7E. As the ablation continues, the present inventors have noted that the values of the data sets (e.g., data points in distribution 539, in some embodiments) fall and then generally plateau with relatively little change (e.g., +/−15% or +/−0.3 millivolts in some embodiments). During ablation, the peak of a portion of the monophasic intra-cardiac electrogram derived from data sampled during a particular cardiac cycle, typically corresponds to a point where a propagation of the local atrial depolarization front passes the sampling electrode. This typically occurs within the P wave portion of the electrocardiogram or between the P wave and Q wave portions of the electrocardiogram, which in various embodiments is a consequence of the propagation of the depolarization front over the whole of the atria of the heart. As the ablation continues during successive cardiac cycles, the peak of the respective portion of the monophasic intra-cardiac electrogram derived from data sampled during each of the successive cardiac cycles decays as a consequence of the continued expansion or growth of the ablated area including a growth of the depth of the ablated region (e.g., into the tissue wall). In some embodiments, the amplitude of the monophasic waveform contribution is proportional to the range (e.g., maximum minus minimum voltage) of the monophasic waveform.

The inventors have noted that (a) the time from the start of ablation to the time of the maximum voltage peak (e.g., a maximum peak of a respective decay distribution like maximum peak 537-3 of distribution 539 in FIG. 7F or a maximum peak of a respective electrogram like maximum peak 537-1 of electrogram 535a or maximum peak 537-2 of electrogram 535a-1, according to some embodiments), and (b) the curve-slope (e.g., curve-slope 536f in FIG. 7F, which may be different in different embodiments) from the time of occurrence of the maximum voltage peak to a time (e.g., time 536e in FIG. 7F, which may be different in different embodiments) indicating a beginning of a pre-plateau transitional region (e.g., transitional region 536d in FIG. 7F, which may be different in different embodiments, and which may correspond to the corresponding times in the electrograms of FIGS. 7A-7E, although such times are not shown in those figures) provide indications of the thickness of the tissue being ablated. For example, a relatively short time from the start of ablation to the maximum voltage peak (e.g., less than 9 seconds), when electrode size and tissue-ablative-energy-transmitted are held constant, will indicate thinner tissue (e.g., less than 2.5 mm) than a relatively longer time (e.g., greater than 9 seconds) from the start of ablation to the maximum voltage peak which indicates relatively thicker tissue (e.g., greater than 2.5 mm). In addition, when electrode size and tissue-ablative-energy-transmitted are held constant, a steeper curve-slope from the maximum voltage peak to the beginning of the pre-plateau transitional region will indicate thinner tissue than a relatively flatter curve-slope from the maximum voltage peak to the beginning of the pre-plateau transitional region.

Figure 10A:
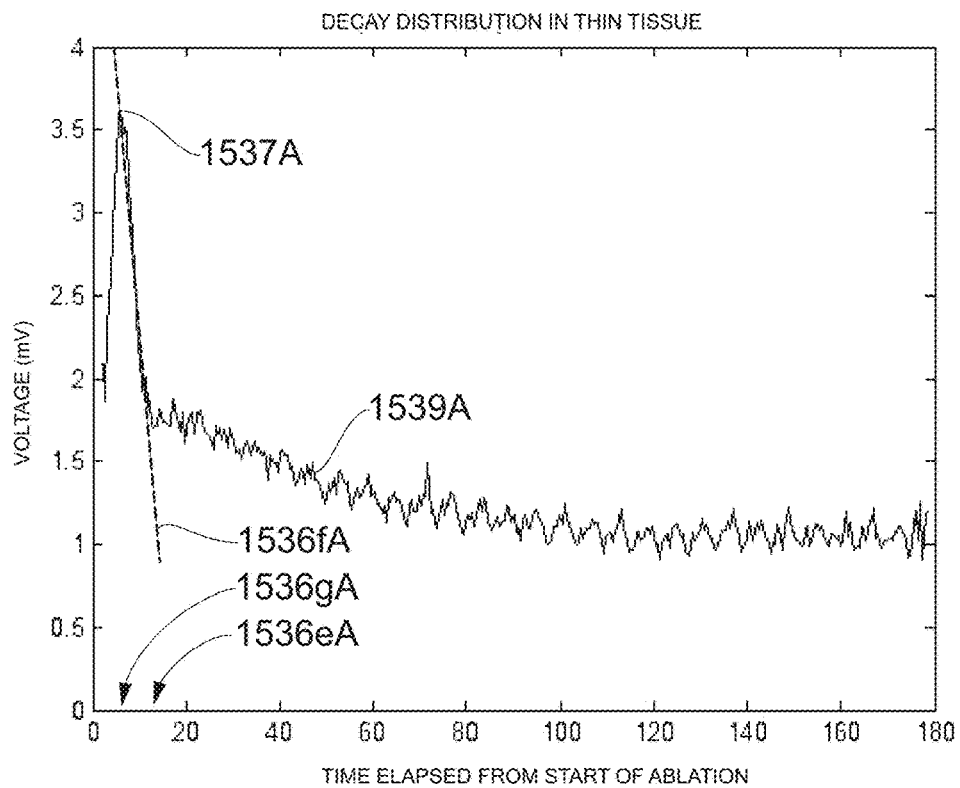
FIGS. 10A and 10B provide in-vivo data, according to some embodiments.
Figure 10B:
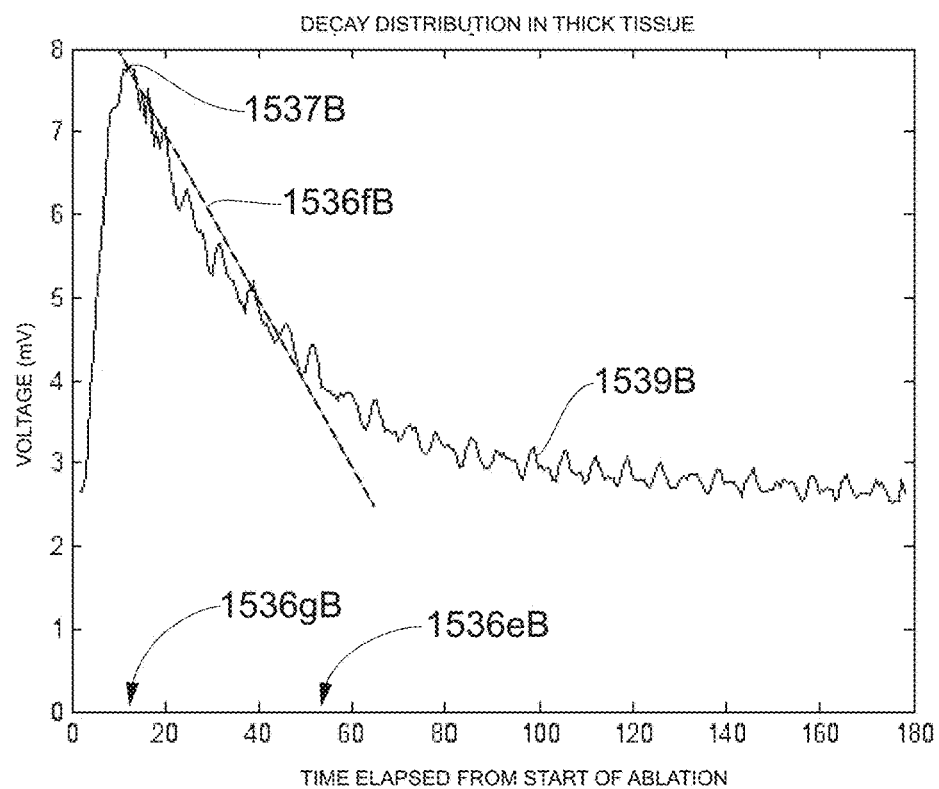

For example, FIGS. 10A and 10B provide in-vivo data illustrating these features. The procedures which generated the data represented in FIGS. 10A and 10B employed relatively equal electrode size and relatively equal tissue-ablative-energy-transmission levels. FIG. 10A represents a decay distribution 1539A like distribution 539 for thin cardiac tissue (e.g., less than 2.5 mm), whereas FIG. 10B represents a decay distribution 1539B like distribution 539 for thick cardiac tissue (e.g., greater than 2.5 mm). In this regard, it can be seen in FIG. 10A that the time from the start of ablation to the time 1536gA of the maximum voltage peak 1537A is approximately 7-8 seconds for the thin tissue, whereas the time from the start of ablation to the time 1536gB of the maximum voltage peak 1537B in FIG. 10B is approximately 14-15 seconds for the thick tissue. Further, it can be seen in FIG. 10A that the curve-slope 1536fA from a time proximate the time 1536gA of the maximum voltage peak 1537A to a time 1536eA indicating a beginning of a pre-plateau transitional region in the distribution 1539A is steeper for the thin tissue than it is for the thick tissue, as shown in FIG. 10B. In particular, the curve-slope 1536fB from a time proximate the time 1536gB of the maximum voltage peak 1537B to a time 1536eB indicating a beginning of a pre-plateau transitional region in the distribution 1539B is less steep than the curve-slope 1536fA for the thin tissue.

Accordingly, in some embodiments, the data processing device system (e.g., 110, 310) is configured to identify a time of the maximum voltage peak from the start of ablation, the above-discussed curve-slope, or both, and based at least on known electrode size, shape, and ablation-energy-delivery characteristics, as well as a comparison with previously stored or predetermined time-to-peak/curve-slope information (e.g., thresholds) that relate(s) time-to-peak, respective curve-slope, or both to tissue thickness, the data processing device system (e.g., 110, 310) is configured to output an indication via the input-output device system 120 (e.g., via a display device user interface like any of those shown in FIG. 5) of tissue thickness proximate the electrode (e.g., 315, 415) that provided the data that resulted in the distribution curve 539. In addition or in the alternative, the data processing device system (e.g., 110, 310) may be configured to output an indication via the input-output device system 120 (e.g., via a display device user interface like any of those shown in FIG. 5) of an estimate of projected ablation time required for transmurality, as ablation time is a function of tissue thickness. Such indications may be especially helpful when multiple electrodes are simultaneously performing tissue ablation.

In some embodiments, the data processing device system (e.g., 110, 310) is configured, e.g., by data reception instructions to cause reception of intra-cardiac voltage data via an input-output device system 120, the intra-cardiac voltage data sampled by a sensing electrode (e.g., 315, 415) over a period of time that includes a plurality of cardiac cycles. Activation instructions may configure the data processing device system (e.g., 110, 310) to cause an ablation electrode (e.g., 315, 415, same or different than the sensing electrode) to transmit energy sufficient for tissue ablation at least during the sampling of the intra-cardiac voltage data by the sensing electrode. Data derivation instructions may configure the data processing device system (e.g., 110, 310) to derive at least a plurality of voltage values (e.g., data points in an electrogram or decay curve), each of the plurality of voltage values derived at least in part from a respective portion of the received intra-cardiac voltage data (e.g., some or all of the intra-cardiac voltage data associated with a particular cardiac cycle). Each of the plurality of voltage values may be correlated, according to the derivation instructions, with a respective time within a time range during which that the respective portion of the of the received intra-cardiac voltage data was sampled by the sensing electrode. For example, if the voltage values are data points in a decay curve like distribution 539, each data point is correlated with a time on the X-axis in FIG. 7F, which is a time within a respective cardiac cycle in an electrogram, e.g., 535*a*-1, from which such data point was derived. Identification instructions may configure the data processing device system (e.g., 110, 310) to identify a duration from a time from a start of the tissue ablation to the respective time (e.g., time 1536*g*A in FIG. 10A) correlated with a particular one of the respective voltage values, the particular one of the respective voltage values being a maximum value (e.g., peak 1537A in FIG. 10A) as compared with others of the plurality of voltage values. Tissue thickness determination instructions may be configured to determine a thickness of tissue subject to the tissue ablation based at least upon a comparison of the identified duration with a predetermined threshold. Thickness indication instructions may be configured to output a tissue-thickness indication via the input-output device system indicating a result of the determination of the thickness of the tissue. In some embodiments, the activation instructions may be configured to cause the ablation to cease within a particular predetermined time after the tissue thickness determination has been made, the particular predetermined time varying in accordance with the particular thickness of the tissue that is determined. In some embodiments, the particular predetermined time is predetermined to cause the ablation to continue for an additional time sufficient to cause a transmural lesion in tissue having a thickness corresponding to the thickness indicated by the tissue thickness determination instructions.

Figure 9A:
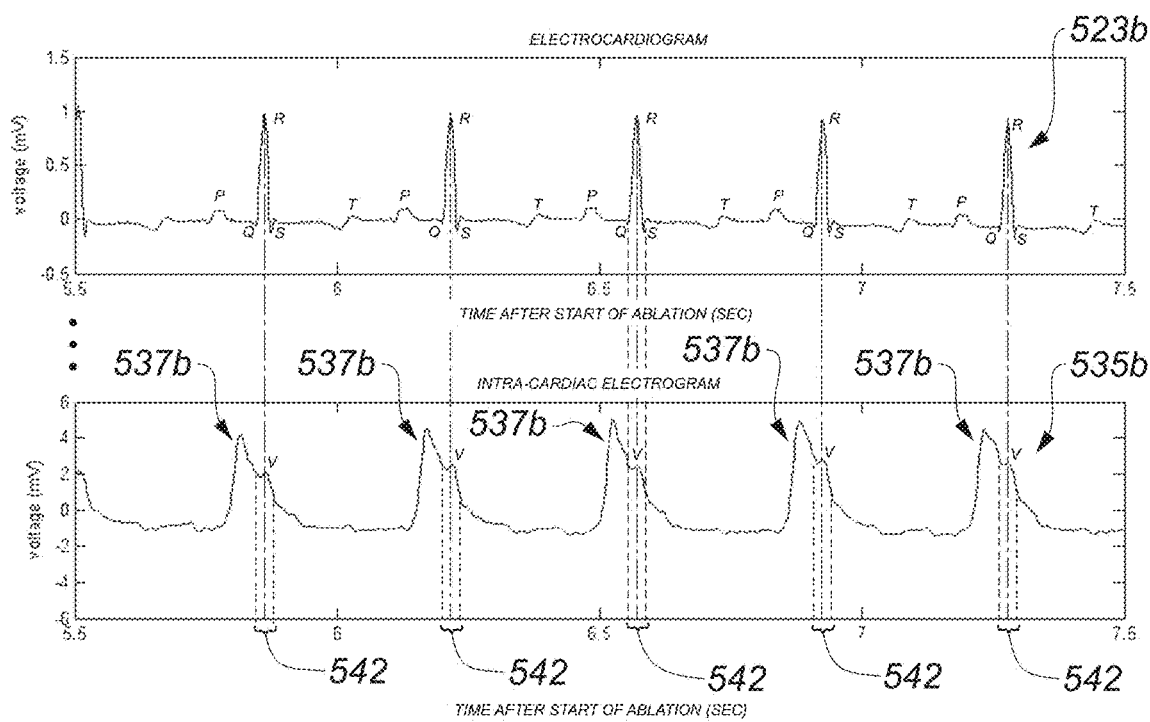
FIGS. 9A, 9B, and 9C include portions of an intra-cardiac electrogram at three successive times during the period of time displayed respectively in FIGS. 8A-8C according to some embodiments.
Figure 9B:
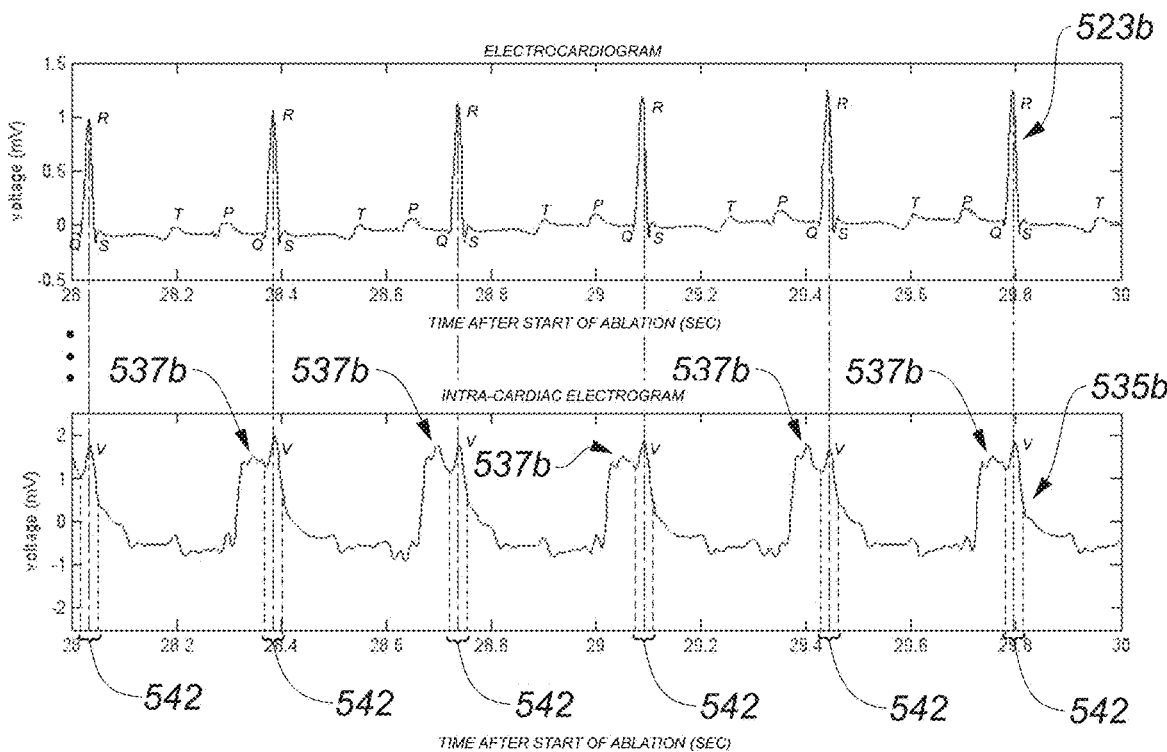
Figure 9C:
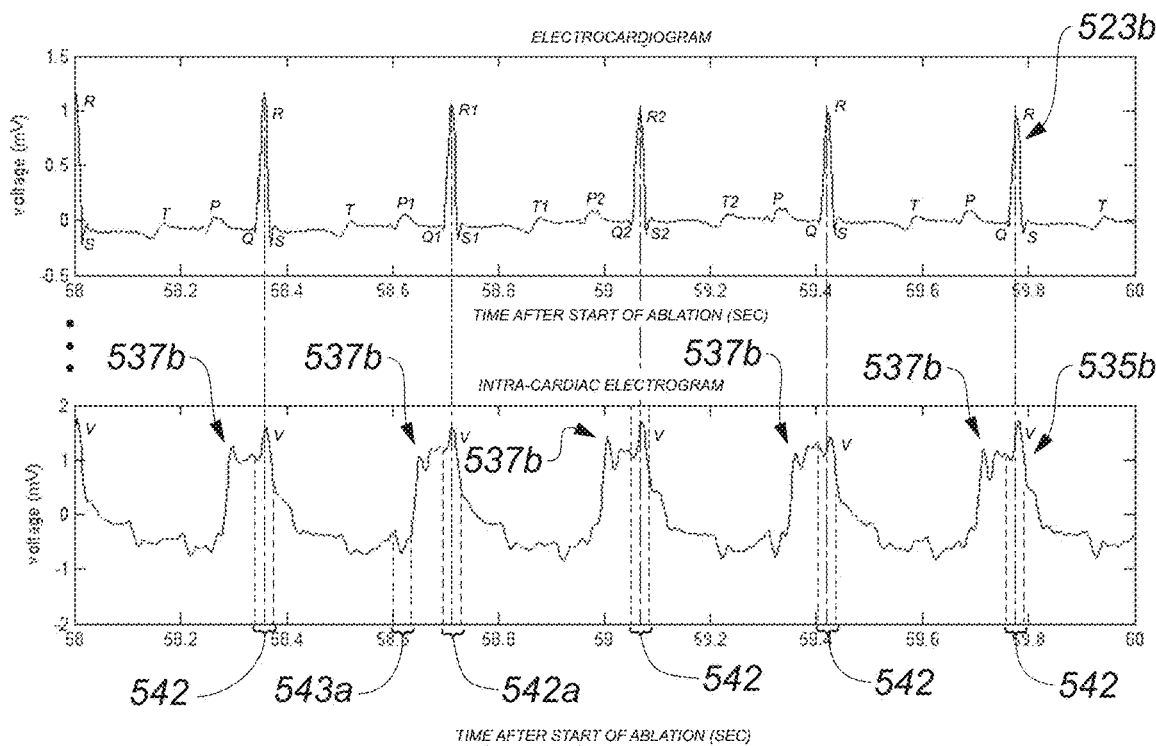

The data derivation instructions may be configured to derive each of at least three of the plurality of voltage values only from the respective portion of the received intra-cardiac voltage data, each respective portion from which a respective one of the at least three of the plurality of voltage values is derived representing some, but not all, of the intra-cardiac voltage data sampled by the sensing electrode during a respective cardiac cycle (e.g., excluding a respective portion 542 in FIG. 9C as described below). Display instructions may configure the data processing device system (e.g., 110, 310) to display, via the input-output device system, the plurality of voltage values, which may be displayed as a distribution (e.g., 539) or an intra-cardiac electrogram (e.g., 535*a*-1 or 535*a*). As discussed above, an electrogram (e.g., 535*a*-1 or 535*a*) may be concurrently displayed with a decay distribution (e.g., 539), according to the display instructions. In some embodiments, the electrogram has a visual characteristic set that is distinct from a visual characteristic set of the decay distribution, such as different colors or different locations on the display. In some embodiments, the voltage values are data points in an intra-cardiac electrogram (e.g., 537) and the identification instructions may configure the data processing device system (e.g., 110, 310) to identify a duration from a time from a start of the tissue ablation to the respective time of a peak voltage value in the electrogram (e.g., 537-1, 537-2). Like various embodiments described above, tissue thickness determination instructions may be configured to determine a thickness of tissue subject to the tissue ablation based at least upon a comparison of the identified duration with a predetermined threshold. Thickness indication instructions may be configured to output a tissue-thickness indication via the input-output device system indicating a result of the determination of the thickness of the tissue.

The present inventors have also determined that a lesion formed by the ablation in the tissue wall will become transmural in some embodiments when the data sets (e.g., data points in distribution 539) have values that remain relatively constant (e.g., in the plateau region of the graph) or the slope of the plateau region remains fairly constant. The present inventors have determined that a lesion formed by the ablation of the tissue wall will become transmural in some embodiments when the data sets (e.g., which may be data points in distribution 539 in some embodiments) have values that have fallen by a predetermined amount (e.g., 70%) from the peak value indicated in the graph. The present inventors have determined that a lesion formed by the ablation in the tissue wall may become transmural when an indication of a rate of change of a trend of the data set values over the ablation period becomes less than a particular rate (e.g., 0.025 millivolts/sec in some embodiments, 0.010 millivolts/sec in other embodiments, or 0.002 millivolts/sec in yet other embodiments) at a time at least proximate the plateau region. Such a rate of change analysis may be obtained by determining when the second derivative of the plotted data sets becomes zero or within a predetermined range of zero (e.g., absolute value less than 0.1, 0.05, 0.02, or 0.01).

Accordingly, in some embodiments, ablation termination instructions may cease the tissue ablation in response to an indication of one or more transmurality determinations made above by the present inventors. In some embodiments, the data sets are displayed and a user may make a transmurality determination based on the displayed data sets. For example, FIG. 6D includes an exploded view of block 602 employed according to some embodiments in which at least the derived data sets are displayable (e.g., via a respective electrogram 535 subpanel in one or more of FIG. 5 via the display instructions associated with block 604, according to some embodiments) to a user such as a health care provider. Block 602 may include reception instructions associated with block 602-*e* that cause a reception of intra-cardiac voltage data via an input-output device system (e.g., 120, 320), the intra-cardiac voltage data sampled by an electrode (e.g., an electrode 315, 415) over a period of time that includes a plurality of cardiac cycles, including a first cardiac cycle and a second cardiac cycle. The instructions associated with block 602-*e* may be configured to cause a data processing device system (e.g., 110, 310) to receive the voltage data as discussed above with respect to block 602 in FIG. 6A, but, in some embodiments associated with block 602-*e*, the intra-cardiac information may include voltage data sampled by an electrode (e.g., an electrode 315, 415) over a period of time that includes a plurality of cardiac cycles, including a first cardiac cycle and a second cardiac cycle. In some embodiments, block 602 includes data derivation instructions associated with block 602-*f* that cause a derivation, for each respective one of the plurality of cardiac cycles, a respective one of plurality of data sets, at least in part from a respective portion of the intra-cardiac voltage data sampled by the electrode during the respective one of the plurality of cardiac cycles (e.g., generating the distribution 539 from an intra-cardiac electrogram 535*a*, according to some embodiments).

Figure 8A:
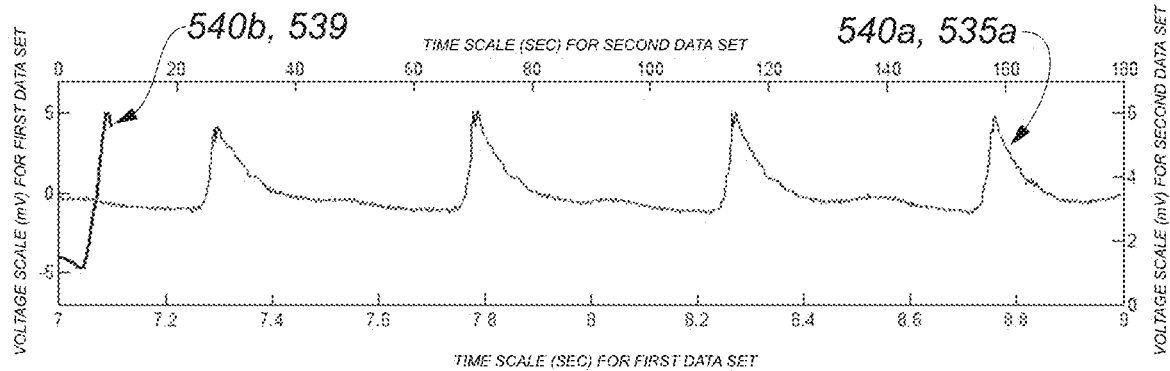
FIGS. 8A, 8B, and 8C show changes in a displayed graphical representation at three successive times, the graphical representation including a concurrently displayed first data set and a concurrently displayed second data set according to some embodiments.
Figure 8B:
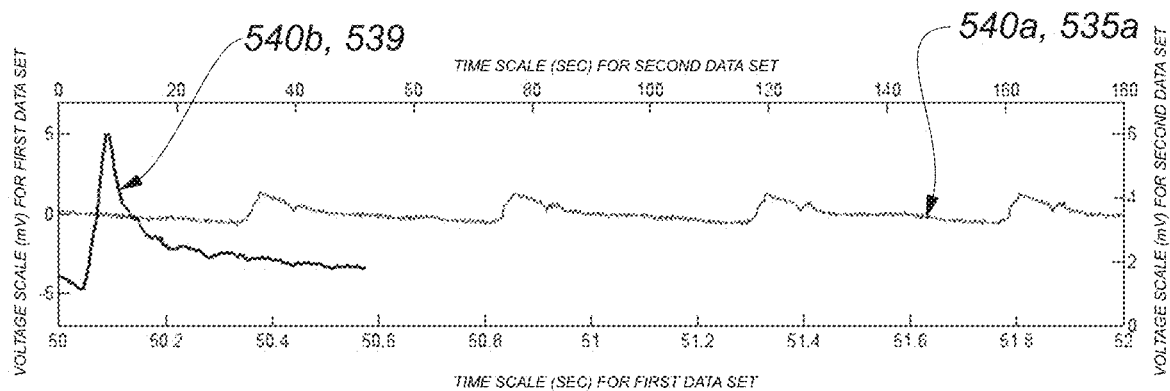
Figure 8C:
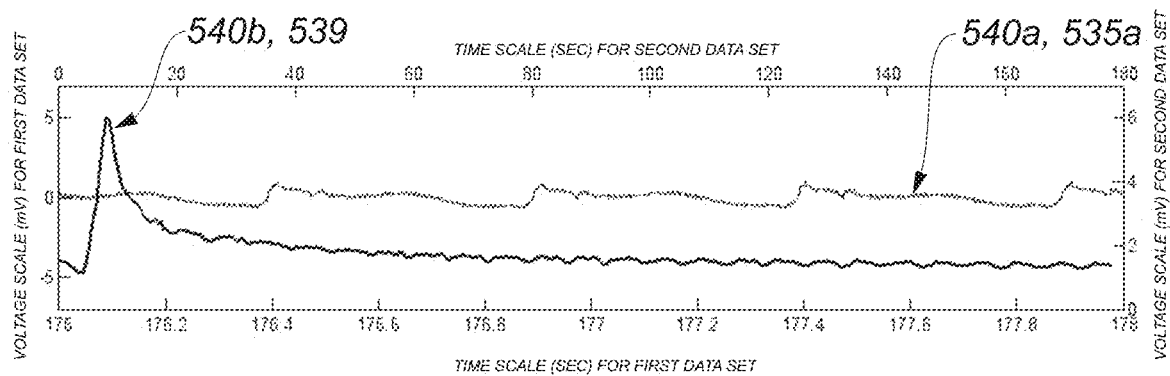

In some embodiments, the derived data sets are caused to be concurrently displayed via the input-output device system (e.g., via a respective electrogram 535 subpanel in one or more of FIG. 5 according to display instructions associated with block 604). For example, FIGS. 8A, 8B, and 8C show changes in a displayed graphical representation (which may be displayed in a electrogram 535 subpanel in one or more of FIG. 5) at three successive times, the graphical representation including a concurrently displayed first data superset 540a (which may represent an electrogram, such as all or a portion of electrogram 535a in FIG. 7A) and a concurrently displayed second data superset 540b (which may represent an electrogram decay distribution, such as all or a portion of distribution 539). (Note that first data superset 540a is equivalently referred to as "first data set" 540a herein, and second data superset 540b is equivalently referred to as "second data set" 540b herein.) In various embodiments, the graphical representation is displayed via an input-output device system (e.g., 120, 320). In some embodiments, the graphical representation is displayed via a graphical interface, for example, the graphical interface shown in various ones of FIG. 5. In some embodiments, the concurrently displayed first data set 540a includes and represents a first graphical distribution of data that includes first data (e.g., at least a portion of the data (e.g., a first group of voltage magnitudes) plotted for first data set 540a) displayed across a first time scale (represented, e.g., by the lower horizontal x-axis in each of FIG. 8), and the concurrently displayed second data set 540b includes and represents a second graphical distribution of data that includes second data (e.g., at least a portion of the data (e.g., a second group of voltage magnitudes) plotted for second data set 540b) displayed across a second time scale (represented, e.g., by the upper horizontal x-axis in each of FIG. 8) that is different than the first time scale. In some embodiments, the concurrently displayed first data set 540a and the concurrently displayed second data set 540b are displayed concurrently with each other for at least a period of time, such as in a superimposed or overlapping configuration, such as that illustrated in each of FIGS. 8A-8C. However, the first data set 540a and second data set 540b may be concurrently displayed in a separate manner, e.g., one-above-another in a same graph as shown, e.g., in FIGS. 8D-8F, or, e.g., entirely separately on their own respective graphs.

In some embodiments, the concurrently displayed first data set 540a is represented as an electrogram (e.g., intra-cardiac electrogram 535a). Accordingly, in some embodiments, the concurrently displayed first data set 540a and the concurrently displayed second data set 540b may be displayed as a portion of an intra-cardiac electrogram panel displayed as part of a graphical interface (e.g., a subpanel displaying at least one of the intra-cardiac electrograms 535 shown in the panel of intra-cardiac electrograms displayed by the graphical representation in FIGS. 5L and 5M). The number of intra-cardiac electrogram pulses or cycles displayed in each of FIGS. 8A, 8B, and 8C (and FIGS. 8D, 8E, and 8F described below) corresponds to an electrogram sweep speed of approximately 50 millimeters per second and may be changed to different values by user manipulation of various ones of the electrogram sweep speed buttons 528 shown in FIGS. 5L and 5M by way of non-limiting example.

In some embodiments, the concurrently displayed second data set 540b ultimately is provided by distribution 539. As described above, distribution 539 includes a plurality of data sets (e.g., data points, as contrasted with first data superset 540a and second data superset 540b which represent segments or entireties of graphs, according to some embodiments). Each of the data sets in the distribution 539, as discussed above, may be derived from intra-cardiac voltage data sampled by an electrode (e.g., 315, 415) during a respective one of a plurality of cardiac cycles. In some embodiments, each of the data sets in distribution 539 may be generated from the electrogram 535a of FIG. 7A. Specifically, in some embodiments, each of the data sets in distribution 539 is derived from at least two values in the respective portion of the intra-cardiac voltage data sampled by an electrode (e.g., in accordance with the computer-executable instructions associated with block 602-e) during a respective one of the plurality of the cardiac cycles. In some embodiments, each of the data sets includes data representative of a difference between two values in the respective portion of the intra-cardiac voltage data sampled by an electrode (e.g., in accordance with the instructions associated with block 602-e) during a respective one of the plurality of the cardiac cycles. In some embodiments, each of the data sets represents a maximum peak-to-peak voltage value magnitude (or a maximum minus minimum voltage value) of the electrogram during a respective one of the cardiac cycles, as, e.g., discussed above with respect to FIG. 7F. In some embodiments, each of the data sets (e.g., points in distribution 539) represents peak or maximum voltage value of the electrogram during a respective one of the cardiac cycles.

As indicated by the sequence of FIGS. 8A, 8B, and 8C in which the concurrently displayed second set 540b (distribution 539) grows as the sequence advances, each of the plurality of data sets in distribution 539 is sequentially displayed (e.g., as points along the distribution 539) by the input-output device system (e.g., in accordance with the instructions associated with block 604) until all of the plurality of data sets are concurrently displayed. In some embodiments, the plurality of data sets in distribution 539 are sequentially displayed (e.g., in accordance with the instructions associated with block 604) according to a first order that is consistent with an order of the plurality of the cardiac cycles associated with the plurality of data sets in distribution 539. In some embodiments, the plurality of data sets in distribution 539 are displayed (e.g., in accordance with the instructions associated with block 604) according to a first spatial order representative of an order of the plurality of the cardiac cycles associated with the plurality of data sets in distribution 539. Specifically, in FIG. 8A, a group of data sets making up a displayed portion of the concurrently displayed second data set 540b are shown and are derived from data sampled from the particular cardiac cycles occurring within the first 9 seconds from the start of the ablation. In some embodiments, a maximum value of the peak-to-peak values represented by the data set associated with a particular one of the cardiac cycles is displayed for each of the particular cardiac cycles occurring within the first 9 seconds from the start of ablation. For example, in FIG. 8A, the maximum value of the peak-to-peak value for the cardiac cycle occurring approximately 8 seconds from the start of ablation is approximately 6 millivolts and is represented as the first data point on the right-Y-axis in the distribution 539. FIG. 8A also shows the intra-cardiac electrogram 535a (e.g., an example of concurrently displayed first data set 540a) as it appears 7 to 9 seconds after the start of the tissue ablation (e.g., a series of monophasic pulses having amplitudes of approximately 5 millivolts as represented by the left-Y-axis). In this regard, FIG. 8A (as well as each of the others of FIG. 8) shows the intra-cardiac electrogram 535a (e.g., an example of concurrently displayed first data superset 540a) concurrently displayed with a plurality of data sets (e.g., data points) of the second data superset 540b (e.g., at least part of the distribution 539), the intra-cardiac electrogram 535a derived from at least a portion of the respective intra-cardiac voltage data sampled by the respective electrode.

In FIG. 8B, a group of data sets (e.g., data points including the data points shown in FIG. 8A, according to some embodiments) making up a displayed portion of the concurrently displayed second data superset 540b are shown and are derived from data sampled from the particular cardiac cycles occurring within the first 52 seconds from the start of the ablation. In particular, values of the data sets (e.g., data points, in some embodiments) making up the concurrently displayed second data set 540b have decayed from the maximum value shown in FIG. 8A and have approached or are about to approach a plateau region of the distribution 539, which in some embodiments may provide a visible indication that a transmural lesion has been achieved by the tissue ablation process, and thereby allow determination of whether the ablation process should stop. In some embodiments, values of the data sets (e.g., data points, in some embodiments) making up the concurrently displayed second data set 540b in FIG. 8B have decayed from the maximum value shown in FIG. 8A, e.g., a peak where the second derivative is zero, and have approached or are about to approach a subsequent region of the distribution 539 in which a second derivative of the values with respect to time approaches zero, which in some embodiments may provide an indication that a transmural lesion has been achieved by the tissue ablation process, and thereby allow determination of whether the ablation process should stop.

FIG. 8B also shows the intra-cardiac electrogram 535a (e.g., an example of concurrently displayed first data set 540a) as it appears 50 to 52 seconds after the start of the tissue ablation (e.g., a series of monophasic pulses having amplitudes of approximately 2 millivolts). The amplitudes of the monophasic electrogram pulses in FIG. 8B reduce (e.g., as compared with FIG. 8A) with increased ablation time. In FIG. 8C, a group of data sets (e.g., data points including the data points shown in FIGS. 8A and 8B, according to some embodiments) making up a displayed portion of the concurrently displayed second data set 540b are shown and are derived from data sampled from the particular cardiac cycles occurring within approximately 180 seconds from the start of the ablation. The values of the data sets (e.g., data points, in some embodiments) making up the concurrently displayed second data set 540b have decayed into the plateau region which, in some embodiments provides an indication that a transmural lesion was achieved sometime before this time. FIG. 8C also shows the intra-cardiac electrogram 535a (e.g., an example of concurrently displayed first data set 540a) as it appears 176 to 178 seconds after the start of the tissue ablation (e.g., a series of monophasic pulses having amplitudes of approximately 1.5 millivolts). In this regard, FIGS. 8A-8C show concurrent display of intra-cardiac electrogram 535a (e.g., an example of concurrently displayed first data set 540a) and data sets (e.g., data points in some embodiments) of the second data superset 540b (e.g., at least part of the distribution 539). Also in this regard, FIGS. 8B-8C show monophasic intra-cardiac electrogram 535a reducing in amplitude with each sequential display of each of at least some of the plurality of the data sets (e.g., data points in some embodiments) of the second data superset 540b (e.g., at least part of the distribution 539).

Although FIGS. 8A-8C (as well as FIGS. 8D-8F, discussed further below) show an electrogram 535a, which has not been low-pass filtered, a low-pass filtered electrogram (e.g., like electrogram 535a-1 in FIG. 7E) may instead be displayed (e.g., as at least part of one of the subpanels displaying at least one of the intra-cardiac electrograms 535 shown in the panel of intra-cardiac electrograms displayed by the graphical representation in FIGS. 5L and 5M), even if a non-low-pass filtered version of the electrogram is used to generate the second data superset 540b. However, second data superset 540b may be derived from low-passed filtered intra-cardiac voltage data. In at least some embodiments, a displayed non-low-pass filtered electrogram (e.g., electrogram 535a in FIG. 7A) may undergo a biphasic (e.g., portion 536a in FIG. 7A) to monophasic (e.g., portion 536b in FIG. 7A) transformation during sequential display of the data sets (e.g., data points in some embodiments) of the second data superset 540b (e.g., at least part of the distribution 539) through the sequence of FIGS. 8A-8C.

In some embodiments, the data processing device system (e.g., 110, 310) may monitor the displayed progression in the generation of the currently displayed second data set 540b during the ablation process to identify when the plateau region in the second data set 540b occurs, and provide an indication or notification to a user that the transmural lesion has been achieved in response to the identification of the plateau region. A determination of transmurality may indicate that the ablation process may be stopped, and thereby reduce the procedure time or reduce patient exposure to further ablation. In some embodiments, the ablation termination instructions responsive to values of the data sets in the concurrently displayed second data set 540b may automatically cause termination of the application of ablative energy when certain conditions indicating possible transmurality in the ablated tissue (e.g., conditions described above) are indicated by the concurrently displayed second data 540a.

Figure 8D:
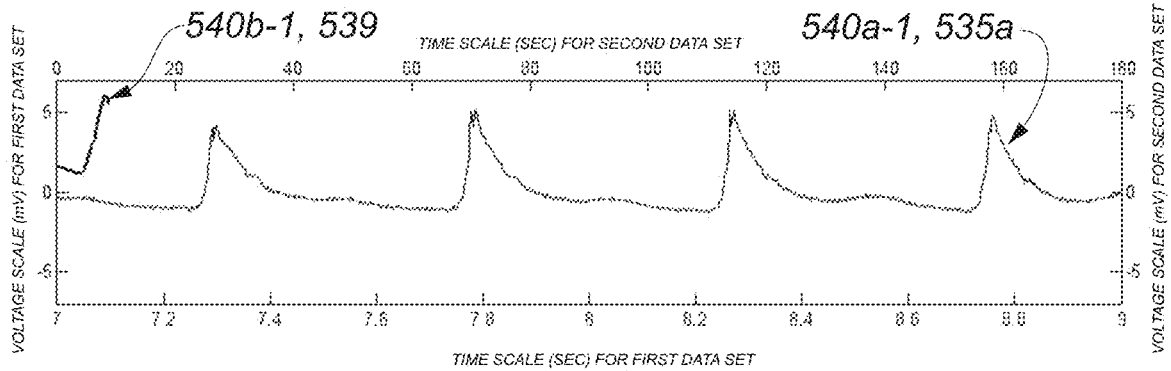
FIGS. 8D, 8E, and 8F show changes in a displayed graphical representation at three successive times, the graphical representation including a concurrently displayed first data set and a concurrently displayed second data set according to some embodiments.
Figure 8E:
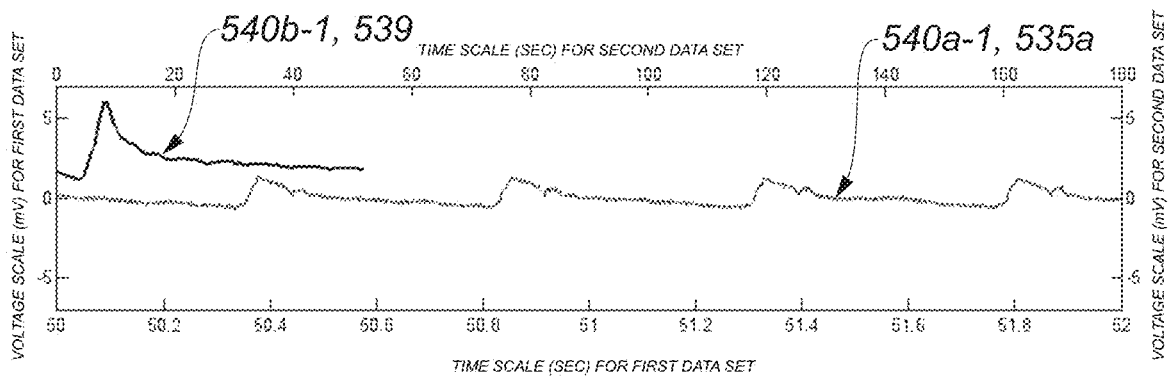
Figure 8F:
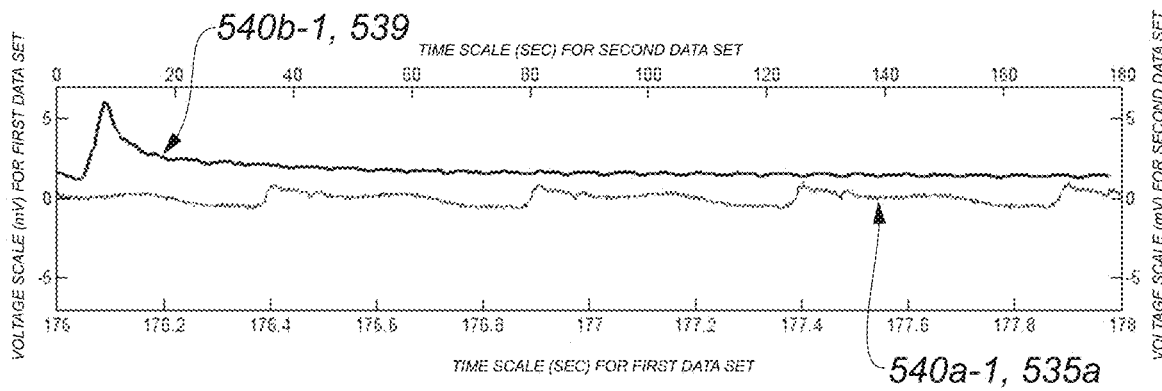

The displaying of the plurality of data sets (e.g., data points, in some embodiments) of the second data superset 540b (e.g., at least part of the distribution 539) among at least a portion of the intra-cardiac electrogram 535a in FIGS. 8A, 8B, and 8C allows a user to concurrently and easily assess both sets of information throughout the tissue ablation. In some embodiments, unlike FIGS. 8A, 8B, and 8C, the concurrently displayed first data set 540a and the concurrently displayed second data set 540b are not displayed in a superimposed configuration. In some embodiments, voltage scales for the concurrently displayed first data set 540a and the concurrently displayed second data set 540b that are different than those shown in FIGS. 8A, 8B, and 8C are employed. For example, FIGS. 8D, 8E, and 8F correspond to respective ones of the sequence of data changes in the concurrently displayed first data set 540a and the concurrently displayed second data set 540b shown in FIGS. 8A, 8B and 8C. In FIGS. 8D, 8E, and 8F, intra-cardiac electrogram 535-1 is representative of a concurrently displayed first data set 540a-1 and distribution 539 is representative of a concurrently displayed second data set 540b-1. A voltage scale for the concurrently displayed second data set 540b-1 of FIGS. 8D, 8E and 8F is different than a voltage scale for the concurrently displayed second data set 540b of FIGS. 8A, 8B and 8C. It is noted that various information such as X axis or Y axis information (e.g., title information, scale information) may not be displayed in various embodiments, but is included herein for the convenience of discussion.

As described above, in various embodiments, each of the data sets (e.g., data points in some embodiments) in the distribution 539 (e.g., an embodiment of a concurrently displayed second data superset 540b) are derived at least in part from a peak value or maximum value of a portion of the monophasic intra-cardiac electrogram derived from data sampled during respective one of plurality of the cardiac cycles. Ideally, this portion typically corresponds (e.g., temporally) to a portion of the intra-cardiac electrogram impacted by the ablation process (e.g., a particular portion of the intra-cardiac electrogram undergoing a reduction in amplitude with increased ablation time). In various embodiments, this decaying portion of the intra-cardiac electrogram typically corresponds to the P wave portion of the electrocardiogram or between the P wave and Q wave portions of the electrocardiogram. However, also contributing to the observed electrogram waveform is the far-field signal of the V wave (a consequence of ventricular depolarization). If the V wave contribution is sufficiently strong, the V wave may be larger in magnitude than the decaying monophasic waveform associated with an active ablation of the tissue. For example, intra-cardiac electrograms derived from data sampled relatively closer to the mitral valve will typically have relatively stronger V wave components than intra-cardiac electrograms derived from data sampled relatively farther from the mitral valve and thus typically comprise a dominant V wave component. In some embodiments, it may be preferable to configure the data processing device system (e.g., 110, 310) to identify the maximum or peak voltage values associated with the ablation induced decaying portions of the intra-cardiac electrogram. However, it may be relatively difficult to distinguish between the ablation-induced decaying portions of the intra-cardiac electrogram and the V wave contribution when the V wave is especially dominant or pronounced. This effect can be especially prominent when the ablation-induced decaying portion of the intra-cardiac electrogram has decayed to levels sufficient to make a determination that the ablated tissue region has become transmural, but transmurality cannot be identified because these levels are lower in magnitude than the V wave amplitude. In the extreme, an erroneous indication of transmurality may be arrived at (e.g., a false indication of transmurality) when V wave data is mistakenly employed.

For example, FIGS. 9A, 9B, and 9C show respective portions of a low-pass-filtered monophasic intra-cardiac electrogram 535*b* derived from intra-cardiac voltage data sampled by a particular electrode (e.g., an electrode 315, 415) over each of three different time periods after the start of ablation of cardiac tissue. In some embodiments, the sensing or sampling electrode also transmits the tissue ablative energy during each of at least the plurality of cardiac cycles represented in the respective FIGS. 9A-9C. In FIG. 9A, intra-cardiac voltage data is sampled during a time period of 5.5 seconds to 7.5 seconds after the start of ablation. In FIG. 9B, intra-cardiac voltage data is sampled during a time period of 28 seconds to 30 seconds after the start of ablation. In FIG. 9C, intra-cardiac voltage data is sampled during a time period of 58 seconds to 60 seconds after the start of ablation. A respective peak 537*b* marks a peak or maximum value of each respective cardiac cycle (e.g., a respective ablation-decay portion of the intra-cardiac electrogram 537*b*), a value of each successive peak 537*b* modulating (e.g., growing and decaying) as the ablation progresses in a manner the same as or similar to that described above. In some embodiments, each peak 537*b* corresponds to a region between the P wave and Q wave of the electrocardiogram 523*b*. It is noted that the V waves in FIGS. 9A, 9B, and 9C decay slowly throughout the ablation and remain at levels plateauing around 2 millivolts throughout the ablation. As will be apparent to those skilled in the art, the data processing device system (e.g., 110, 310) may be configured to identify a maximum or peak value associated with the ablation-decaying portion of each cardiac cycle in the intra-cardiac electrogram (e.g., portions comprising peak 537*b*). However, if precautions are not taken, such maximum or peak value may be incorrectly identified as a value associated with the V wave portion of the intra-cardiac electrogram, which typically decays at a much slower rate than the decaying portion of the intra-cardiac electrogram when the V wave portion is especially prominent or dominant (for example, as in the illustrated example embodiments). This situation can subsequently lead to an erroneous determination of ablated tissue transmurality. It is noted in FIG. 9C that various ones of the peaks 537*b* have reduced in amplitude during the ablation while corresponding respective ones of the V waves have greater amplitudes.

Figure 6E:
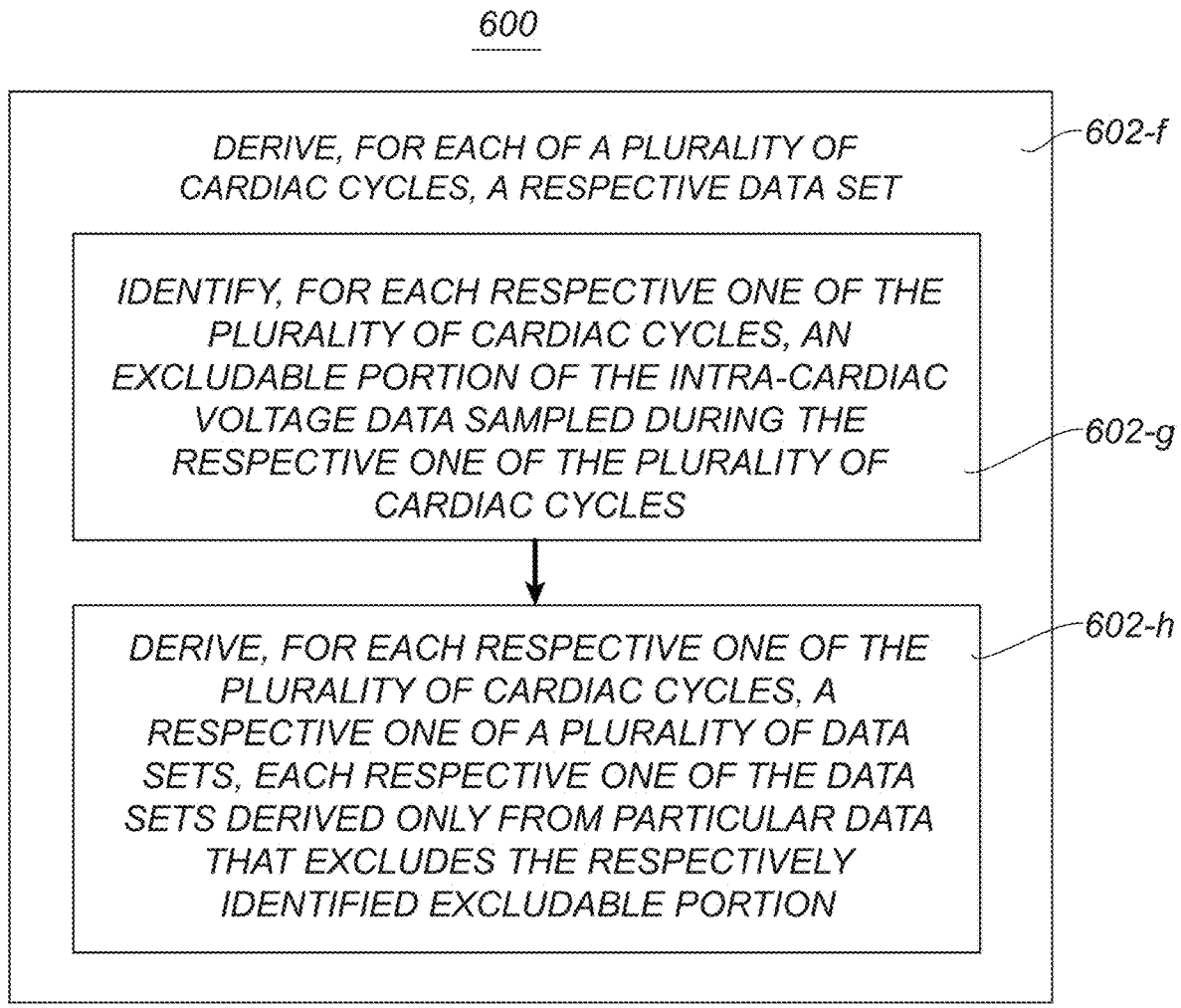

Precautions that avoid such erroneous identification of the maximum or peak value associated with the ablation-decaying portion of each cardiac cycle in the intra-cardiac electrogram (e.g., portions comprising peak 537*b*) may include excluding the V wave portion in each cardiac cycle of the electrogram in the determination of such maximum or peak value. For instance, FIG. 6E shows an exploded view of the computer-executable data derivation instructions associated with block 602-*f* (i.e., provided in FIG. 6D) employed according to some embodiments. The data derivation instructions associated with block 602-*f* may cause a derivation, for each respective one of the plurality of cardiac cycles, of a respective one of a plurality of data sets (e.g., data points in distribution 539 or 539*a*, according to some embodiments), at least in part from a respective portion of the intra-cardiac voltage data sampled by the electrode during the respective one of the plurality of cardiac cycles. In various embodiments, the derived data sets (e.g., forming at least part of the distribution 539 or 539*a*, according to some embodiments) are caused to be displayed via the input-output device system (e.g., by display instructions associated with block 604). Excludable data identification instructions may be associated with block 602-*g*, the excludable data identification instructions configured to cause identification, for each respective one the plurality of cardiac cycles, of a particular portion (e.g., a V wave portion, according to some embodiments) of the intra-cardiac voltage data sampled (e.g., by an electrode 315, 415) during the respective one of the cardiac cycles as an excludable portion of the intra-cardiac voltage data sampled during the respective one of the plurality of cardiac cycles. In various embodiments, each of identified excludable portions of the intra-cardiac voltage data includes some, but not all, of the intra-cardiac voltage data sampled during the respective one of the plurality of cardiac cycles. Instructions associated with block 602-*h* include data derivation instructions configured to derive, for each respective one of a plurality of cardiac cycles, a respective one of a plurality of data sets (e.g., data points in distribution 539 or 539*a*, according to some embodiments) at least in part from a portion of the intra-cardiac voltage data sampled during the respective one of the plurality of cardiac cycles, each respective one of the plurality of data sets derived only from particular data that excludes the identified (e.g., via the computer-executable instructions associated with block 602-*g*) excludable portion (e.g., the V wave portion, according to some embodiments) of the intra-cardiac voltage data during the respective one of the plurality of cardiac cycles.

For example, in each of FIGS. 9A, 9B, and 9C, particular portions of the sampled portions the intra-cardiac voltage data corresponding to a respective one of portions 542 of the intra-cardiac electrogram 535*b* may be identified via the instructions associated with block 602-*g* as corresponding to or be excludable portions of the sampled intra-cardiac voltage data. In some embodiments, each excludable portion includes some but not all of the intra-cardiac voltage data sampled during a respective one of the plurality of cardiac cycles. In some embodiments, each excludable portion excludes a portion of the intra-cardiac voltage data corresponding to the particular V wave of the intra-cardiac electrogram 535b portion corresponding to the respective cardiac cycle. Accordingly, in some of these particular embodiments, excluding the excludable portions of the sampled intra-cardiac voltage data allows for derivation of the each of the data sets based at least on a maximum or peak value of a relevant ablation-induced decaying portion (e.g., represented by an electrogram portion comprising a peak 537b) of the sampled intra-cardiac voltage data, while eliminating the risk that a maximum or peak value of a non-ablation-induced decaying portion (e.g., a V wave portion) is instead identified. In some embodiments, excluding intra-cardiac voltage data from when the V wave is present permits the ablation-driven decay of the monophasic amplitude to be accurately reflected and allows, in some embodiments, a more accurate transmurality determination.

Various excludable portions of the sampled intra-cardiac voltage data may be identified in different manners according to various embodiments. For example, FIG. 6F shows some implementation details of various embodiments of method 600 according to some embodiments. In this regard, blocks 616 and 618 may be located, in some embodiments, immediately before block 602-g in block 602-f in FIG. 6E. In particular, block 616 may be associated with cardiac event identification instructions configured to cause a data processing device system (e.g., 110, 310) to identify a respective occurrence of a particular cardiac event in each of the plurality of cardiac cycles, e.g., from the intra-cardiac voltage data sampled by the respective electrode. Block 618 is associated with data identification instructions configured to identify a respective excludable first portion of the intra-cardiac voltage data identified in accordance with a predetermined temporal relationship with the respective occurrence of the particular cardiac event identified in the respective one of the plurality of cardiac cycles. In some embodiments, the excludable data identification instructions associated with block 602-g (i.e., FIG. 6E) are configured to identify each excludable portion of the intra-cardiac voltage data sampled during the respective one of the plurality of cardiac cycles as being or at least including the identified respective excludable first portion (i.e., identified via the computer-executable instructions associated with block 618) occurring in the respective one of the plurality of cardiac cycles. For instance, an excludable portion (e.g., a V wave portion) within a cardiac cycle of an intra-cardiac electrogram may be identified according to the instructions associated with block 618 as being or at least including a first portion of the corresponding intra-cardiac voltage data sampled by the respective electrode, the first portion having a predetermined temporal relationship with a respective occurrence of a particular event within the cardiac cycle identified according to the instructions associated with block 618. An example of the cardiac event, as described in more detail below, may be an R wave in an electrocardiogram, or some other cardiac event, such that the V wave portion has a predetermined temporal relationship (e.g., occurs contemporaneously) with the R wave or other cardiac event, according to some embodiments. The data derivation instructions (i.e., associated with block 602-h) may be configured according to various embodiments to derive, for each respective one of the plurality of cardiac cycles, a respective one of the plurality of data sets at least in part from a respective second portion of the sampled intra-cardiac voltage data during the respective one of the plurality of cardiac cycles, each respective one of the plurality of data sets derived only from particular data (which may be or at least include the second portion of the sampled intra-cardiac voltage data, according to some embodiments) that excludes the excludable portion of the intra-cardiac voltage data identified in the respective one of the plurality of cardiac cycles, each excludable portion including the respective first portion (i.e., identified via the computer-executable instructions associated with block 618) identified in the respective one of the plurality of cardiac cycles.

In some embodiments, the cardiac event identification computer-executable instructions associated with block 616 are configured to identify the respective occurrence of the particular cardiac event in each respective one of the plurality of cardiac cycles from data other than the sampled intra-cardiac voltage data (e.g., data other than the sampled intra-cardiac voltage data employed to generate intra-cardiac electrogram 535b in FIGS. 9A, 9B, and 9C). For example, in some embodiments, the respective occurrence of the particular cardiac event in each of the respective one of the plurality of cardiac cycles is identified from electrocardiogram data. For example, the particular R wave in each particular cardiac cycle in electrocardiogram 523b in FIGS. 9A, 9B, and 9C may be identified as the particular cardiac event, because it is typically readily identifiable as it comprises a maximum magnitude or amplitude (e.g., a maximum absolute voltage value in the electrocardiogram data 523b) as compared to the respective peak values of the respective other waves associated with the particular cardiac cycle in the electrocardiogram 523b (i.e., each particular R wave has the greatest peak value as compared to the peak values of the other waves which combined with the particular R wave make up a respective one of the cardiac cycles). In some embodiments, the data processing device system (e.g., 110, 310) is configured to identify or locate each of the R waves. For example, a threshold sufficiently above typical P wave, Q wave, S wave, and T wave peak values may be set, and an average or median value of the corresponding times of the portions of the electrocardiogram data above the threshold may be employed to determine the location of each R wave in its respective cardiac cycle.

In various embodiments, a particular time associated with the occurrence of each of the R waves (e.g., a time corresponding to the peak of the identified R wave) is identified. In some embodiments, each excludable portion of the sampled intra-cardiac portion of the intra-cardiac data is determined in accordance with a predetermined temporal relationship with a respective identified times. For example, in FIGS. 9A, 9B, and 9C, each portion 542 of intra-cardiac electrogram 535b corresponds to the identified particular time of a respective one of the R waves. In these particular illustrated embodiments, a bilateral time interval is determined for each identified particular time of a respective one of the R waves, the bilateral time interval defining extents of each portion 542 of intra-cardiac electrogram 535b. In these particular illustrated embodiments, each time interval is a predetermined time interval that includes the identified particular time of a respective one of the R waves. In various embodiments, portions of the intra-cardiac voltage data sampled during each of the time intervals are identified as excludable portions and are excluded from the determination of the data sets.

In some embodiments, the bilateral time interval comprises an equal time interval on each side of the identified particular time associated with the occurrence of the R wave as the particular cardiac event, while in other embodiments the bilateral time interval comprises an unequal time interval on each side of the identified particular time. In some embodiments, a unilateral time interval is determined in which the identified particular time forms a beginning or end thereof. In some particular embodiments, each of the portions 542 has been selected sufficiently large to allow for the exclusion of intra-cardiac voltage data corresponding to a respective one of the V waves in the intra-cardiac electrogram data. In some embodiments, each of the portions 542 has been selected sufficiently large to allow for the exclusion of intra-cardiac voltage data corresponding to a respective one of the V waves in the intra-cardiac electrogram data without including portions of the intra-cardiac electrogram 535*b* that include a respective one of peaks 537*b*.

It is noted that various ones of the portions 542 may be defined from other forms of time intervals in other embodiments. For example, a group of time intervals, each spanning different amounts of time, may be employed in some embodiments. In some embodiments, a unilateral time interval is defined for each of at least some of the identified particular cardiac events. In various embodiments, the data identification instructions associated with block 618 are configured to identify each respective first portion (which may represent all or a portion of the excludable portion, e.g., 542) of the sampled intra-cardiac data as including a portion of the intra-cardiac voltage data sampled at least in part during the occurrence of the particular cardiac event identified in the respective one of the plurality of cardiac cycles (for example, as shown in FIGS. 9A, 9B, and 9C). In various embodiments, the data identification instructions associated with block 618 are configured to identify each respective first portion (which may represent all or a portion of the excludable portion, e.g., 542) of the sampled intra-cardiac data as including a portion of the intra-cardiac voltage data sampled at least in part after the occurrence of the particular cardiac event identified in the respective one of the plurality of cardiac cycles. In various embodiments, the data identification instructions associated with block 618 are configured to identify each respective first portion (which may represent all or a portion of the excludable portion, e.g., 542) of the sampled intra-cardiac data as including a portion of the intra-cardiac voltage data sampled at least in part before the occurrence of the particular cardiac event identified in the respective one of the plurality of cardiac cycles. In some embodiments, the data identification instructions associated with block 618 are configured to identify each respective first portion (which may represent all or a portion of the excludable portion, e.g., 542) of the sampled intra-cardiac data as not including any portion of the intra-cardiac voltage data sampled during a time of the occurrence of the particular cardiac event identified in the respective one of the plurality of cardiac cycles.

In some embodiments, the particular cardiac event may be identified from the particular intra-cardiac electrogram that corresponds to the sampled intra-cardiac voltage data or from another intra-cardiac electrogram (for example another intra-cardiac electrogram derived from intra-cardiac voltage data sampled by a second electrode). In various embodiments, multiple intra-cardiac electrograms are concurrently displayed (e.g., FIGS. 5L and 5M). In some of these various embodiments, each of the electrograms is derived from voltage data sampled by a respective one of a plurality of electrodes (e.g., electrodes 315, 415). The plurality of electrodes may sample the voltage data concurrently in some embodiments. In some embodiments, at least one particular one of the intra-cardiac electrograms may have a particular pronounced portion representative of a particular cardiac event that is present in each of the plurality of cardiac cycles (e.g., a pronounced V wave portion). The at least one particular one of the intra-cardiac electrograms may be used as a basis for the determination of the excludable portions in other ones of the intra-cardiac electrograms (for example, in a manner similar to the electrocardiogram methods described above).

The V wave in intra-cardiac electrograms or the R wave in electrocardiograms is typically associated with ventricular systole. In some embodiments, the particular cardiac event is not identified from electrocardiograms or electrograms, but rather from transducer data representative of blood pressure data. For example, in some embodiments, the cardiac event identification instructions associated with block 616 are configured to identify from blood pressure data the respective occurrence of the particular cardiac event in each respective one of the plurality of cardiac cycles as a respective occurrence of ventricular systole during the respective one of the plurality of cardiac cycles.

It is noted that in some embodiments, the particular cardiac event identified by the cardiac event instructions associated with block 616 is not limited to events associated with ventricular systole (e.g., an R wave or V wave). Without limitation, other particular cardiac events that may occur or repeat in each of the plurality of cardiac cycles and which are sufficiently detectable such that a first portion (which may represent all or a portion of the excludable portion, e.g., 542) of the sampled intra-cardiac voltage data sampled during a respective one of the cardiac cycles can be identified in accordance with a predetermined temporal relationship with the particular cardiac event identified in the respective one of the cardiac cycles may be employed by some embodiments. Without limitation, the cardiac event identification instructions associated with block 616 may be configured, in some embodiments, to identify the respective occurrence of the particular cardiac event in each respective one of a plurality of cardiac cycles as a respective occurrence of at least part of a QRS complex in electrocardiogram data during the respective one of the cardiac cycles, a respective occurrence of P wave in electrocardiogram data during the respective one of the cardiac cycles, or a respective occurrence of T wave in electrocardiogram data during the respective one of the cardiac cycles. Without limitation, the cardiac event identification instructions associated with block 616 may be configured, in some embodiments, to identify the respective occurrence of the particular cardiac event in each respective one of the plurality of cardiac cycles as a respective occurrence of ventricular systole during the respective one of the cardiac cycles, a respective occurrence of ventricular diastole during the respective one of the cardiac cycles, a respective occurrence of atrial systole during the respective one of the cardiac cycles or a respective occurrence of atrial diastole during the respective one of the cardiac cycles.

In some embodiments, the excludable data identification instructions associated with block 602-*g* are configured to identify the excludable portion of the intra-cardiac voltage data sampled during a respective one of the plurality of cardiac cycles as a first portion (which may represent all or a portion of the excludable portion, e.g., 542) of the intra-cardiac voltage data sampled during the respective one of the plurality of cardiac cycles, the first portion being identified as including a peak value, a maximum value or maximum absolute value of the intra-cardiac voltage data sampled during the respective one of the plurality of cardiac cycles. In some embodiments, each identified first portion (which may represent all or a portion of the excludable portion, e.g., 542) of the intra-cardiac voltage data includes some but not all of the intra-cardiac voltage data sampled during the respective one of the plurality of cardiac cycles. In some embodiments, each of these first portions is identified as part of, or in response to, the identification of a particular cardiac event (for example, as per the instructions associated with block 616 and 618) in a respective one of a plurality of cardiac cycles. In some embodiments, a particular cardiac event is not necessarily identified as a precursor to the identification of at least some of the first portion which may include a peak value, a maximum value, or maximum absolute value of the intra-cardiac voltage data sampled during the respective one of the plurality of cardiac cycles. For example, intra-cardiac voltage data sampled by an electrode (e.g., 315, 415) at a position proximal to a mitral valve typically will include a V wave portion that includes a peak or maximum value as compared with the rest of the intra-cardiac voltage data sampled by the electrode during a particular one of the cardiac cycles (for example, as shown in FIG. 9C). Accordingly in these particular embodiments, a portion of the intra-cardiac voltage value including a peak value, a maximum value, or maximum absolute value of the intra-cardiac voltage data sampled during a respective one of the plurality of cardiac cycles may be directly identified as an excludable portion of the intra-cardiac voltage data sampled during the respective one of the plurality of cardiac cycles.

Figure 9D:
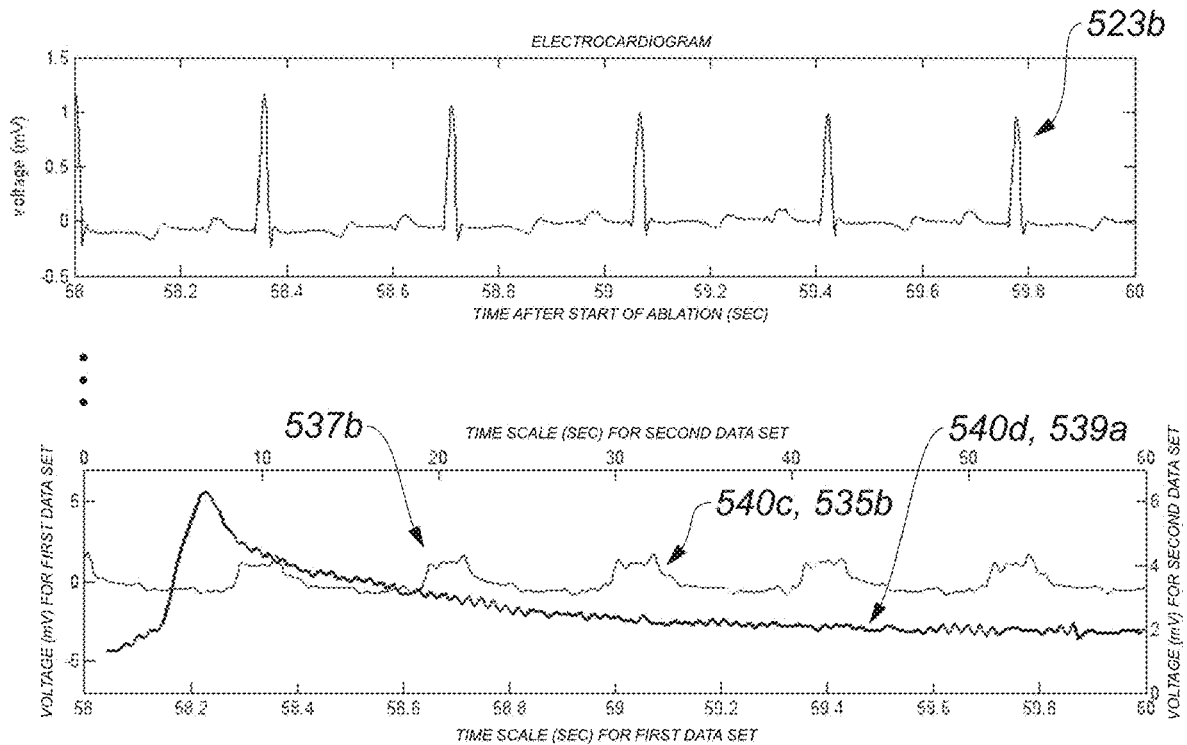
FIG. 9D includes a first concurrently displayed data set and a second concurrently displayed data set according to some embodiments.

FIG. 9D shows a group of concurrently displayed data sets similar to those shown in FIG. 8C, the concurrently displayed data sets displayed in accordance with various display instructions (e.g., the display instructions associated with block 604). In some embodiments, the concurrently displayed data sets are shown and are derived from data sampled from particular cardiac cycles occurring within approximately 60 seconds from the start of the ablation, and are derived in particular from the intra-cardiac voltage data associated with various ones of FIGS. 9A, 9B, and 9C. The concurrently displayed data sets (which may be voltage magnitude sets and may be frequency-weighted, as discussed above) include a concurrently displayed first data set (or superset) 540c and a concurrently displayed second data set (or superset) 540d. In some embodiments, both the concurrently displayed first data set 540c and the concurrently displayed second data set 540d are concurrently displayed. In some embodiments, the first data set 540c includes intra-cardiac electrogram 535b and, in particular, displays a representation of the sampled intra-cardiac voltage sampled across a plurality of cardiac cycles during a period of time between 58 and 60 seconds after the start of ablation. In some embodiments, the second data set 540d includes a distribution 539a of data sets (e.g., plotted points along distribution 539a), each of the data sets derived from at least some of the intra-cardiac voltage data sampled across a plurality of cardiac cycles during a period of time between a time just after that start of ablation and a time of approximately 60 seconds after the start of ablation. In some embodiments, each data set in the second data superset 540d is a respective one of a plurality of voltage magnitude sets. In some embodiments, and in a manner similar to various embodiments described above, each of the data sets in the second data superset 540d include data representative of a difference between two values (e.g., a difference between a maximum value and a minimum value (e.g., a maximum peak-to peak value)) of at least some of the intra-cardiac voltage data sampled during a respective one of the plurality of cardiac cycles, the difference being calculated from a sampling time excluding the excludable portion 542 in the respective one of the plurality of cardiac cycles, according to some embodiments. In some embodiments, other forms of data sets may be provided by the second data superset 540d. For example, each of the data sets in the second data set 540d may include data representative of a maximum value of at least some of the intra-cardiac voltage data sampled during a respective one of the plurality of cardiac cycles (e.g., excluding the respective excludable portion 542, according to some embodiments). In some embodiments, each of the data sets in the second data set 540d includes a voltage magnitude set that is frequency-weighted, e.g., as discussed above with respect to FIG. 7E.

In some embodiments, as shown in FIG. 9D, the concurrently displayed data sets in the second data set (or superset) 540d are displayed among at least a portion of the intra-cardiac electrogram 535b (e.g., concurrently displayed data sets of the first data set (or superset) 540c). In some embodiments according to FIG. 9D, the concurrently displayed data sets in the second data set 540d are displayed in an overlapping or superimposed configuration with at least part of the intra-cardiac electrogram 535b (e.g., which represents concurrently displayed data sets of the first data set 540c). In some embodiments according to FIG. 9D, the activation instructions associated with block 614 are configured to cause the electrode (e.g., 315, 415) that samples the intra-cardiac voltage data to also transmit energy sufficient for tissue ablation at least during the sampling of the intra-cardiac voltage data by the electrode during each of the plurality of cardiac cycles.

In some embodiments according to FIG. 9D, each of the data sets (e.g., data points) in the distribution 539a is derived via the computer-executable instructions associated with block 602-h and, in particular, in accordance with blocks 616 and 618. That is, each of the data sets in the second data set 540d is derived only from particular data that excludes an identified excludable portion (e.g., 542) of the intra-cardiac voltage data sampled during a respective one of the plurality of cardiac cycles.

In some embodiments according to FIG. 9D, the first data set 540c includes data derived from a respective portion of the intra-cardiac voltage data sampled by the electrode during each respective one of the plurality of cardiac cycles, each respective portion including at least some of the intra-cardiac voltage data that is excluded (e.g., forms part of an excludable portion) in the derivation of a particular data set in the second data set 540d derived from the intra-cardiac voltage data sampled during the respective one of the cardiac cycles. For example, the first set data 540c (e.g., intra-cardiac electrogram 535b) may be derived in accordance with various derivation instructions at least in part from intra-cardiac voltage data sampled during a plurality of times in a first cardiac cycle of the plurality of cardiac cycles, the plurality of times including at least a first time in the first cardiac cycle and a second time in the first cardiac cycle occurring after the first time in the first cardiac cycle. For example, FIG. 9C includes a representation of the intra-cardiac electrogram 535b associated with a period of time spanning 58-60 seconds from the start of ablation. An includable first portion 543a of the electrogram 535b is derived from intra-cardiac voltage data sampled during a first time in a first cardiac cycle (e.g., a first cardiac cycle represented by the respective portions in the electrocardiogram 523b indicated as P1, Q1, R1, S1 and T1) and a second portion 542a derived from intra-cardiac voltage data sampled during a second time in the first cardiac cycle. However, each of the data sets (e.g., voltage magnitude sets) in the second data set (or superset) 540d have been derived in some embodiments from particular data that excludes an excludable portion (e.g., a portion 542) of the intra-cardiac voltage data sample during a respective one of the cardiac cycles. In some embodiments, portion 542a is a member of, or forms part of, at least a portion 542, and while used in the derivation of at least part of the first data set 540c, does not form part of the particular data from which the second data set 540d is only derived from. In some embodiments according to FIG. 9D, the first data set 540c is represented as a first graphical distribution of data, and the second data set 540d (e.g., distribution 539a, like distribution 539) is represented as a second graphical distribution of data. The second graphical distribution of data may be derived only from particular data excluding respective portions (or particular parts) 542, each portion (or part) 542 including some, but not all, intra-cardiac voltage data sampled by the electrode during the respective cycle. The first graphical distribution (e.g., first data set 540c or electrogram 535b) may be derived from data that includes the respective portions (particular parts) 542. In some embodiments according to FIG. 9D, the second data set 540d is derived only from particular data that excludes at least some of the intra-cardiac voltage data sampled during the second time (e.g., portion 542a) in the first cardiac cycle, but also includes at least some of the intra-cardiac voltage data sampled by an electrode (e.g., 315, 415) during the first time in the first cardiac cycle and sampled by the electrode during a second cardiac cycle (e.g., a second cardiac cycle represented by the respective portions in the electrocardiogram 523b indicated as P2, Q2, R2, S2 and T2 in FIG. 9C). In some embodiments, transmission to the electrode of energy sufficient for tissue ablation occurs during the first and second cardiac cycles. In some embodiments according to FIG. 9D, the particular data from which the second data set 540d is derived excludes at least a portion of the intra-cardiac voltage data sampled during an occurrence of ventricular systole in the first cardiac cycle. In some embodiments, the particular data from which the second data set 540d is derived excludes a maximum absolute value of the intra-cardiac voltage data sampled during the first cardiac cycle. For example, with reference to FIG. 9C, the excluded portion 542a includes a portion of the V wave, the V wave having a peak value or maximum absolute value as compared to other values of the intra-cardiac electrogram 535 associated with this particular cardiac cycle (e.g., the first cardiac cycle).

In various embodiments, the concurrently displayed second data set 540d includes data derived from (a) a minimum value of the intra-cardiac voltage data sampled during the first time in the first cardiac cycle; (b) a maximum value of the cardiac voltage date sampled during the first time in the first cardiac cycle; or both (a) and (b). In some embodiments, the concurrently displayed second data set includes data derived at least in part from a mean value of the cardiac voltage data sampled during the first time in the first cardiac cycle. It is noted in various embodiments, that the first time in the first cardiac cycle can be any time (e.g., a continuous or discontinuous time interval) in the first cardiac cycle other than the second time. In this regard, in some embodiments, each respective one of the plurality of data sets is derived at least in part from at least one respective part of a portion, other than the excludable portion 542 (e.g., 542a), of the intra-cardiac voltage data sampled by an electrode (e.g., 315, 415) during a respective one of the plurality of cardiac cycles. The at least one respective part may include a first respective part including a minimum value, a second respective part including a maximum value, or both the first respective part and the second respective part, the minimum value and the maximum value being compared with other parts of the respective portion (which excludes the respective excludable portion 542, in some embodiments) of the intra-cardiac voltage data sampled by the electrode during the respective one of the plurality of cardiac cycles. In this regard, the at least one respective part may include a maximum absolute value in the respective one of the respective portion (which excludes the respective excludable portion 542, in some embodiments) of the intra-cardiac voltage data sampled by the electrode during the respective one of the plurality of cardiac cycles.

In this particular illustrated embodiment, the concurrently displayed second set 540d includes first data representative of a difference between two voltage values (e.g., a difference between a maximum value and a minimum value) of the intra-cardiac voltage data sampled during the first cardiac cycle (e.g., excluding the respective excludable portion 542, in some embodiments), and second data representative of a difference between two voltage values (e.g., a difference between a maximum value and a minimum value) of the intra-cardiac voltage data sampled during the second cardiac cycle (e.g., excluding the respective excludable portion 542, in some embodiments). For example, each of the plurality of data sets (e.g., data points, in some embodiments) in the second data set 540d may include data representative of a difference between a maximum value and a minimum value in the respective portion (which may exclude the respective excludable portion 542) of the intra-cardiac voltage data sampled by the electrode during the respective one of the plurality of cardiac cycles. In some embodiments, the concurrently displayed second data set 540d includes data representative of a peak value or a maximum absolute value of the intra-cardiac voltage values sampled during the first time in the first cardiac cycle.

In various embodiments associated with FIG. 9D, the concurrently displayed first data set 540c (e.g., forming some or all of intra-cardiac electrogram 535b) may be derived at least in part, not only from at least part of the intra-cardiac voltage sampled by an electrode (e.g., 315, 415) during a first cardiac cycle, but also from a second cardiac cycle. For example, the intra-cardiac electrogram 535b may be derived from intra-cardiac voltage data sampled by an electrode over multiple consecutive cardiac cycles. In some embodiments, the first data set 540c may be derived from a particular portion of the intra-cardiac voltage sampled by the electrode during the second cardiac cycle, while this particular portion (e.g., an excludable portion 542) may be excluded from derivation of the second data set 540d in this second cardiac cycle.

In FIG. 9D, the displayed intra-cardiac electrogram 535b is or includes at least a portion of a monophasic intra-cardiac electrogram in which each portion thereof that corresponds to a respective one of the cardiac cycles is represented by a monophasic waveform (e.g., as discussed above with respect to monophasic portion 536b). In particular, in FIG. 9D, the displayed portion of the intra-cardiac electrogram 535b includes a first monophasic portion of a part or portion of the intra-cardiac electrogram derived from at least some of the intra-cardiac voltage data sampled during the first cardiac cycle and a second monophasic portion of a part or portion of the other intra-cardiac electrogram 535b derived from at least part of the intra-cardiac voltage data sampled during the second cardiac cycle. Electrocardiogram 523b is also included in FIG. 9D.

It is noted that, in like embodiments associated with FIGS. 8A, 8B, and 8C and embodiments associated with FIGS. 8D, 8E, and 8F, the various display instructions (e.g., display instructions associated with block 604) may be configured to concurrently display the second data set 540*d* at least by displaying (a) the data included in the second data set 540*d* and derived at least in part from the at least some of the intra-cardiac voltage data sampled during the second cardiac cycle sequentially after (b) the data included in the second data set 540*d* and derived at least in part from the intra-cardiac voltage data sampled during the first time in the first cardiac cycle while continuing to display (b) to cause both (a) and (b) to be concurrently displayed. In this regard, it is noted, that the first and second data sets 540*c*, 540*d* shown in FIG. 9D may undergo similar transformations as described above in the various embodiments with FIGS. 8A, 8B, and 8C and embodiments associated with FIGS. 8D, 8E, and 8F during various time intervals occurring during the ablation before the 58 second mark associated with FIG. 9D or during various time intervals occurring during the ablation after the 60 second mark associated with FIG. 9D.

Accordingly, in various embodiments, although FIGS. 9A-9D show electrogram 535*b*, which has been low-pass filtered pursuant to the discussions above with regard to FIG. 7E, a non-low-pass filtered electrogram (e.g., akin to electrogram 535*a* in FIG. 7A) may instead be displayed (e.g., as at least part of one of the subpanels displaying at least one of the intra-cardiac electrograms 535 shown in the panel of intra-cardiac electrograms displayed by the graphical representation in FIGS. 5L and 5M), even if a low-pass filtered version of the electrogram is used to generate the second data superset 540*d*. In at least some of such embodiments, the displayed non-low-pass filtered electrogram (e.g., akin to electrogram 535*a* FIG. 7A) may undergo a biphasic (e.g., portion 536*a* in FIG. 7A) to monophasic (e.g., portion 536*b* in FIG. 7A) transformation during sequential display (e.g., displayed revealing) of the data sets (e.g., data points in some embodiments) of the second data superset 540*d* (e.g., at least part of the distribution 539*a*) over time (assuming that electrogram 535*b* is replaced with an electrogram akin to 535*a* in some embodiments). Similarly, in at least some of such embodiments, the displayed non-low-pass filtered electrogram (e.g., akin to electrogram 535*a* FIG. 7A) may include a first monophasic portion derived from at least some of the intra-cardiac voltage data sampled during a first cardiac cycle of the plurality of cardiac cycles and a second monophasic portion derived from at least part of the intra-cardiac voltage data sampled during a second cardiac cycle of the plurality of cardiac cycles (e.g., a second cardiac cycle occurring after the first cardiac cycle). The first monophasic portion and the second monophasic portion may be displayed with an amplitude of the first monophasic portion of the displayed portion of the intra-cardiac electrogram (e.g., akin to electrogram 535*a*) being greater than an amplitude of the second monophasic portion of the displayed portion of the intra-cardiac electrogram (e.g., akin to electrogram 535*a*). For example, note the reduction in the amplitude peaks of intra-cardiac electrogram 535*a* between 8 and 11 seconds in FIG. 7A, as discussed above. Similarly, in at least some of such embodiments, the display instructions associated with block 604 may be configured to cause the input-output device system (e.g., 120, 320) to display a non-low-pass filtered electrogram (e.g., akin to electrogram 535*a* FIG. 7A, instead of low-pass filtered electrogram 535*b* in FIG. 9D) as a monophasic intra-cardiac electrogram concurrently with at least the concurrently displayed second data set 540*d*. The monophasic intra-cardiac electrogram may include a plurality of portions, each portion of the monophasic intra-cardiac electrogram corresponding to a respective cardiac event (e.g., a R wave, V wave or other cardiac event, as discussed herein) occurring in a respective one of the plurality of cardiac cycles, the particular cardiac event being a same cardiac event. In various embodiments, the amplitudes of the particular cardiac events represented in the monophasic intra-cardiac electrogram by the plurality of portions, decrease over a time span that includes at least a first cardiac cycle and a second cardiac cycle. It is noted that in various embodiments, one or more other cardiac cycles of the plurality of cardiac cycles may occur between the first and the second cardiac cycles.

In FIG. 9D, the values of the data sets making up the concurrently displayed second data set 540*d* decay into a plateau region, which, in some embodiments provides an indication that a transmural lesion was achieved sometime at or before this time, as discussed above with respect to FIGS. 7 and 8.

While some of the embodiments disclosed above are described with examples of cardiac mapping, ablation, or both, the same or similar embodiments may be used for mapping, ablating, or both, other bodily organs, for example with respect to the intestines, the bladder, or any bodily organ to which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. An intra-cardiac voltage data display system comprising:
   a data processing device system;
   an input-output device system communicatively connected to the data processing device system; and
   a memory device system communicatively connected to the data processing device system and storing a program executable by the data processing device system, the program comprising:
   data reception instructions configured to cause reception of intra-cardiac voltage data via the input-output device system, the intra-cardiac voltage data sampled by an electrode over a period of time that includes a plurality of cardiac cycles;
   data derivation instructions configured to derive at least a first graphical distribution of data derived at least in part from a first portion of the received intra-cardiac voltage data and a second graphical distribution of data derived at least in part from a second portion of the received intra-cardiac voltage data; and
   display instructions configured to cause the input-output device system to concurrently display at least the first graphical distribution of data and the second graphical distribution of data, the displayed first graphical distribution comprising first data displayed across a first time scale and the displayed second graphical distribution comprising second data displayed across a second time scale having a different scale than the first time scale, the displayed first and second displayed graphical distributions concurrently displayed in a superimposed configuration.

2. The intra-cardiac voltage data display system of claim 1 wherein the data derivation instructions are configured to derive the second graphical distribution of data only from particular data, the particular data excluding, for each respective one of at least three of the plurality of cardiac cycles, a respective particular part of the intra-cardiac voltage data sampled by the electrode during the respective one of the at least three of the plurality of cardiac cycles, each respective particular part comprising some but not all of the intra-cardiac voltage data sampled by the electrode during the respective one of the at least three of the plurality of cardiac cycles, and wherein the data derivation instructions are configured to derive the first graphical distribution of data from data that comprises each of the respective particular parts.

3. The intra-cardiac voltage data display system of claim 2 wherein the program comprises:
cardiac event identification instructions configured to identify a respective occurrence of a particular cardiac event in each respective one of the at least three of the plurality of cardiac cycles; and
data identification instructions configured to identify, for each respective one of the at least three of the plurality of cardiac cycles, a particular portion of the intra-cardiac voltage data sampled during the respective one of the at least three of the plurality of cardiac cycles, each particular portion of the intra-cardiac voltage data sampled by the electrode during the respective one of the at least three of the plurality of cardiac cycles comprising some but not all of the intra-cardiac voltage data sampled by the electrode during the respective one of the at least three of the plurality of cardiac cycles, each particular portion of the intra-cardiac voltage data identified in accordance with a predetermined temporal relationship with the occurrence of the particular cardiac event identified in the respective one of the at least three of the plurality of cardiac cycles, and
wherein the particular data excludes at least some of each identified particular portion of the intra-cardiac voltage data sampled by the electrode during the respective one of the at least three of the plurality of cardiac cycles.

4. The intra-cardiac voltage data display system of claim 3 wherein the data derivation instructions are configured to derive the first graphical distribution of data from the respective particular portions.

5. The intra-cardiac voltage data display system of claim 1 wherein the displayed first graphical distribution comprises a first group of voltage magnitudes displayed across the first time scale, and the displayed second graphical distribution comprises a second group of voltage magnitudes displayed across the second time scale.

6. The intra-cardiac voltage data display system of claim 5 wherein (a) the first group of voltage magnitudes, (b) the second group of voltage magnitudes, or each of (a) and (b) is frequency-weighted.

7. An intra-cardiac voltage data display system comprising:
a data processing device system;
an input-output device system communicatively connected to the data processing device system; and
a memory device system communicatively connected to the data processing device system and storing a program executable by the data processing device system,
wherein the data processing device system is configured by the program at least to:
receive intra-cardiac voltage data via the input-output device system, the intra-cardiac voltage data sampled by an electrode over a period of time that includes a plurality of cardiac cycles;
derive at least a first graphical distribution of data derived at least in part from a first portion of the received intra-cardiac voltage data and a second graphical distribution of data derived at least in part from a second portion of the received intra-cardiac voltage data; and
cause the input-output device system to concurrently display at least the first graphical distribution of data and the second graphical distribution of data, the displayed first graphical distribution comprising first data displayed across a first time scale and the displayed second graphical distribution comprising second data displayed across a second time scale having a different scale than the first time scale, the displayed first and second displayed graphical distributions concurrently displayed in a superimposed configuration.

8. An intra-cardiac voltage data display method executed by a data processing device system according to a program stored by a memory device system communicatively connected to the data processing device system, the data processing device system further communicatively connected to an input-output device system, and the method comprising:
receiving intra-cardiac voltage data via the input-output device system, the intra-cardiac voltage data sampled by an electrode over a period of time that includes a plurality of cardiac cycles;
deriving at least a first graphical distribution of data derived at least in part from a first portion of the received intra-cardiac voltage data and a second graphical distribution of data derived at least in part from a second portion of the received intra-cardiac voltage data; and
causing the input-output device system to concurrently display at least the first graphical distribution of data and the second graphical distribution of data, the displayed first graphical distribution comprising first data displayed across a first time scale and the displayed second graphical distribution comprising second data displayed across a second time scale having a different scale than the first time scale, the displayed first and second displayed graphical distributions concurrently displayed in a superimposed configuration.

9. One or more non-transitory computer-readable storage mediums storing a program executable by one or more data processing devices of a data processing device system communicatively connected to an input-output device system, the program comprising:
a data reception module configured to cause reception of intra-cardiac voltage data via the input-output device system, the intra-cardiac voltage data sampled by an electrode over a period of time that includes a plurality of cardiac cycles;
a data derivation module configured to derive at least a first graphical distribution of data derived at least in part from a first portion of the received intra-cardiac voltage data and a second graphical distribution of data derived at least in part from a second portion of the received intra-cardiac voltage data; and
a display module configured to cause the input-output device system to concurrently display at least the first graphical distribution of data and the second graphical distribution of data, the displayed first graphical distribution comprising first data displayed across a first time scale and the displayed second graphical distribution comprising second data displayed across a second time scale having a different scale than the first time scale, the displayed first and second displayed graphical distributions concurrently displayed in a superimposed configuration.

\* \* \* \* \*